(12) United States Patent
Håkansson et al.

(10) Patent No.: US 11,369,320 B2
(45) Date of Patent: Jun. 28, 2022

(54) SYSTEMS AND METHODS INCLUDING A HUMAN-SHAPED GRAPHICAL ELEMENT

(71) Applicant: GAMBRO LUNDIA AB, Lund (SE)

(72) Inventors: Annmargret Håkansson, Kagerod (SE); Par-Olof Håkansson, Vellinge (SE); Maria Johnsson, Malmo (SE); Roger Nilsson, Hoor (SE); Bendik Torvin, Schaanwald (LI)

(73) Assignee: Gambro Lundia AB, Lund (SE)

( * ) Notice: Subject to any disclaimer, the term of this patent is extended or adjusted under 35 U.S.C. 154(b) by 937 days.

(21) Appl. No.: 15/740,932

(22) PCT Filed: Jun. 30, 2016

(86) PCT No.: PCT/EP2016/065307
§ 371 (c)(1),
(2) Date: Dec. 29, 2017

(87) PCT Pub. No.: WO2017/001561
PCT Pub. Date: Jan. 5, 2017

(65) Prior Publication Data
US 2018/0184985 A1    Jul. 5, 2018

(30) Foreign Application Priority Data
Jul. 2, 2015 (SE) .................................. 1550939-1

(51) Int. Cl.
*A61B 5/00* (2006.01)
*A61M 1/36* (2006.01)
(Continued)

(52) U.S. Cl.
CPC .......... *A61B 5/7435* (2013.01); *A61B 5/0215* (2013.01); *A61B 5/6866* (2013.01);
(Continued)

(58) Field of Classification Search
CPC .. A61M 1/16; A61M 1/1601; A61M 2205/18; A61M 2205/502
See application file for complete search history.

(56) References Cited

U.S. PATENT DOCUMENTS

| 6,738,052 B1 | 5/2004 | Manke |
| 7,033,539 B2 | 4/2006 | Krensky |

(Continued)

FOREIGN PATENT DOCUMENTS

| EP | 0904788 | 3/1999 |
| WO | WO 2004/044810 | 5/2004 |

(Continued)

OTHER PUBLICATIONS

PCT Search Report and Written Opinion for PCT/EP2016/065307 dated Sep. 15, 2016 (10 pages).

*Primary Examiner* — Leslie R Deak
(74) *Attorney, Agent, or Firm* — Mueting Raasch Group

(57) ABSTRACT

Graphical user interfaces for use with extracorporeal blood treatment systems may include a human-shaped graphical element and one or more process feature graphical elements. The human-shaped graphical element may be moved automatically or manually by users with respect to the process feature graphical elements to provide indications with respect to the process features corresponding to the human-shaped graphical element and the process feature graphical elements.

12 Claims, 33 Drawing Sheets

(51) Int. Cl.
  *A61B 5/0215*   (2006.01)
  *G06F 3/04842*  (2022.01)
  *G06F 3/0488*   (2022.01)
  *G06F 3/04847*  (2022.01)
  *G16H 40/63*    (2018.01)
  *A61M 1/16*     (2006.01)
  *G06F 3/0481*   (2022.01)
  *G16H 20/40*    (2018.01)
  *A61B 5/021*    (2006.01)
  *G06F 3/04845*  (2022.01)
  *G06F 3/04886*  (2022.01)

(52) U.S. Cl.
  CPC .............. *A61B 5/743* (2013.01); *A61B 5/744* (2013.01); *A61B 5/7475* (2013.01); *A61M 1/16* (2013.01); *A61M 1/1607* (2014.02); *A61M 1/3607* (2014.02); *A61M 1/3609* (2014.02); *A61M 1/3612* (2014.02); *A61M 1/3639* (2013.01); *A61M 1/3656* (2014.02); *G06F 3/0481* (2013.01); *G06F 3/0488* (2013.01); *G06F 3/04842* (2013.01); *G06F 3/04847* (2013.01); *G16H 20/40* (2018.01); *G16H 40/63* (2018.01); *A61B 5/021* (2013.01); *A61M 2205/3331* (2013.01); *A61M 2205/3334* (2013.01); *A61M 2205/3344* (2013.01); *A61M 2205/50* (2013.01); *A61M 2205/502* (2013.01); *A61M 2205/505* (2013.01); *A61M 2230/06* (2013.01); *G06F 3/04845* (2013.01); *G06F 3/04886* (2013.01)

(56) References Cited

U.S. PATENT DOCUMENTS

| 8,870,812 | B2 | 10/2014 | Alberti |
| 2009/0192823 | A1 | 7/2009 | Hawkins |
| 2012/0138533 | A1 | 6/2012 | Curtis |
| 2014/0099235 | A1 | 4/2014 | Ellingboe |
| 2014/0209519 | A1 | 7/2014 | Furuhashi |
| 2014/0344738 | A1 | 11/2014 | Lai |
| 2015/0014249 | A1 | 1/2015 | Alberti |
| 2015/0045641 | A1 | 2/2015 | Rule |
| 2015/0088054 | A1 | 3/2015 | Busby |

FOREIGN PATENT DOCUMENTS

| WO | WO 2010/007501 | 1/2010 |
| WO | WO 2013/182326 | 12/2013 |
| WO | WO 2014/024081 | 2/2014 |
| WO | WO 2014/033119 | 3/2014 |
| WO | WO 2014/103167 | 7/2014 |
| WO | WO 2014/124684 | 8/2014 |
| WO | WO 2014/151669 | 9/2014 |

SYSTEMS AND METHODS INCLUDING A HUMAN-SHAPED GRAPHICAL ELEMENT

This application is a U.S. National Stage Application of International Application No. PCT/EP2016/065307, filed 2016 Jun. 30 and published in English on 2017 Jan. 5 as International Publication No. WO 2017/001561 A1, which claims the benefit of priority under 35 U.S.C. § 119(a) of Swedish Patent Application No. 1550939-1 filed 2015 Jul. 2, each of which are incorporated herein by reference in their entireties.

The disclosure herein relates to medical treatment apparatus. More particularly, the disclosure relates to systems and methods for use in providing graphical user interfaces related to medical treatment apparatus such as extracorporeal blood treatment apparatus.

Medical treatment apparatus often includes a graphical user interface depicted on a display. A user may use the graphical user interface to, among other things, configure and setup a treatment, monitor and perform a treatment, and perform various post-treatment processes. The graphical user interface for treatment apparatus may include a plurality of different graphical elements, graphical regions, and graphical areas configured for performing the functionality associated with the treatment apparatus.

Medical treatment apparatus may be configured to perform extracorporeal blood treatment. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

The present disclosure describes systems and methods that use, or utilize, graphical user interfaces that depict one or more process feature graphical elements that may be moved about the graphical user interface to, e.g., indicate changes to states of process features corresponding to (e.g., representative of, associated with, etc.) the one or more process feature graphical elements. For example, the process feature graphical elements may be corresponding to fluid-circuit related process such as, e.g., dialysate processes, ultrafiltration processes, etc. and/or blood-circuit related processes such as, e.g., blood flow, blood priming, heparin delivery, citrate delivery, etc. The process feature graphical elements may be movable by a user to initiate or stop one or more process features corresponding to the process feature graphical elements. The movement of the process feature graphical elements may engage or disengage physical apparatus on a treatment system such as, e.g., connect the blood pump to the dialysate circuit. In one or more embodiments, the process feature graphical elements may be described as being "dragged" and "connected" to other process feature graphical elements (e.g., the process feature graphical elements may be referred to as "drag-and-connect" process feature graphical elements). Further, the process feature graphical elements may be automatically moved by the system when the one or more process features corresponding to the process feature graphical elements are initiated or stopped.

Upon viewing the graphical user interface including the locations and presentation of the process feature graphical elements, a user may be informed of the present state of the process features corresponding to (e.g., representative of, associated with, etc.) the process feature graphical elements. Further, the locations and presentation of the process feature graphical elements with respect each other and/or viewed as a whole may further provide additional information to the user regarding the present process features of the treatment system. In one or more embodiments described herein, each process feature graphical element may represent a portion of a prescription for an extracorporeal blood treatment, and the combination of the process feature graphical elements on the graphical user interface may represent the completed prescription.

One exemplary extracorporeal blood treatment system may include extracorporeal blood treatment apparatus for use during an extracorporeal blood treatment, a display apparatus, and a computing apparatus including one or more processors and operatively coupled to the extracorporeal blood treatment apparatus and the display apparatus. The extracorporeal blood treatment apparatus may include a blood pressure sensor to sense a patient's blood pressure. The display apparatus may include a graphical user interface configured to depict a human-shaped graphical element and a heart-shaped graphical element within the human-shaped graphical element. The computing apparatus may be configured to display on the graphical user interface the human-shaped graphical element and the heart-shaped graphical element at least partially within the human-shaped graphical element using the one or more processors, allow a user to select the heart-shaped graphical element to initiate the blood pressure sensor to perform a blood pressure measurement on the patient, determine the patient's blood pressure using the blood pressure sensor in response to selection of the heart-shaped graphical element, and display the measured blood pressure of the patient on the graphical user interface.

One exemplary method for an extracorporeal blood treatment system may include providing extracorporeal blood treatment apparatus for use during an extracorporeal blood treatment. The extracorporeal blood treatment apparatus may include a blood pressure sensor to sense a patient's blood pressure. The exemplary method may include displaying on a graphical user interface a human-shaped graphical element and the heart-shaped graphical element within the human-shaped graphical element, allowing a user to select the heart-shaped graphical element to initiate the blood pressure sensor to perform a blood pressure measurement on the patient, determining the patient's blood pressure using the blood pressure sensor in response to selection of the heart-shaped graphical element, and displaying the measured blood pressure of the patient on the graphical user interface.

In one or more embodiments, the measured blood pressure of the patient may be displayed at least partially within the human-shaped graphical element on the graphical user interface.

In one or more embodiments, the computing apparatus may be further configured to execute or the method may further include, upon initialization of the blood pressure sensor to perform a blood pressure measurement on the patient, graphically animating the heart-shaped graphical element to indicate that the user has initiated a blood pressure measurement and that the blood pressure measurement is occurring using the blood pressure sensor. For example, the graphical animation of the heart-shaped graphical element may include the heart-shaped graphical element pulsating.

In one or more embodiments, the extracorporeal blood treatment apparatus may further include a heart rate sensor to measure the patient's heart rate, and the computing apparatus may be further configured to execute or the method may further include allowing a user to select a heart rate area of the human-shaped graphical element to initiate the heart rate sensor to perform a heart rate measurement, determining the patient's heart rate using the heart rate sensor in response to selection of the heart rate area heart-shaped graphical element, and displaying the measured heart rate of the patient on the graphical user interface.

In one or more embodiments, the extracorporeal blood treatment apparatus may include one or more waste sensors to determine an amount of waste being removed from the patient, and the human-shaped graphical element may include graphical indicia indicative of the amount of waste removed from the patient.

In one or more embodiments, the human-shaped graphical element may include a graphical facial expression configured to indicate happiness when an extracorporeal blood treatment is complete.

In one or more embodiments, the graphical user interface may be configured to depict a graphical representation of at least one of the venous and arterial blood lines extending from the human-shaped graphical element and another graphical element on the graphical user interface to indicate that venous and arterial blood lines are connecting the patient to a blood circuit of the extracorporeal blood treatment apparatus. Further, for example, the extracorporeal blood treatment apparatus may include one or more blood circuit pressure sensors to measure venous blood circuit pressure and arterial blood circuit pressure in the blood circuit. The graphical user interface may be further configured to depict a blood circuit pressure graphical representation representative of at least one of venous blood pressure of the patient and arterial blood pressure of the patient measured by the one or more blood circuit pressure sensors proximate the graphical depiction of at least one of the venous and arterial blood lines.

In one or more embodiments, the computing apparatus may be further configured to execute or the method may further include allowing a user to select a graphical area proximate or within the human-shaped graphical element to display a patient information region on the graphical user interface comprising patient-related information. The patient-related information may include at least one of a prescription, medication condition history, treatment history, a treatment summary, patient notes, and vital signs.

In one or more embodiments, the computing apparatus may be further configured to execute or the method may further include displaying on the graphical user interface a blood process feature graphical element using the one or more processors. The human-shaped graphical element and the blood process feature graphical element may be separated by space, and the human-shaped graphical element may be movable proximate the blood process feature graphical element to indicate that venous and arterial blood lines are connecting the patient to a blood circuit of the extracorporeal blood treatment apparatus. Further, for example the human-shaped graphical element may further include a connection area corresponding to the blood process feature graphical element and the blood process feature graphical element may include a connection area corresponding to the human-shaped graphical element. The connection area of the human-shaped graphical element may be at least proximate to the connection area of the blood process feature graphical element when the human-shaped graphical element is proximate the blood process feature graphical element to indicate that venous and arterial blood lines are connecting the patient to the blood circuit of the extracorporeal blood treatment apparatus. Still further, for example, the connection area of the human-shaped graphical element may be configured to be in at least contact with the connection area of the blood process feature graphical element when the human-shaped graphical element is proximate the blood process feature graphical element.

An exemplary extracorporeal blood treatment system may include extracorporeal blood treatment apparatus to perform an extracorporeal blood treatment, a display apparatus, and a computing apparatus operatively coupled to the extracorporeal blood treatment apparatus and the display apparatus. The extracorporeal blood treatment apparatus may include blood circuit to circulate blood from a patient during the extracorporeal blood treatment. The blood circuit may be connectable to the patient using venous and arterial blood lines. The display apparatus may include a graphical user interface configured to depict a human-shaped graphical element and one or more process feature graphical elements. The human-shaped graphical element may be corresponding to (e.g., representative of, associated with, etc.) connection of a patient (e.g., a human) to the blood circuit using the venous and arterial blood lines. Each process feature graphical element of the one or more process feature graphical elements may be corresponding to (e.g., representative of, associated with, etc.) a different process feature of the extracorporeal blood treatment system. The computing apparatus may include one or more processors and may be configured to display on the graphical user interface the human-shaped graphical element and the one or more process feature graphical elements. The human-shaped graphical element and the one or more process feature graphical elements may be separated by space, and the human-shaped graphical element may be movable proximate (e.g., drag-and-connected to) the one or more process feature graphical elements to indicate that the venous and arterial blood lines are connecting the patient to the blood circuit.

An exemplary method for an extracorporeal blood treatment system may include providing extracorporeal blood treatment apparatus to perform an extracorporeal blood treatment. The extracorporeal blood treatment apparatus may include blood circuit to circulate blood from a patient during the extracorporeal blood treatment. The blood circuit may be connectable to the patient using venous and arterial blood lines. The exemplary method may include displaying on a graphical user interface a human-shaped graphical element and one or more process feature graphical elements. The human-shaped graphical element may be corresponding to (e.g., representative of, associated with, etc.) connection of a patient (e.g., a human) to the blood circuit using the venous and arterial blood lines. Each process feature graphical element of the one or more process feature graphical elements may be corresponding to (e.g., representative of, associated with, etc.) a different process feature of the extracorporeal blood treatment system. The human-shaped graphical element and the one or more process feature graphical elements may be separated by space, and the human-shaped graphical element may be movable proximate (e.g., drag-and-connected to) the one or more process feature graphical elements to indicate that the venous and arterial blood lines are connecting the patient to the blood circuit.

Another exemplary extracorporeal blood treatment system may include an extracorporeal blood treatment apparatus to perform an extracorporeal blood treatment, a display apparatus including a graphical user interface, and a computing apparatus including one or more processors. The computing apparatus may be operatively coupled to the extracorporeal blood treatment apparatus and the display apparatus. The extracorporeal blood treatment apparatus may include blood circuit to circulate blood from a patient during the extracorporeal blood treatment. The blood circuit may be connectable to the patient using venous and arterial blood lines. The graphical user interface may be configured to depict a human-shaped graphical element and one or more process feature graphical elements. The human-shaped graphical element may correspond to connection of a patient (e.g., a human) to the blood circuit using the venous and arterial blood lines. Each process feature graphical element of the one or more process feature graphical elements may correspond to a different process feature of the extracorporeal blood treatment system. The computing apparatus may be configured to display on the graphical user interface the human-shaped graphical element and the one or more process feature graphical elements using the one or more processors. The human-shaped graphical element and the one or more process feature graphical elements may be separated by space. The computing apparatus may be further configured to determine that the venous and arterial blood lines are connecting the patient to the blood circuit and move the human-shaped graphical element using the one or more processors proximate the one or more process feature graphical elements in response to determining that the venous and arterial blood lines are connecting the patient to the blood circuit.

Another exemplary method for an extracorporeal blood treatment system may include providing extracorporeal blood treatment apparatus to perform an extracorporeal blood treatment. The extracorporeal blood treatment apparatus may include blood circuit to circulate blood from a patient during the extracorporeal blood treatment. The blood circuit may be connectable to the patient using venous and arterial blood lines. The exemplary method may further include displaying on a graphical user interface a human-shaped graphical element and one or more process feature graphical elements. The human-shaped graphical element may correspond to connection of a patient (e.g., a human) to the blood circuit using the venous and arterial blood lines. Each process feature graphical element of the one or more process feature graphical elements may correspond to a different process feature of the extracorporeal blood treatment system, and the human-shaped graphical element and the one or more process feature graphical elements may be separated by space. The exemplary method may further include determining that the venous and arterial blood lines are connecting the patient to the blood circuit and moving the human-shaped graphical element proximate the one or more process feature graphical elements in response to determining that the venous and arterial blood lines are connecting the patient to the blood circuit.

In at least one embodiment, the extracorporeal blood treatment apparatus may include a blood sensor to determine whether blood is in the blood circuit, and determining that the venous and arterial blood lines are connecting the patient to the blood circuit may include sensing blood in the blood circuit using the blood sensor.

Another exemplary extracorporeal blood treatment system may include extracorporeal blood treatment apparatus to perform an extracorporeal blood treatment, a display apparatus including a graphical user interface, and a computing apparatus including one or more processors. The computing apparatus may be operatively coupled to the extracorporeal blood treatment apparatus and the display apparatus. The extracorporeal blood treatment apparatus may include blood circuit to circulate blood from a patient during the extracorporeal blood treatment. The blood circuit may be connectable to the patient using venous and arterial blood lines. The graphical user interface may be configured to depict a human-shaped graphical element and one or more process feature graphical elements. The human-shaped graphical element may correspond to connection of a patient (e.g., a human) to the blood circuit using the venous and arterial blood lines. Each process feature graphical element of the one or more process feature graphical elements may correspond to a different process feature of the extracorporeal blood treatment system. The computing apparatus may be configured to display on the graphical user interface the human-shaped graphical element and the one or more process feature graphical elements using the one or more processors. The human-shaped graphical element proximate to the one or more process feature graphical elements to show that the venous and arterial blood lines are connecting the patient to the blood circuit. The computing apparatus may be further configured allow a user to move the human-shaped graphical element away from the one or more process feature graphical elements to indicate to the one or more processors that the venous and arterial blood lines have been disconnected from the patient.

The exemplary method for an extracorporeal blood treatment system may include providing extracorporeal blood treatment apparatus to perform an extracorporeal blood treatment. The extracorporeal blood treatment apparatus may include blood circuit to circulate blood from a patient during the extracorporeal blood treatment. The blood circuit may be connectable to the patient using venous and arterial blood lines. The exemplary method may include displaying on a graphical user interface a human-shaped graphical element and one or more process feature graphical elements. The human-shaped graphical element may correspond to connection of a patient (e.g., a human) to the blood circuit using the venous and arterial blood lines. Each process feature graphical element of the one or more process feature graphical elements may correspond to a different process feature of the extracorporeal blood treatment system. The human-shaped graphical element may be proximate to the one or more process feature graphical elements to show that the venous and arterial blood lines are connecting the patient to the blood circuit. The exemplary method may further include allowing a user to move the human-shaped graphical element away from the one or more process feature graphical elements to indicate to the one or more processors that the venous and arterial blood lines are connecting the patient to the blood circuit.

In at least one embodiment, a confirmation region including, or depicting, a query asking the user whether the patient is physically disconnected from the blood circuit may be displayed on the graphical user interface. The computing apparatus may be further configured to execute or the method may further include allowing a user to answer affirmatively or negatively to the query of the confirmation region and moving the human-shaped graphical element proximate the one or more process feature graphical elements in response to the user answering the query negatively.

In one or more embodiments, the extracorporeal blood treatment apparatus may include one or more waste sensors to determine an amount of waste being removed from the patient and the human-shaped graphical element may include graphical indicia indicative of an amount of waste being removed from the patient.

In one or more embodiments, the extracorporeal blood treatment apparatus may include one or more blood-related parameter sensors to determine at least one blood-related parameter associated with the patient and the human-shaped graphical element may include the at least one blood-related parameter associated with the patient determined by the one or more blood-related parameter sensors.

In one or more embodiments, the human-shaped graphical element may include a graphical facial expression configured to indicate happiness when an extracorporeal blood treatment is complete.

In one or more embodiments, the graphical user interface may be configured to depict a graphical representation of at least one of the venous and arterial blood lines extending between the human-shaped graphical element and the one or more process feature graphical elements to indicate that the venous and arterial blood lines are connecting the patient to the blood circuit. In at least one embodiment, the extracorporeal blood treatment apparatus may include one or more blood circuit pressure sensors to measure venous blood circuit pressure and arterial blood circuit pressure in the blood circuit and the graphical user interface may be further configured to depict a blood pressure graphical representation representative of at least one of venous blood pressure of the patient and arterial blood pressure of the patient measured by the one or more blood circuit pressure sensors proximate the graphical representation of at least one of the venous and arterial blood lines.

In one or more embodiments, the graphical user interface may be configured to depict one or more affordance indications to indicate to a user where on the graphical user interface the one or more process feature graphical elements and the human-shaped graphical element are to be moved away from or proximate to. Further, the computing apparatus may be further configured to execute or the method further may include displaying one or more affordance indications proximate locations where on the graphical user interface the one or more process feature graphical elements and the human-shaped graphical element are to be moved away from or proximate to when the one or more process feature graphical elements and the human-shaped graphical element are moved.

In one or more embodiments, the computing apparatus may be further configured to execute or the method may further include, upon initialization of at least one process feature corresponding to the one or more process feature graphical elements and the human-shaped graphical element, displaying a graphical animation between at least two of the one or more process feature graphical elements and the human-shaped graphical element indicative of the change of state of the process features corresponding to the one or more process feature graphical elements and the human-shaped graphical element. In at least one embodiment, the graphical animation includes a flow of particles between a first process feature graphical element of the one or more process feature graphical elements and a second process feature graphical element of the one or more process feature graphical elements.

In one or more embodiments, the computing apparatus may be further configured to execute or the method may further include, upon initialization of the process features corresponding to the one or more process feature graphical elements and the human-shaped graphical element, displaying a graphical animation within the one or more process feature graphical elements and the human-shaped graphical element indicative of progression of the process features corresponding to the one or more process feature graphical elements and the human-shaped graphical element.

In one or more embodiments, the human-shaped graphical element may further include a connection area corresponding to a process feature graphical element of the one or more process feature graphical elements. The connection area of the human-shaped graphical element may be at least proximate to the corresponding process feature graphical element when the human-shaped graphical element is moved proximate the corresponding process feature graphical element graphical region to indicate a change in the state of the process feature corresponding to the human-shaped graphical element. In at least one embodiment, the connection area of the human-shaped graphical element may be configured to be in at least contact with the corresponding process feature graphical element when the human-shaped graphical element is moved proximate the corresponding process feature graphical element.

In one or more embodiments, after the human-shaped graphical element may be moved proximate the one or more process feature graphical elements, the human-shaped graphical element overlaps the one or more process feature graphical elements.

In one or more embodiments, the computing apparatus may be further configured to execute or the method may further include allowing a user to select the human-shaped graphical element to display a patient information region on the graphical user interface including patient-related information. The patient-related information may include at least one of a prescription, a medical condition history, a treatment history, a treatment summary, patient notes, and vital signs.

In one or more embodiments, the extracorporeal blood treatment apparatus may include at least one of a blood pressure sensor to measure the patient's blood pressure and a heart rate sensor to measure the patient's heart rate, and the computing apparatus may be further configured to execute or the method further may include allowing a user to select an area of the human-shaped graphical element to initiate at least one of a blood pressure measurement and a heart rate measurement. In at least one embodiment, the area of the human-shaped graphical element is heart-shaped.

In one or more embodiments, the computing apparatus may be further configured to execute or the method further may include displaying, in the one or more process feature graphical elements and the human-shaped graphical element, at least one parameter of the process features corresponding to the one or more process feature graphical elements and the human-shaped graphical element and allowing a user to select the one or more process feature graphical elements and the human-shaped graphical element to display an adjustment region configured to allow adjustment of the at least one parameter.

In one or more embodiments, the one or more process feature graphical elements may be representative of one or more blood-related process features of the extracorporeal blood treatment, and the one or more process feature graphical elements may be representative of one or more fluid circuit-related process features of the extracorporeal blood treatment.

In one or more embodiments, the one or more process feature graphical elements may be corresponding to at least one of blood flow, ultrafiltration, heparin delivery, citrate delivery, dialysate delivery, priming, disinfection, ultrafiltration profile, isolated ultrafiltration, rinseback, sodium profile, bicarbonate profile, pre-dilution, post-dilution, and potassium profile.

In one or more embodiments, the one or more process feature graphical elements may include at least two process feature graphical elements.

In one or more embodiments, the display apparatus may include a touchscreen.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
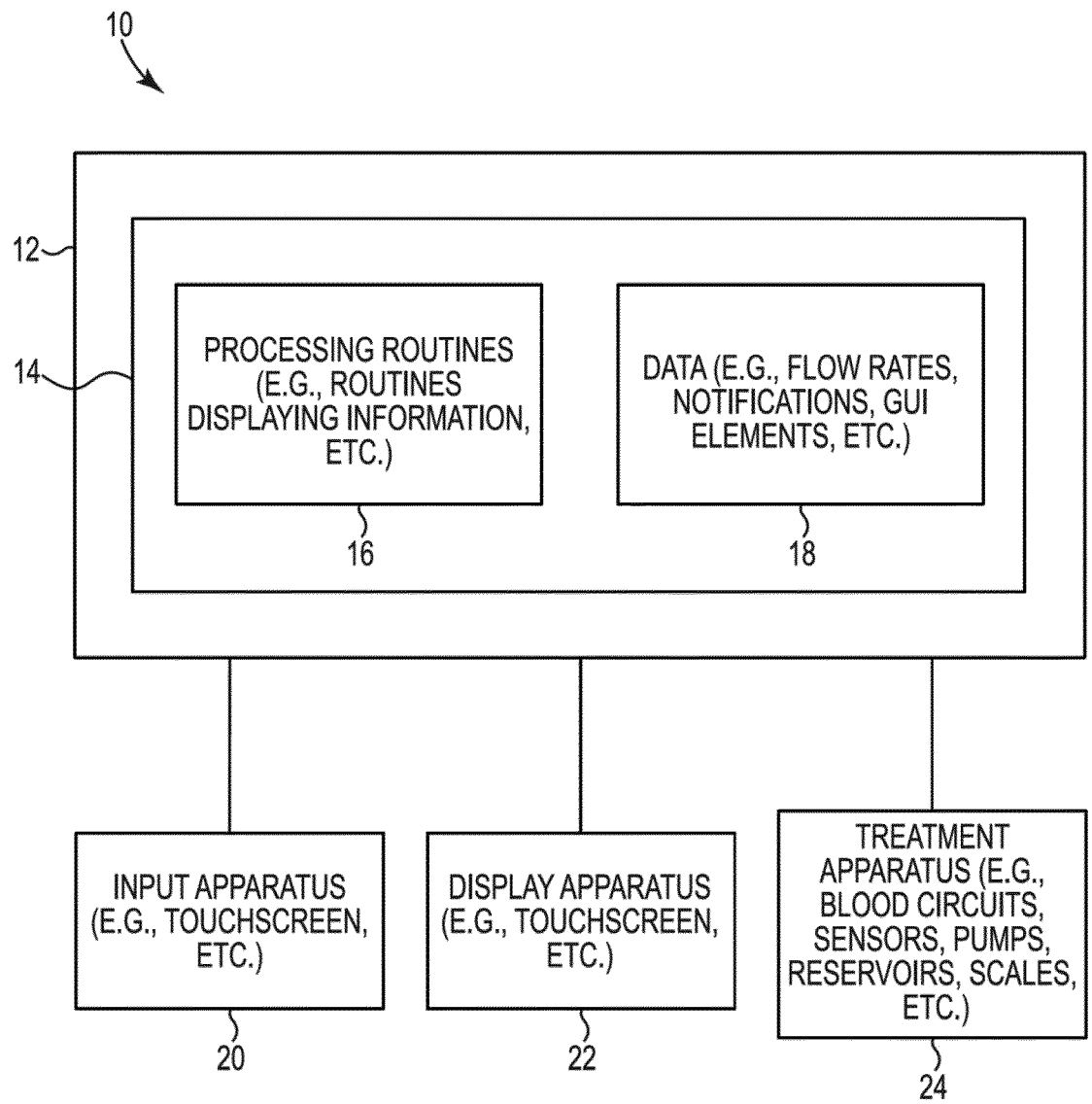
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary graphical user interface systems and methods for use with medical treatment apparatus such as, e.g., extracorporeal blood treatment apparatus, shall be described with reference to FIGS. 1-9. It will be apparent to one skilled in the art that elements or processes from one embodiment may be used in combination with elements or processes of the other embodiments, and that the possible embodiments of such graphical user interface systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may provide, or have, graphical user interfaces (e.g., user-interactable graphical user interfaces, graphical user interfaces depicted on single-touch or multi-touch touchscreens, etc.) that include, or depict, a plurality of graphical elements, graphical regions, and graphical areas configured to indicate the status of one or more processes (e.g., processes of an extracorporeal blood treatment system such as processes that are part of preparing/priming for extracorporeal blood treatments, performing extracorporeal blood treatments, performing post-treatment processes, etc.). The plurality of graphical elements, graphical regions, and graphical areas may each be configured to depict information (e.g., information to be conveyed to a user viewing and/or using the graphical user interface) and/or to allow a user to modify states of the processes related to, or associated with, the graphical elements, graphical regions, and graphical areas. Further, the plurality of graphical elements, graphical regions, and graphical areas together (e.g., all of the graphical elements, graphical regions, and graphical areas, the positioning of the graphical elements, graphical regions, and graphical areas with respect to each other, the completeness and/or uniformity of a user-recognizable form, or shape, defined by the graphical elements, graphical regions, and graphical areas positioned together, the graphical elements, graphical regions, and graphical areas when viewed as whole, etc.) may further be configured to depict information (e.g., information to be conveyed to a user viewing and/or using the graphical user interface) with respect to the processes related to, or associated with, each graphical element, graphical region, and/or graphical area as well as one or more overall processes, of which the individual processes associated with the graphical elements, graphical regions, and graphical areas may be a part, or portion of.

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22.

Further, the computing apparatus 12 may include data storage 14. Data storage 14 may allow for access to processing programs or routines 16 and one or more other types of data 18 (e.g., graphical regions, graphical elements, graphical areas, graphical animations, parameters, metrics, variables, images, text strings, macros, etc.) that may be employed to perform, or carry out, exemplary methods and/or processes (e.g., displaying graphical user interfaces, allowing user interaction with graphical user interfaces, interpreting touch gestures on a touchscreen (e.g., swipes, drags, press-and-hold, touches, presses, etc.), displaying graphical elements, displaying textual elements, displaying status information, issuing alarms, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including an operation region containing, or depicting, graphical elements, graphical regions, and graphical areas associated with and representative of one or more process features to, e.g., change states of such process features, start or initiate such process features, stop or cease such process features, etc. when used in conjunction with the display apparatus 22 (e.g., displaying the graphical user interface). Further, for example, the input apparatus 20 may allow an operator to interact with a graphical user interface including a setup region containing, or depicting, information related to the setting up of an extracorporeal blood treatment to, e.g., modify one or more treatment parameters, change the type of treatment, etc. when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, and graphical areas.

For example, the graphical user interface displayed by the display apparatus 22 may include, or display, an operation region that may include multiple process feature graphical elements related to the extracorporeal blood treatment system. Each process feature graphical element may correspond to at least one feature of a process (e.g., flow rate, connection status, etc.). For example, a process feature graphical element may be associated with blood flow, and another process feature graphical element may be associated with dialysate flow. Each of these process feature graphical elements may be used by an operator to view status information corresponding to at least one process feature associated therewith. For example, the blood flow process feature graphical element may include information related to the blood flow rate and/or the blood circuit connection status (e.g., whether the blood circuit is operatively coupled to the dialysate/filtration circuit to perform an extracorporeal blood treatment, etc.), and the dialysate flow process feature graphical element may include information related to dialysate flow rate and/or the dialysate circuit connection status (e.g., whether the dialysate circuit is coupled to the blood/filtration circuit to perform an extracorporeal blood treatment, etc.).

Further, each process feature graphical element may correspond to one or more physical parts or portions (e.g., blood circuit, dialysate circuit, ultrafiltration circuit, blood connection to patient, etc.) of an exemplary extracorporeal blood treatment system. For example, moving (e.g., dragging-and-connecting) a process feature graphical element to another process feature graphical element may correspond to a physical part of the treatment system being physically coupled to another part of the treatment system. Further, for example, moving a process feature graphical element related to blood to a process feature graphical element related to dialysate may physically, operatively couple the blood circuit to the dialysate circuit. In other words, the process feature graphical elements may be related to, associated with, and/or representative of one or more physical parts or portions of an exemplary extracorporeal blood treatment system, and manipulating (e.g., moving, selecting, etc.) the process feature graphical elements may affect, or be reflective of, the physical parts or portions of the system. Additionally, it may be described that the process feature graphical elements are "linked" to the physical parts or portions an exemplary extracorporeal blood treatment system. Likewise, physical manipulation (e.g., physically moving, physically disconnecting/connecting, physically touching, etc.) of one or more parts or portions of an exemplary extracorporeal blood treatment system may affect the one or more process feature graphical elements corresponding to the physically manipulated parts or portions. For example, disconnecting a patient from the blood circuit may automatically initiate the movement of a blood process feature graphical element about the graphical user interface.

As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing computational mathematics, touchscreen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, variables, graphics (e.g., graphical elements, graphical areas, graphical regions, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
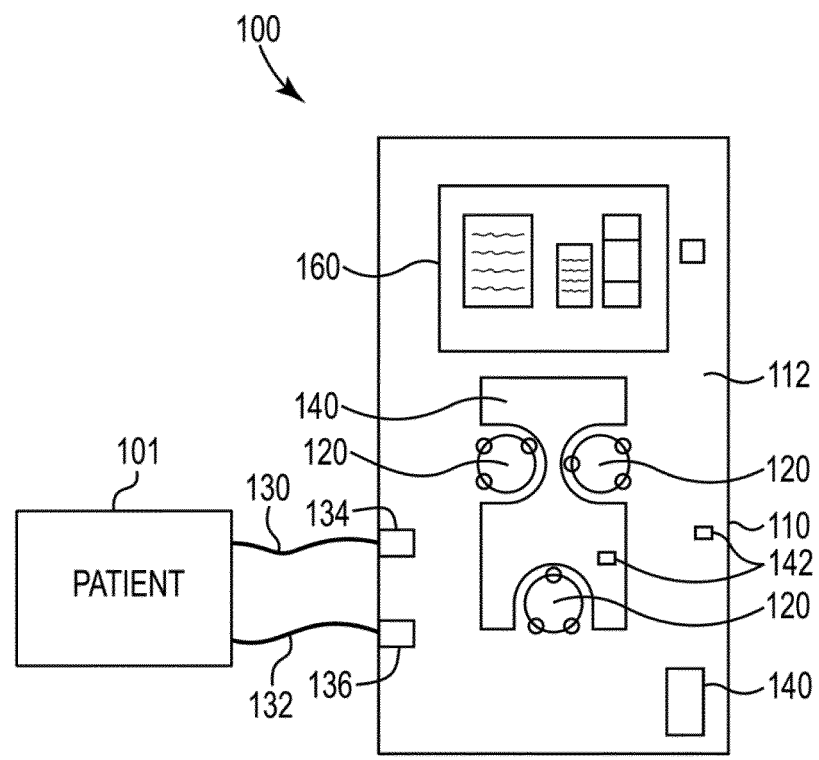
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements 140 (e.g., including or part of integrated modules), and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. and/or may not be visible on the outside of the housing 110. The one or more disposable elements 140 may be coupled to the system 100 for using in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors 142 of the system 100 for use in performing extracorporeal blood treatments. As shown, two disposable elements 140 appear to be coupled to the front face 112 of the housing 110 of the system 100 to, e.g., integrate with the one or more other fluid circuits, pumps 120, and sensors 142 of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable elements 140. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors 142 operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors 142 operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood-related parameter sensors 142 such as, e.g., flow rate sensors to monitor various blood flow rates throughout the blood circuits of the system 100, blood pressure sensors to monitor the diastolic and systolic blood pressure of the patient, blood circuit pressure sensors to monitor the arterial and venous blood lines pressures, heart rate sensors to measure the patient's heart rate, etc. Further, for example, the system 100 may include one or more waste sensors 142 configured to, or operable, to measure, or monitor, an amount of waste being removing from a patient (e.g., from a patient's blood), e.g., during the performance of an extracorporeal blood treatment. Further, for example the system 100 may include one or more fluid circuit or lines sensors 142 such as, e.g., blood circuit sensors to detect whether a blood circuit is coupled or uncoupled to the system, dialysate/dialysis fluid circuit sensors to detect whether a dialysate/dialysis circuit is coupled or uncoupled to the system, etc. In other words, one or more blood circuit sensors may be configured to detect whether a blood circuit is operatively coupled to the remainder of the extracorporeal blood treatment apparatus for use in an extracorporeal blood treatment and/or one or more dialysate/dialysis fluid circuit sensors may be configured to detect whether a dialysate/dialysis circuit is operatively coupled to the remainder of the extracorporeal blood treatment apparatus for use in an extracorporeal blood treatment. In one or more embodiments, the blood circuit and dialysate/dialysis fluid circuits may include some or all of the same sensors (e.g., when the blood circuit and dialysate/dialysis fluid circuit are part of the same disposable element or cartridge). Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

In one or more embodiments, the extracorporeal blood treatment system 100 may be configured for acute blood treatments (e.g., continuous renal replacement therapy) and may also include one or more devices, apparatus, and structures configured to perform the acute blood treatments. For example, the extracorporeal blood treatment system 100 may include reservoir sensors, or scales, (e.g., weight sensors, load cells, etc.), each of which is configured to hold and weigh a reservoir. The reservoir sensors may be positioned below the bottom end of the housing 110, at least in part because the reservoirs are typically attached to and hang from the reservoir sensors. The extracorporeal blood treatment systems described herein may include one or more reservoir sensors and associated reservoirs such as, e.g., as few as two reservoirs sensors and associated reservoirs, four or more reservoirs sensors and associated reservoirs, etc.

The extracorporeal blood treatment system 100 further includes a venous blood line/circuit 130 extending from a patient 101 (symbolically represented in FIG. 2) to the housing 110 to return blood to the patient 101 after the blood is treated by the system 100, an arterial blood line/circuit 132 extending from the patient 101 to the housing 110 to withdraw blood from the patient 101 for treatment, a venous blood circuit pressure sensor 134 configured to measure, or monitor, the pressure of the venous blood line/circuit 130 (e.g., the pressure of the blood, or fluid, within the venous blood line/circuit 130), and an arterial blood circuit pressure sensor 136 configured to measure, or monitor, the pressure of the arterial blood line/circuit 132 (e.g., the pressure of the blood, or fluid, within the arterial blood line/circuit 132). The venous and arterial blood circuits 130, 132 may connect the patient to a blood circuit (e.g., a disposable element 140) such that, e.g., blood of the patient may be circulated through the blood circuit to perform blood treatments thereon. In other words, the blood circuit may be connectable to a patient using the venous and arterial blood lines 130, 132.

The extracorporeal blood treatment system 100 also includes, in one or more embodiments, a display 160 used to show, or convey, information to an operator or user. The display 160 may also serve as an input device if, e.g., the display 160 is in the form of a touchscreen (e.g., a user interactable graphical user interface, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 are the pumps 120, blood circuits 130, 132, blood circuit pressure sensors 134, 136, and disposable elements 140 as shown in FIG. 2.

Exemplary graphical user interfaces, or portions thereof, for use in displaying information related to extracorporeal blood treatments, providing functionality to an operator for use in preparing and performing extracorporeal blood treatments and/or configuring or maintaining an extracorporeal blood treatment system are depicted in FIGS. 3-8. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Exemplary extracorporeal blood treatment systems may use, or utilize, a plurality of different graphical user interfaces. For example, some exemplary graphical user interfaces may be used to setup, or prepare, an extracorporeal blood treatment. Further, for example, some exemplary graphical user interfaces may be used during an extracorporeal blood treatment to monitor and/or adjust one or more parameters of the extracorporeal blood treatment. Still further, for example, some exemplary graphical user interfaces may be used post-treatment to clean/disinfect the system and to prepare the system for the next treatment. And still further, for example, some exemplary graphical user interfaces may be used to review system data regarding the performance and maintenance of the extracorporeal blood treatment system.

Each exemplary graphical user interface of the exemplary extracorporeal blood treatment systems described herein may include one or more graphical elements, regions, and areas used to display information to a user. An operator may use input apparatus 20 of the exemplary extracorporeal blood treatment system 10 described herein with reference to FIG. 1 to select or manipulate graphical elements, regions, and areas of the exemplary graphical user interfaces of FIGS. 3-8. As used herein, when an operator "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, an operator may select or interact with a graphical element, area, and/or region by "touching" the graphical region with their finger or using a pointing device such as a stylus. Further, for example, when the input apparatus includes a mouse or similar pointing device, an operator may select or interact with a graphical element, area, and/or region by locating an arrow or cursor over the desired graphical region "clicking" the graphical region. Still further, for example, when the input apparatus includes a series of buttons and/or knobs, an operator may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, select-and-drag, press, tracing of various shapes, pinch-inwardly, pinch-outwardly, finger spread, multi-finger touches and/or swipes, etc.

An exemplary graphical user interface 200 is depicted in FIGS. 3A-3F that may be generally used to configure, or "set up," an extracorporeal blood treatment before the extracorporeal blood treatment is performed. As shown, the graphical user interface 200 may include a plurality of graphical regions that may be used in the preparation of an extracorporeal blood treatment as well as other functionality and/or processes of the extracorporeal blood treatment system. At least one of the graphical regions may be more specifically referred to as an operation region 201, which is located within (e.g., located centrally within) the exemplary graphical user interface 200.

The operation region 201 may include various graphical regions, areas, and elements that may be used to indicate, initiate, revert, and stop one or more process features of processes of the extracorporeal blood treatment system. In the exemplary graphical user interface 200, the operation region 201 includes a plurality of process feature graphical elements such as, e.g., process feature graphical elements 212, 214, 216.

Each of the process feature graphical elements may be described as being corresponding to (e.g., representative of, associated with, etc.) at least one process feature of the extracorporeal blood treatment system. In the exemplary graphical user interface 200 depicted in FIGS. 3A-3F, the process feature graphical element 212 is corresponding to (e.g., representative of, associated with, etc.) the blood circuit, the process feature graphical element 214 is corresponding to (e.g., representative of, associated with, etc.) the dialysate circuit, and the process feature graphical element 214 is corresponding to (e.g., representative of, associated with, etc.) ultrafiltration. Further, collectively, the process feature graphical elements 212, 214, 216 may be described as being corresponding to (e.g., representative of, associated with, etc.) an overall, or primary, process. In the exemplary graphical user interface 200, the process feature graphical elements 212, 214, 216 are collectively corresponding to hemodialysis setup and priming, which may be indicated in title graphical region 203. In other words, the process feature graphical elements 212, 214, 216 may be used together, or in conjunction, to perform an overall, primary, process such as hemodialysis setup and priming. Additionally, as described herein, the process feature graphical elements 212, 214, 216 may also correspond to (e.g., representative of, associated with, etc.) one or more physical parts or portions of an extracorporeal blood treatment system related to, or linked to, the processes corresponding to the process feature graphical elements 212, 214, 216.

The operation region 201 of the exemplary graphical user interface 200 may further include a primary region 220. The primary region 220 may be described as a region of the operation region 201 and graphical user interface 200 that is spatially related to the plurality of process feature graphical elements 212, 214, 216 such that the position, or location, of the process feature graphical elements 212, 214, 216 with respect to the primary region 220 may be indicative of the states of the process features represented by and associated with the process feature graphical elements 212, 214, 216. In other words, the primary region 220 may be described as a central operating point or area from which the process feature graphical elements 212, 214, 216 may be located about, and the distance the process feature graphical elements 212, 214, 216 are located away from the primary region 220 (e.g., the central operating point) may indicate to a user (e.g., at a glance or quick look) the status of the process features represented by and associated with such process feature graphical elements 212, 214, 216. In other words, the primary region 220 may be described as a central operating point or area from which the process feature graphical elements 212, 214, 216 may be located about, and the distance the process feature graphical elements 212, 214, 216 are located away from the primary region 220 (e.g., the central operating point) may indicate to a user (e.g., at a glance or quick look) the status of the process features represented by and associated with such process feature graphical elements 212, 214, 216. In one or more embodiments, the primary region 220 may be stationary (e.g., the primary region 220 may not move or be allowed to be moved about the graphical user interface 200). In one or more embodiments, the primary region 220 may at least be temporally moveable about the graphical user interface 200. Further, in one or more embodiments, the primary region 220 may re-sizeable. For example, the primary region 220 (and the graphical regions, areas, elements, etc. thereof) may be expanded (e.g., increased in size, maximized, etc.) and/or shrunk (e.g., decreased in size, minimized, etc.) on the graphical user interface 200.

Additionally, in some embodiments, the primary region 220 may be described as a central control region configurable to perform, or initiate, one or more processes regardless of the state, or phase, of other processes of an exemplary extracorporeal blood treatment system. For example, the primary region 220, as will be described herein, may be used as a "Start" and "Stop" button for one or more pumps of the exemplary system, which may be used to either start or stop the one more pumps regardless of the state, or phase, of the exemplary system (e.g., within a treatment cycle, etc.). In other words, the primary region 220 may be described as being an independent, or "master," switch that is not dependent on other process features that may be controllable by other graphical regions, areas, and/or elements of the graphical user interface.

Also, in one or more embodiments, the primary region 220 may often be the next, or final, step in a process flow, or work flow, after one or more process features have been setup for a particular process. For example, after the system has been configured for priming, the next, or final, step to begin priming may be selection of the primary region 220 to initiate, or start, the priming. Further, for example, after the system has been primed and a patient has been operatively coupled to the system for treatment, the next, or final, step may be selection of the primary region 220 to initiate, or start, the blood pump.

Each process feature represented by and associated with the process feature graphical elements 212, 214, 216 may be configured in at least an active or inactive state. When a process feature is described to be configured in an inactive state, the process feature may, e.g., not be ready to execute or perform, not be presently performing, have one or more setup procedures before being ready to execute, etc. In other words, a process feature configured in an inactive state, which may be indicated by the process feature graphical element associated therewith also being configured in an inactive state as will be further described herein, may be not be ready for performing the one or more tasks associated with the process feature. Likewise, when a process feature is described to be configured in an active state, the process feature may, e.g., be ready to execute or perform, be presently performing, etc. In other words, a process feature configured in an active state, which may be indicated by the process feature graphical element associated therewith also being configured in an active state as will be further described herein, may be ready for performing or may be presently performing the one or more tasks associated with the process feature.

The process feature graphical elements 212, 214, 216 may be configured to indicate on the graphical user interface 200 the states (e.g., active, inactive, dormant, etc.) of the process features represented by and associated with the process feature graphical elements 212, 214, 216. The process feature graphical elements 212, 214, 216 may indicate the states of the process features in many different ways such as, e.g., alphanumerically, graphically through animation, graphically through colors or highlighting, spatially, changes in graphical form, flashing, etc. Additionally, the states of various process features may be indicated auditorily. For example, the treatment system may output one or more sounds corresponding to changes in the states of one or more process features. Further, for example, the treatment system may output one or more sounds corresponding to the present state of one or more process features.

Figure 3A:
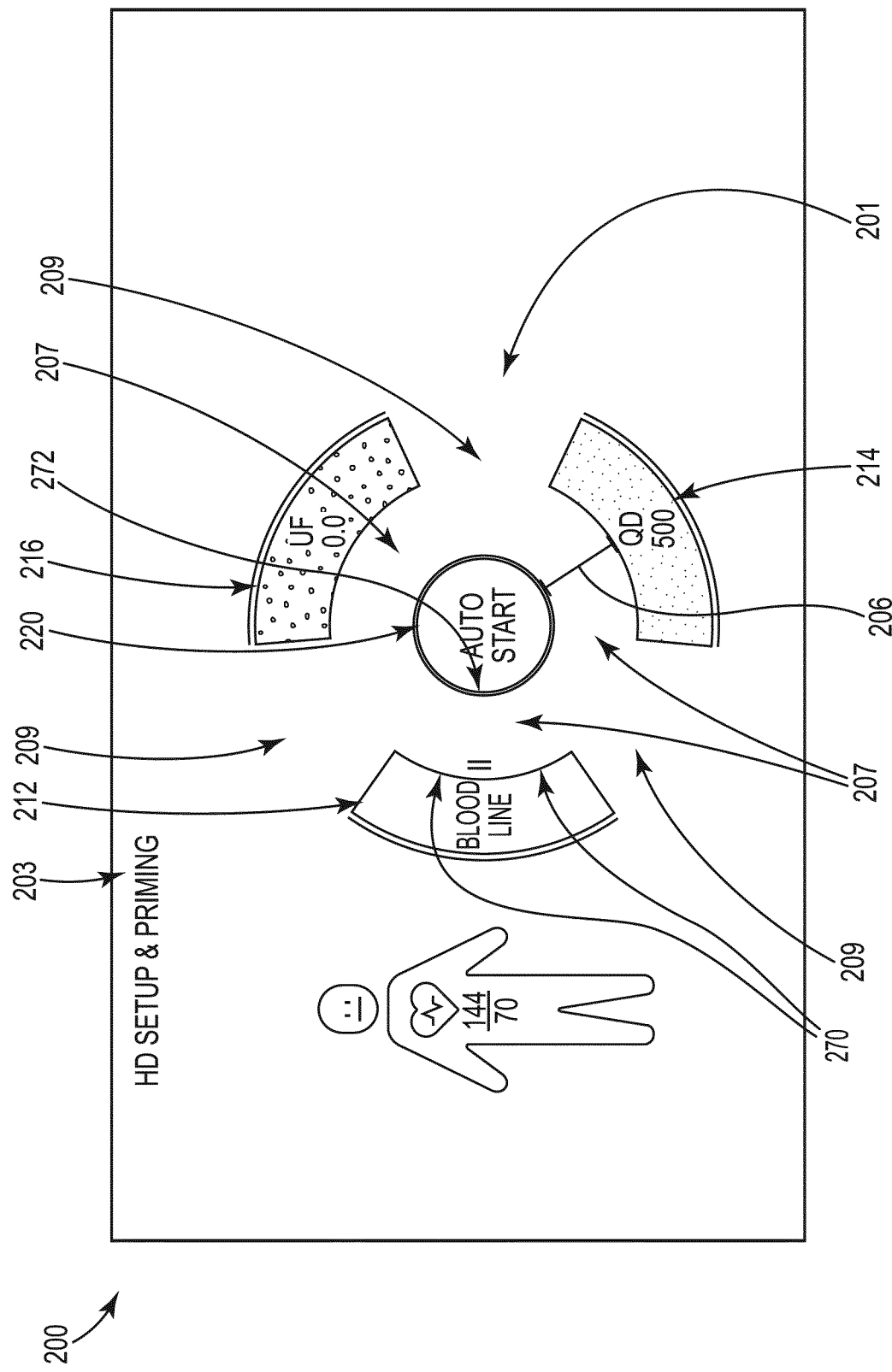
FIGS. 3A-3F depict an exemplary graphical user interface for use in setup and priming of a treatment using an extracorporeal blood treatment system such as, for example, shown generally in FIGS. 1-2.

As shown in FIG. 3A, the plurality of process feature graphical elements 212, 214, 216 may indicate the states of the process features represented by and associated therewith spatially. For example, the plurality of process feature graphical elements 212, 214, 216 and the primary region 220 may be separated by space 207, and the space 207 may indicate that the plurality of process feature graphical elements 212, 214, 216 are configured in an inactive, or latent, state. Likewise, the process features corresponding to the process feature graphical elements 212, 214, 216 that are in the inactive state may also be inactive (e.g., the processes may not be ready to execute, the processes may not be presently performing, etc.). Further, it may be described that the inactive process feature graphical elements may be visualized by detachment from the primary region 220. Conversely, for example, as will be described further herein, the plurality of process feature graphical elements 212, 214, 216 and the primary region 220 may not be separated by space 207, or at least less space 207 than when configured in the inactive state, to indicate that the plurality of process feature graphical elements 212, 214, 216 are configured in an active, or ready, state. Likewise, the process features corresponding to the process feature graphical elements that are configured in the active state may also be active (e.g., the processes may be ready to execute, the processes may be presently performing, etc.). Further, it may be described that the active process feature graphical elements may be visualized by attachment to the primary region 220.

Further, it may be described that the space 207 between a process feature graphical element and the primary region 220 defines a distance 206. In other words, the distance 206 may extend from a process feature graphical element to the primary region 220 when the process feature graphical element is configured in the inactive state. Conversely, when the process feature graphical element is configured in the active state, the distance 206 may not exist or may extend for less length than when the process feature graphical element was in the inactive state.

More specifically, as shown in FIG. 3A, the blood process feature graphical element 212 is separated from the primary region 220 by space 207, which indicates that the blood process feature graphical element 212 is configured in an inactive state. In turn, the blood process feature graphical element 212 being configured in an inactive state may indicate to a user that one or more blood-related process features are inactive. For example, the blood-related process feature (e.g., a blood circuit-related process feature) may be the blood circuit connection, or coupling, status, and the inactive state of the blood process feature graphical element 212 may indicate that the blood circuit is not connected (e.g., properly or fully connected) to the extracorporeal blood treatment system for priming prior to treatment. For instance, a change in the state of the blood-related process feature corresponding to the blood process feature graphical element 212 being moved proximate the primary graphical region 220 may include the blood circuit being operatively coupled to the remainder of the extracorporeal blood treatment apparatus for use in performing an extracorporeal blood treatment. Further, a change in the state of the blood-related process feature corresponding to the blood process feature graphical element 212 being moved away from the primary graphical region 220 may include the blood circuit being operatively uncoupled, or disconnected, from the remainder of the extracorporeal blood treatment apparatus, e.g., after a treatment has been completed.

Further, the dialysate process feature graphical element 214 is separated from the primary region 220 by space 207 and by distance 206, which indicates that the dialysate process feature graphical element 214 is configured in an inactive state. In turn, the dialysate process feature graphical element 214 being configured in an inactive state may indicate to a user that one or more dialysate-related process features are inactive. For example, the dialysate-related process feature (e.g., dialysate circuit-related process feature) may be dialysate circuit/line connection status, and the inactive state of the dialysate process feature graphical element 214 may indicate that the dialysate circuit is not connected (e.g., properly or fully connected) to the extracorporeal blood treatment system for priming prior to treatment. Further, for example, the dialysate-related process feature (e.g., dialysate circuit-related process feature) may be dialysate circuit operative coupling status, and the inactive state of the dialysate process feature graphical element 214 may indicate that the dialysate circuit is not operatively coupled, or connected, to the remainder of the extracorporeal blood treatment apparatus such as to the blood circuit so to be able to perform a blood treatment on the blood circulating in the blood circuit. For instance, moving the dialysate process feature graphical element 214 away from the primary graphical region 220 (when the dialysate process feature graphical element 214 is proximate the primary graphical region 220 during an ongoing blood treatment) may place an ongoing extracorporeal blood treatment into bypass and operatively uncouple the dialysate circuit from the remainder of the extracorporeal blood treatment apparatus.

Still further, the ultrafiltration process feature graphical element 216 is separated from the primary region 220 by space 207, which indicates that the ultrafiltration process feature graphical element 216 is configured in an inactive state. In turn, the ultrafiltration process feature graphical element 216 being configured in an inactive state may indicate to a user that one or more ultrafiltration-related process features are inactive. For example, the ultrafiltration-related process feature may be ultrafiltration status, and the inactive state of the ultrafiltration process feature graphical element 216 may indicate that ultrafiltration is not being performed by the extracorporeal blood treatment system during a treatment. Conversely, the active state of the ultrafiltration process feature graphical element 216, when the ultrafiltration process feature graphical element 216 is located proximate the primary region 220 and/or the other process feature graphical elements 212, 214, may indicate that ultrafiltration is being performed by the extracorporeal blood treatment system during a treatment. In other words, movement of the ultrafiltration process feature graphical element 216 may initiate or stop an ultrafiltration process of an ongoing extracorporeal blood treatment.

Additionally, as opposed to process feature graphical elements 212, 214, 216 being described with respect to the primary region 220, the plurality of process feature graphical elements may be further spatially described with respect to each other. For example, the plurality of process feature graphical elements 212, 214, 216 may also be separated from each other by space 209, which may indicate that the process feature graphical elements 212, 214, 216 are configured in an inactive, or latent, state. Conversely, for example, the plurality of process feature graphical elements 212, 214, 216 may not be separated from each other by space 209 or at least less space 209 than when configured in the inactive state, which may indicate that the process feature graphical elements are configured in an active, or executing, state.

Further, the process feature graphical elements with respect each other and/or viewed as a whole may provide additional information to the user regarding the associated process features and/or the overall, or primary, process associated with each of the process features. For example, at least some of the plurality of process feature graphical elements may be configured (e.g., shaped, sized, positioned, etc.) to form a user-recognizable form, or shape, when the process feature graphical elements are located proximate each other (e.g., not separated by 207 or distance 206, still separated by some space but located closed to each other than shown in FIG. 3A, etc.). The user-recognizable form, or shape, may be described as any shape recognizable by a user using the exemplary graphical user interface 200. Further, the completed, user-recognizable form, or shape, may be described as being only the perimeter of the shape or form (e.g., items inside of the perimeter may be inconsequential to the completed form, or shape). In the examples depicted in FIGS. 3-5, the user-recognizable form is a circle. In other examples such as shown in FIG. 6, the user-recognizable form may be a square or triangle. In one or more embodiments, the user-recognizable form may be described as being "seamless" when complete.

It may be further described that, when the plurality of process feature graphical elements are moved together, or dragged-and-connected to each other, (e.g., in conjunction with, or at the same time as, the plurality of process feature graphical elements 212, 214, 216 being moved proximate the primary region 220) to form a user-recognizable form, the plurality of process feature graphical elements may become, or create, a more harmonious, or congruous, shape, which may indicate that an overall, or primary, process associated with each of the process features of the process feature graphical elements 212, 214, 216 is ready to be performed or is being performed as will be described further herein with respect to FIGS. 4A-4L. In one or more embodiments, the movement (e.g., drag-and-connect) of the plurality of process feature graphical elements 212, 214, 216 to form a user-recognizable form or shape may indicate that a prescription has been completed for a treatment. In other words, a complete, user-recognizable form of the graphical user elements may indicate that all components of a prescription have been added to the treatment to fulfil the prescription. It may be described that a prescription includes, e.g., one or more parameters set, or programmed, by a user typically that may be identified by a patient identification number or similar. Further, the prescription may described as include all, or at least a portion, of the parameters and settings for carrying out, or performing, a treatment.

Figure 3B:
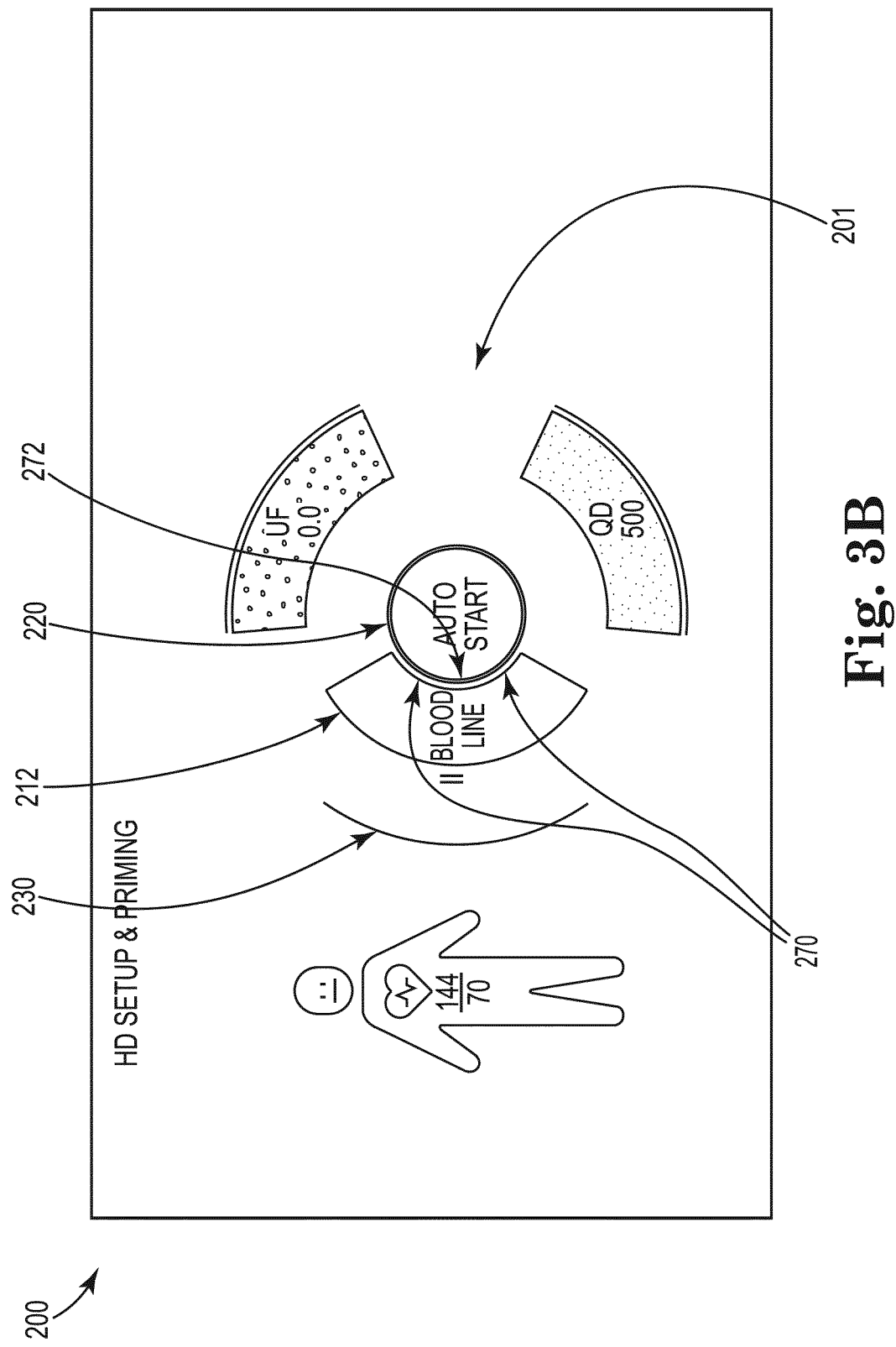

The blood process feature graphical element 212 has been moved proximate, or dragged-and-connected to, the primary region 220 as shown in FIG. 3B. Each of the process feature graphical elements may either be moved, or dragged-and-connected, by a user, e.g., to indicate that one or more process features associated therewith are initiated, resumed, or completed, to initiate, or start, one or more processes associated with the process feature graphical element, etc., or moved automatically by the treatment system, e.g., in response to one or more process features associated with the process feature graphical element initiating, one or more process features associated with the process feature graphical element completing, etc. In the example depicted in FIGS. 3A-3B, a user may move the blood process feature graphical element 212 towards a location proximate the primary region 220 to indicate that the blood line or circuit has been coupled, or connected, to the treatment system and configured such that the blood line or circuit is ready for priming. In other examples, the blood process feature graphical element 212 may be automatically moved towards a location proximate the primary region 220 by the system to indicate that the blood line or circuit has been properly coupled, or connected, to the treatment system (e.g., and the lid of the machine has been "closed") and configured such that the blood line or circuit is ready for priming.

The movement, or drag-and-connection, of the process feature graphical elements 212, 214, 216 with respect to each other and the primary region 220 may be further described in terms of "connection areas." For example, each of the process feature graphical elements 212, 214, 216 and the primary region 220 may define one or more connection areas. Each connection area may correspond to a different process feature graphical element of the one or more process feature graphical elements 212, 214, 216 and/or the primary region 220. A connection area may be defined as the area, or portion, of the process feature graphical element or primary region that is configured to be proximate, touching, or overlapping with a connection area of another process feature graphical element or primary region when configured in a state such as, e.g., an active state.

For example, the blood process feature graphical element 212 may define a connection area 270 and the primary region 220 may define a connection area 272. When the blood process feature graphical element 212 is moved proximate the primary region 220 as shown in the FIG. 3B, the connection areas 270, 272 of the blood process feature graphical element 212 and the primary region 220 (e.g., at or near the perimeter thereof), respectively, may be located proximate (e.g., adjacent, in contact, touching, closer to, etc.) each other to, e.g., indicate that the blood circuit or lines is coupled to the treatment system.

The operation region 201 may further include one or more affordances to indicate to a user where the process feature graphical elements may be moved to or away from. For example, as shown in FIG. 3B, an affordance indication 230 is depicted indicating where the blood process feature graphical element 212 (e.g., presently representing the blood circuit) had been moved from when configured in the inactive state as shown in FIG. 3A to indicate to a user that the blood process feature graphical element 212 may be moved back to the previous location proximate the affordance indication 230 (to, e.g., move the blood process feature graphical element 212 back to the inactive state). The affordance indication 230 may be further referred to as a "docking line" where the process feature graphical elements may be docked, or parked, when in an inactive state.

Figure 3C:
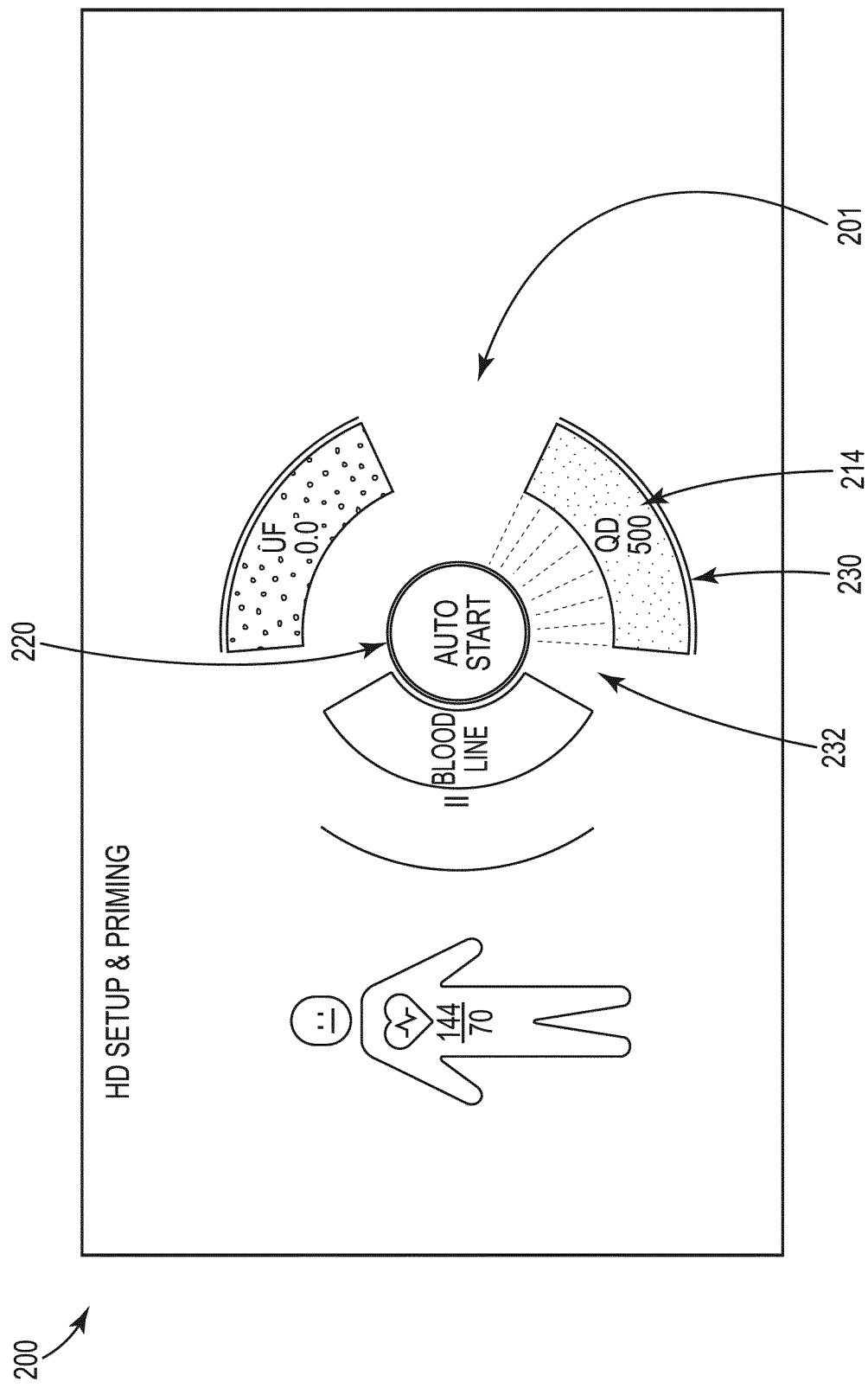

Further, while a process feature graphical element is being moved either to the primary region 220 or away from the primary region 220 towards the affordance indication 230, one or more affordances may be provided to indicate where the process feature graphical element may be moved to. For example, as shown in FIG. 3C, a movement affordance indication 232 may be displayed when a user selects the dialysate process feature graphical element 214 to move towards the primary region 220. The movement affordance indication 232 may include one or more graphical indications and/or animations to indicate where the dialysate process feature graphical element 214 may be moved to. As shown in this example, the movement affordance indication 232 may include slanted-line highlighting extending between the dialysate process feature graphical element 214 and the primary region 220, which may indicate that the dialysate process feature graphical element 214 may be moved towards and proximate to the primary region 220 to, e.g., place or configure the dialysate process feature graphical element 214 in the active state. When the dialysate-related process feature (e.g., dialysate circuit-related process feature) is the dialysate line connection status, the active state of the dialysate process feature graphical element 214 may indicate that the dialysate circuit is connected (e.g., properly or fully connected) to the extracorporeal blood treatment system for priming prior to treatment. When the dialysate-related process feature (e.g., dialysate circuit-related process feature) is the dialysate circuit operative coupling status, the active state of the dialysate process feature graphical element 214 may indicate that the dialysate circuit is operatively coupled, or connected, to the extracorporeal blood treatment apparatus such as to the blood circuit so to be able to perform a blood treatment on the blood circulating in the blood circuit.

Figure 3D:
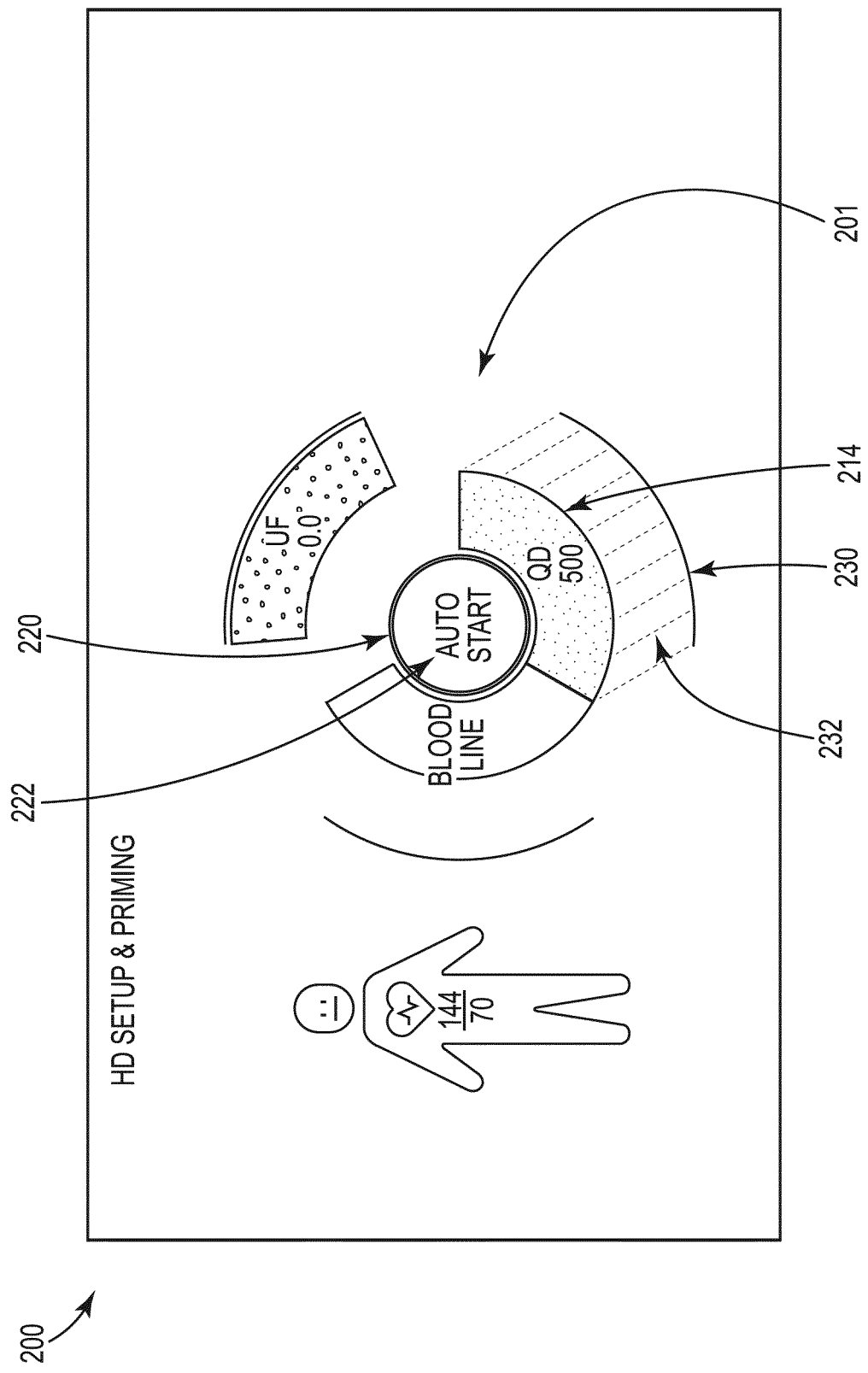

The movement affordance indication 232 may also indicate that the dialysate process feature graphical element 214 may be moved back to the affordance indication 230 to place, or configure, the dialysate process feature graphical element 214 in the inactive state while the dialysate process feature graphical element is being moved as shown in FIG. 3D. Additionally, although not shown in FIGS. 3C-3D, the movement affordance indication 232 may be shown on both sides of the dialysate process feature graphical element 214 when the dialysate process feature graphical element 214 is being moved and located between the primary region 220 and the affordance indication 230 (e.g., the movement affordance indication 232 may extend between both the dialysate process feature graphical element 214 and the primary region 220 and the dialysate process feature graphical element 214 and the affordance indication 230).

The dialysate process feature graphical element 214 has been moved (e.g., automatically moved by the system) proximate to the primary region 220 in FIG. 3D. In the example depicted in FIGS. 3A-3D, the treatment system may automatically move the dialysate process feature graphical element 214 towards a location proximate the primary region 220 to indicate that the dialysate line and/or circuit has been coupled to the system and configured such that the dialysate line or circuit is ready for priming (e.g., sensed or detected using one or more fluid circuit sensors, etc.). Further, a user may move (e.g., drag and connect) the dialysate process feature graphical element 214 towards a location proximate the primary region 220 to indicate that the dialysate line or circuit has been coupled to the system and configured such that the dialysate line and/or circuit is ready for priming.

In one or more embodiments, the treatment system may automatically move the dialysate process feature graphical element 214 towards a location proximate the primary region 220 to indicate that the dialysate line and/or circuit has been operatively coupled to the blood circuit and configured to perform a blood treatment on the blood circulating in the blood circuit (e.g., remove waste from the blood circulating in the blood circuit). Further, a user may move (e.g., drag and connect) the dialysate process feature graphical element 214 towards a location proximate the primary region 220 to operatively couple the dialysate line or circuit to the blood circuit and configured to perform a blood treatment on the blood circulating in the blood circuit (e.g., remove waste from the blood circulating in the blood circuit). In other words, movement of the dialysate process feature graphical element 214 may initiate or stop a blood treatment process of an extracorporeal blood treatment using the dialysate circuit.

After the blood process feature graphical element 212 and the dialysate process feature graphical element 214 have been moved proximate the primary region 220, each of the blood circuit and the dialysate circuit of the treatment system may be indicated as being ready for priming. In one or more embodiments, the treatment system may automatically begin priming once the blood process feature graphical element 212 and the dialysate process feature graphical element 214 have been moved proximate the primary region 220. Further, in one or more embodiments, a user may select an element, region, or area of the graphical user interface 200 to initiate priming. For example, the primary region 220 may be selectable to initiate or cease one or more processes, and in at least one example, may be selectable to initiate priming. In the embodiment depicted, however, the priming is configured to "Auto Start" upon the blood process feature graphical element 212 and the dialysate process feature graphical element 214 having been automatically moved proximate the primary region 220 and upon the detection of the blood circuit and dialysate circuit being properly physically attached to the treatment system. Thus, the treatment system may be described as being configured to self-initiate upon the detection of the blood circuit and dialysate circuit being properly physically attached, or coupled, to the treatment system.

Nonetheless, the primary region 220 may act as a button for one or more processes and/or process features. For example, the primary region 220 may be selectable to start, or initiate, the primary, or overall, process associated with or corresponding to the process features of the process feature graphical elements. For example, as shown in FIGS. 3A-3I, at least some of the process feature graphical elements are associated with hemodialysis setup and priming, and thus, the primary region 220 may be selectable to initiate or cease one or more processes of the hemodialysis setup and priming.

Further, the primary region 220 may include an alphanumeric indication 222 with respect to the operation of the primary region 220 as well as the overall, or primary, process. In this example, the priming is configured to automatically start, and thus, the alphanumeric indication 222 recites "AUTO START," which indicates that a priming process will automatically start, or initiate, once the treatment system is setup and ready for priming (e.g., the blood process feature graphical element 212 and the dialysate process feature graphical element 214 have been moved proximate the primary region 220, the detection of the blood circuit and dialysate circuit being properly physically attached to the treatment machine has occurred, etc.). In one or more embodiments, if the system is primed with a saline fluid, the dialysate process feature graphical element 214 may not need to be connected to the primary region 220 before priming.

Figure 3E:
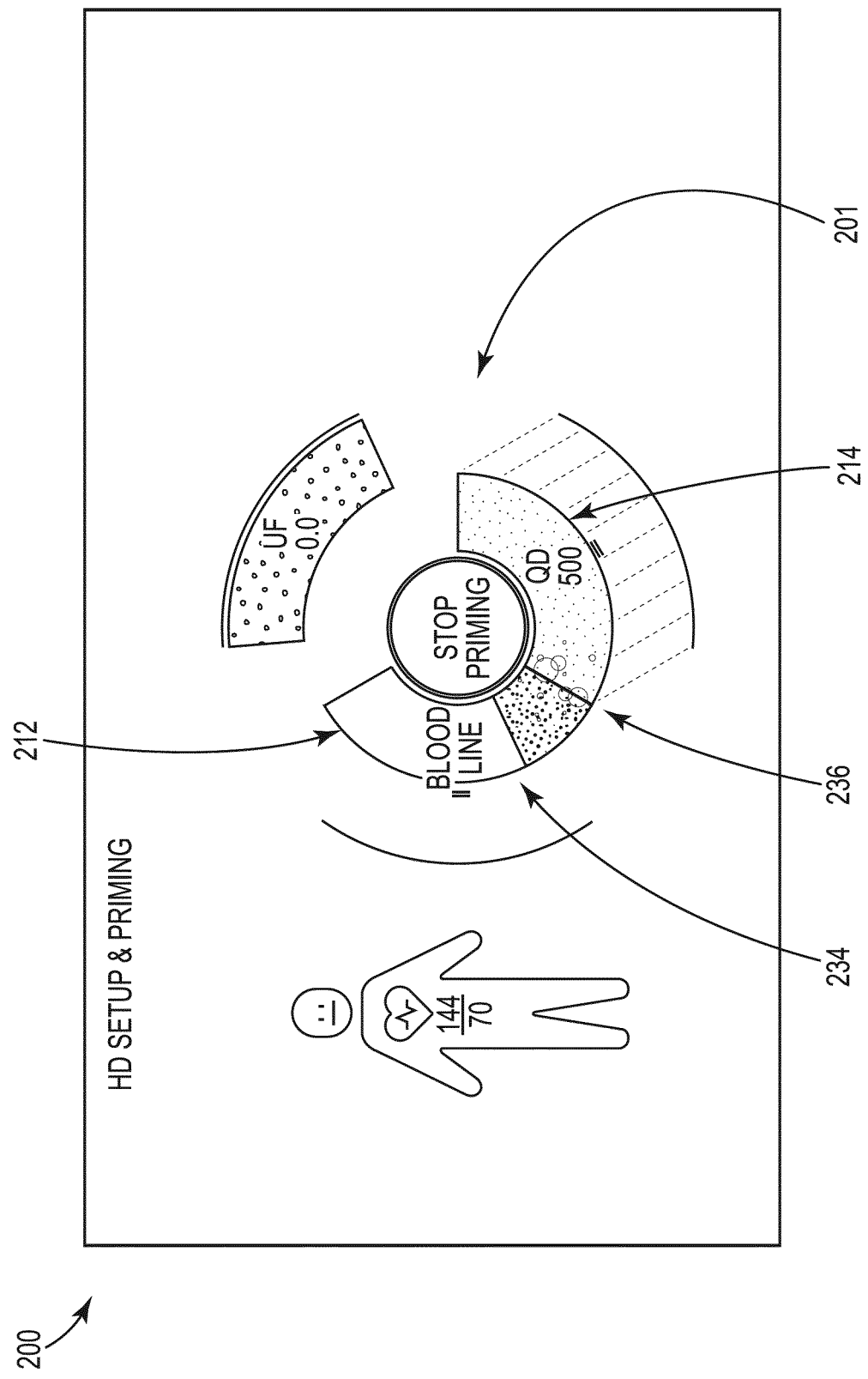

After the blood circuit and the dialysate circuit have begun priming, one or more graphical animations may be displayed on and/or between the process feature graphical elements associated with and representing the process features related to the blood circuit and dialysate circuit priming. For example, a fluidic progress bar may be displayed in the process feature graphical elements to indicate progression of priming each of the process features associated therewith. As shown in FIG. 3E, a fluidic progress bar 234 may be displayed in the blood process feature graphical element 212 to indicate progression of priming of the blood circuit.

Further, for example, a fluidic animation may be displayed between process feature graphical elements to indicate one or more processes occurring between the process features associated therewith. As shown in FIG. 3E, a fluidic animation 236 may be displayed in the blood process feature graphical element 212 and the dialysate process feature graphical element 214 to indicate that priming is occurring in and/or between the blood circuit and the dialysate circuit. The fluidic animation 236 may include graphical representations of a flow of particles such as bubbles and/or fluid particles exchanging, or moving, within and/or between the blood process feature graphical element 212 and the dialysate process feature graphical element 214. Further, the fluidic animation 236 may be described as graphically indicating connection of the blood process feature graphical element 212 and the dialysate process feature graphical element 214 and/or the operable coupling of apparatus and/or devices associated with the blood process feature graphical element 212 and the dialysate process feature graphical element 214 such as a blood circuit and dialysate circuit, respectively, through a dialyzer or filter.

Figure 3F:
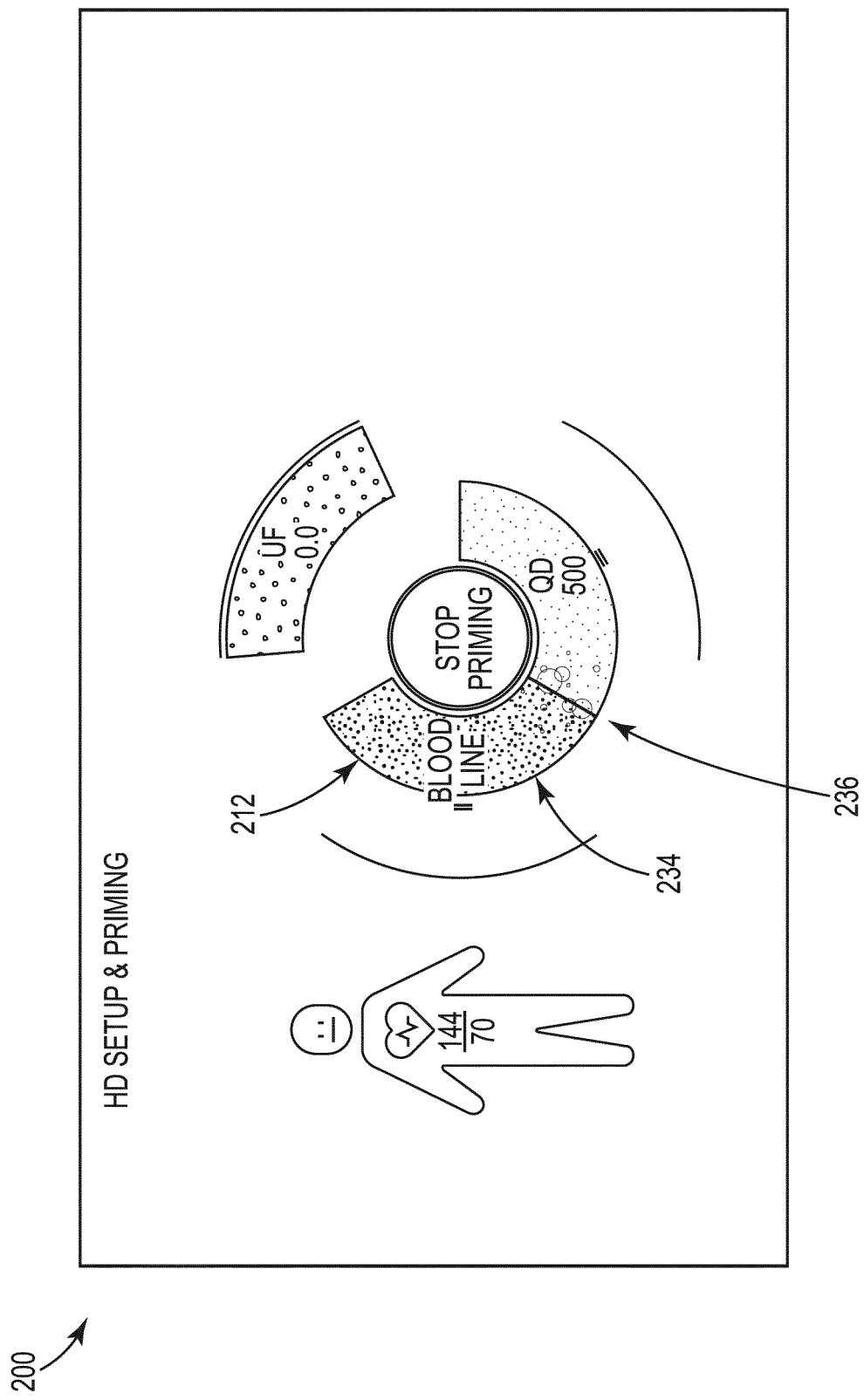

During priming, the primary region 220 may include the alphanumeric indication "STOP Priming" to indicate to a user that the user may select the primary region 220 to cease, or stop, the priming process. As shown in FIG. 3F, the fluidic progress bar 234 may indicate a completed process when the blood circuit is primed.

Figure 4A:
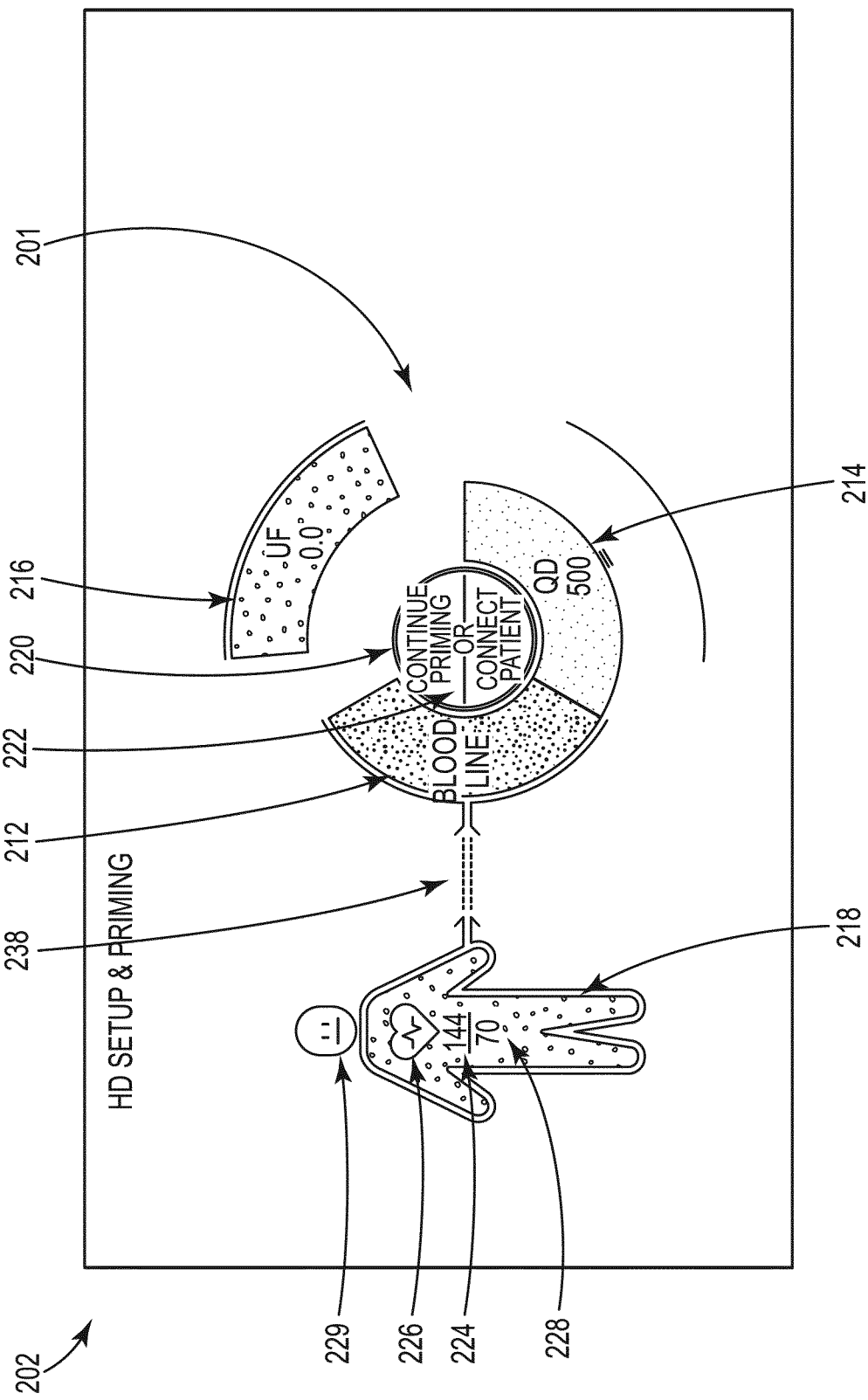
FIGS. 4A-4L depict an exemplary graphical user interface for use in performing a treatment using an extracorporeal blood treatment system such as, for example, shown generally in FIGS. 1-2.

Once the priming process is complete, the fluidic animation 236 may not be shown (e.g., the fluidic animation 236 may stop or cease) as shown in the exemplary graphical user interface 202 of FIG. 4A. The exemplary graphical user interface 202 of FIG. 4A-4L may be configured for use in performing a treatment using an extracorporeal blood treatment system, e.g., after setup and priming has been completed using the exemplary graphical user interface 200 as shown in FIGS. 3A-3F.

The exemplary graphical user interface 202 of FIG. 4A-4L may include an operation region 201 and further include the same or similar process feature graphical elements as the exemplary graphical user interface 200 of FIGS. 3A-3F. For example, the exemplary graphical user interface 202 may include an operation region 201 and a plurality of process feature graphical elements such as, e.g., process feature graphical elements 212, 214, 216.

Further, the exemplary graphical user interface 202 may include a human-shaped process feature graphical element 218 that is associated with and representative of the actual patient to be treated by the extracorporeal blood treatment system. As shown, the human-shaped process feature graphical element 218 may define a diagrammatic, or symbolic, representation of a human body. The human-shaped process feature graphical element 218 may define an outline, or perimeter, of the human body, or form, including a plurality of body parts or portions such as, e.g., two arms, two legs, a torso, a head, a neck, etc. As shown, the human-shaped process feature graphical element 218 appears to be in a standing or prone position. Further, the human-shaped process feature graphical element 218 may be recognizable by a user to represent the human patient to be treated by the system.

The human-shaped process feature graphical element 218 may further include one or more features, areas, and/or elements to indicate one or more blood-related parameters of the patient. For example, the human-shaped process feature graphical element 218 may include a blood pressure indication 224 that indicates the patient's present, or last measured, blood pressure value (e.g., as shown, 144 systolic over 70 diastolic) and a heart-shaped graphical element, or heart rate indication, 226 may indicate and/or initiate one or more process features related to a patient. The heart-shaped graphical element 226 may be described as being proximate the human-shaped process feature graphical element 218. In at least one embodiment, such as shown, the heart-shaped graphical element 226 may be located within the human outline of the human-shaped process feature graphical element 218. In other embodiments, the heart-shaped graphical element 226 may be partially located within or outside of the human outline of the human-shaped process feature graphical element 218.

The heart-shaped graphical element 226 may pulsate to indicate that the patient's heart rate and/or blood pressure is being presently measured. Further, a pulse or echocardiograph line graphically depicted with, or proximate, the heart-shaped graphical element 226 may be animated to indicate that the patient's heart rate and/or blood pressure is being presently measured. Further, the human-shaped process feature graphical element 218 may include additional graphical areas or regions configured to be selectable by a user to access (e.g., display) one or more patient records or settings for review and/or edit by a user.

The human-shaped process feature graphical element 218 may be selectable (e.g., touchable, clickable, etc.) to display a patient information region on, or over, at least a portion of the graphical user interface 202. The patient information region may include patient-related information. The patient-related information may include one or more items of information related to the patient such as, e.g., the patient's treatment history, the patient's medical condition history, a treatment summary, notes about the patient, the patient's medical records, the patient's prescription, the patient's treatment schedule, the patient's prescribed or un-prescribed medication, the patient's contact information, pre- and post-treatment data such as vital signs, patient appearance, patient comfort level, the patient's treatment report, etc. Further, a user may use the patient information region to edit one or more pieces of information displayed thereon.

Further, one or more regions, areas, or elements of the human-shaped process feature graphical element 218 may be selectable (e.g., touchable, clickable, etc.) to activate, or initiate, various actions or processes corresponding to, or related to, the patient (and related to, e.g., the blood pressure indication 224, the heart rate indication 226). For example, heart rate indication, or heart-shaped graphical element, 226 (e.g., the shape in the form of a heart), or another area of the human-shaped process feature graphical element 218, may be selectable by a user to initiate a blood pressure measurement of the patient. After the blood pressure measurement is performed, the blood pressure value of the blood pressure indication 224 may be updated (e.g., display the measured blood pressure values). Additionally, after a user has initiated a blood pressure measurement, e.g., by selecting the heart-shaped graphical element 226, the blood pressure indication 224 may be "cleared" of any previous blood pressure values (e.g., systolic and diastolic blood pressure values) such that user may visualize that a blood pressure measurement is presently occurring and not be confused by previous blood pressure values displayed in the blood pressure indication 224. For instance, the blood pressure values may be replaced by hyphens ("-"), en-dashes (".."), or em-dashes ("—") in response to the initiation of a blood pressure measurement. Further, for example, the heart-shaped graphical element 226 (e.g., the shape in the form of a heart), or another area of the human-shaped process feature graphical element 218, may be selectable by a user to initiate a heart rate measurement of the patient, and the value of measured heart rate may also be displayed after measurement. Also, as shown, the heart-shaped graphical element 226 of the human-shaped process feature graphical element 218 may be described as being located in the approximately, or about, the correct, or proper, anatomic location within the human form of the human-shaped process feature graphical element 218.

The human-shaped process feature graphical element 218 may further include waste graphical indicia 228 to indicate the amount of waste to be removed from the patient (e.g., monitored or measured using one or more sensors 142). The waste graphical indicia 228 may be defined by a fill color within the outline of the human of the human-shaped process feature graphical element 218, and as waste is removed from the patient, the fill color may be removed from within the human outline to indicate progression of the waste removal. In other words, the waste graphical indicia 228 within the human-shaped process feature graphical element 218 may be described as representing a waste-filled container from which the waste "drains" as the patient is treated. As shown in FIG. 4A, no waste has been removed from the patient since the treatment as not begun, and thus, the waste graphical indicia 228 indicates that no waste has been removed from the patient (e.g., the human-shaped process feature graphical element 218 is depicted as being full of waste). The waste graphical indicia 228 may be a "motivator" to the patient to assist the patient in understanding the treatment and the importance of staying through the entire treatment (e.g., if "yellow" waste remains in the human-shaped process feature graphical element 218, then the patient may see, or visualize, that the treatment has not completed). Additionally, the waste graphical indicia 228 may effectively communicate to the patient the progress of the treatment (e.g., such that the patient may determine, or gauge, how long treatment may take).

Additionally, the human-shaped process feature graphical element 218 may include a graphical facial expression 229 configured to indicate happiness when an extracorporeal blood treatment is complete (e.g., waste has been removed from the patient, etc.). As shown in FIG. 4A, no waste has been removed from the patient since the treatment has not begun, and thus, the graphical facial expression 229 does not indicate happiness. Instead, the graphical facial expression 229 appears neutral. Further, the graphical facial expression 229, or at least head portion of the human-shaped process feature graphical element 218, may be selectable by a user for documenting, editing, and/or reviewing a patient's physiological (e.g., vital signs, appearance, etc.) and/or psychological condition (e.g., mood) in a patient report graphical region.

The alphanumeric indication 222 of the primary region 220 may include the text "CONTINUE PRIMING OR CONNECT PATIENT," which indicates to a user that priming may be continued by, e.g., selecting the primary region 220, or the patient may be connected to the blood circuit for performance of the treatment. To indicate the next step, a patient connection affordance 238 may be provided extending between the blood process feature graphical element 212 and the human-shaped process feature graphical element 218 to, e.g., indicate that the next step, or task, is to physically connect the patient to the treatment system. The human-shaped process feature graphical element 218 may automatically move proximate the blood process feature graphical element 212 upon physical connection of the patient to the blood circuit (e.g., one or more sensors or other apparatus of the treatment system may determine that the patient has been physically connected to the blood circuit) and/or a user may move the human-shaped process feature graphical element 218 proximate to the blood process feature graphical element 212 after physical connection of the patient to the blood circuit to indicate that the patient is properly physically connected to the blood circuit for treatment.

Figure 4B:
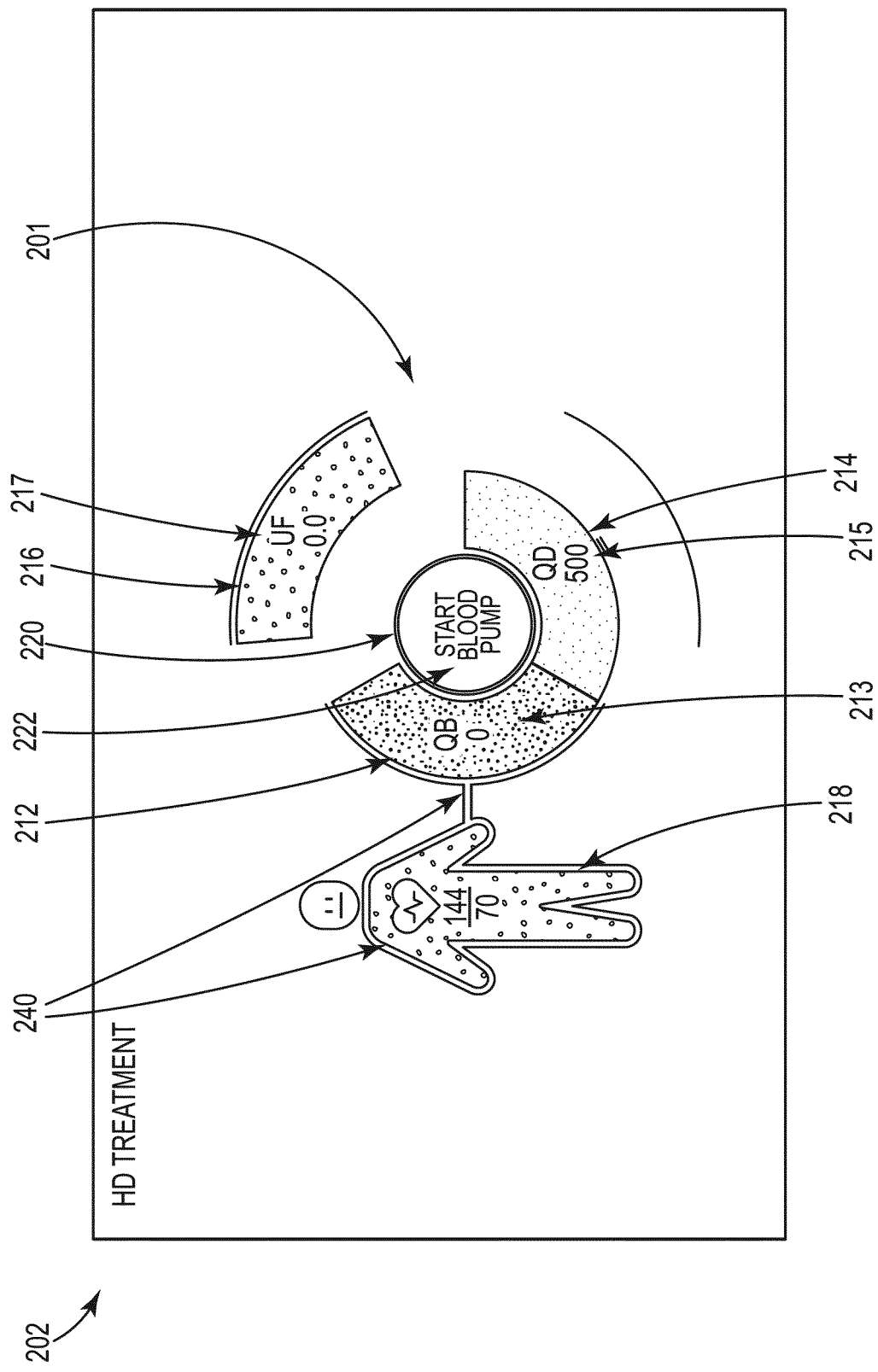
Figure 4C:
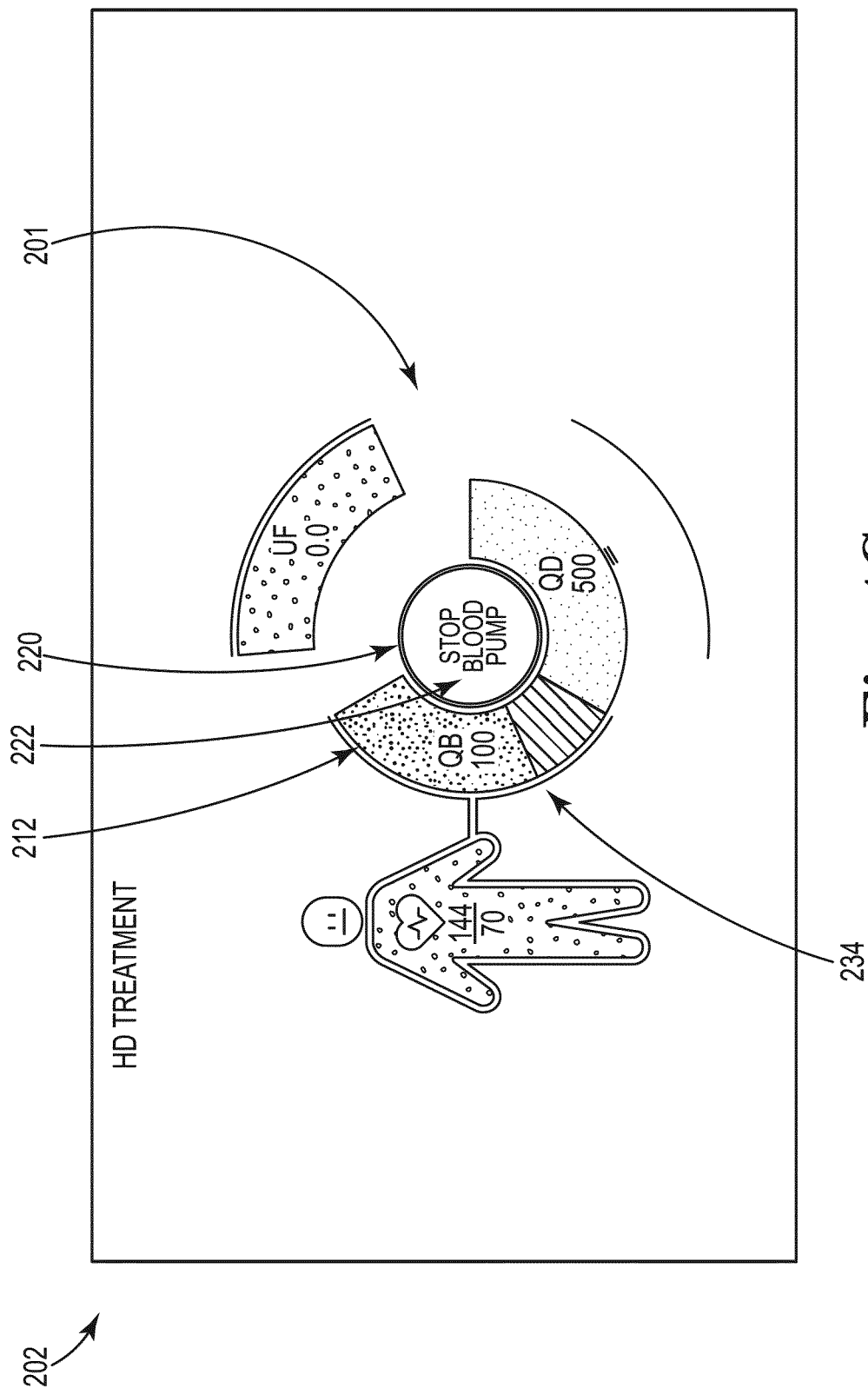
Figure 4K:
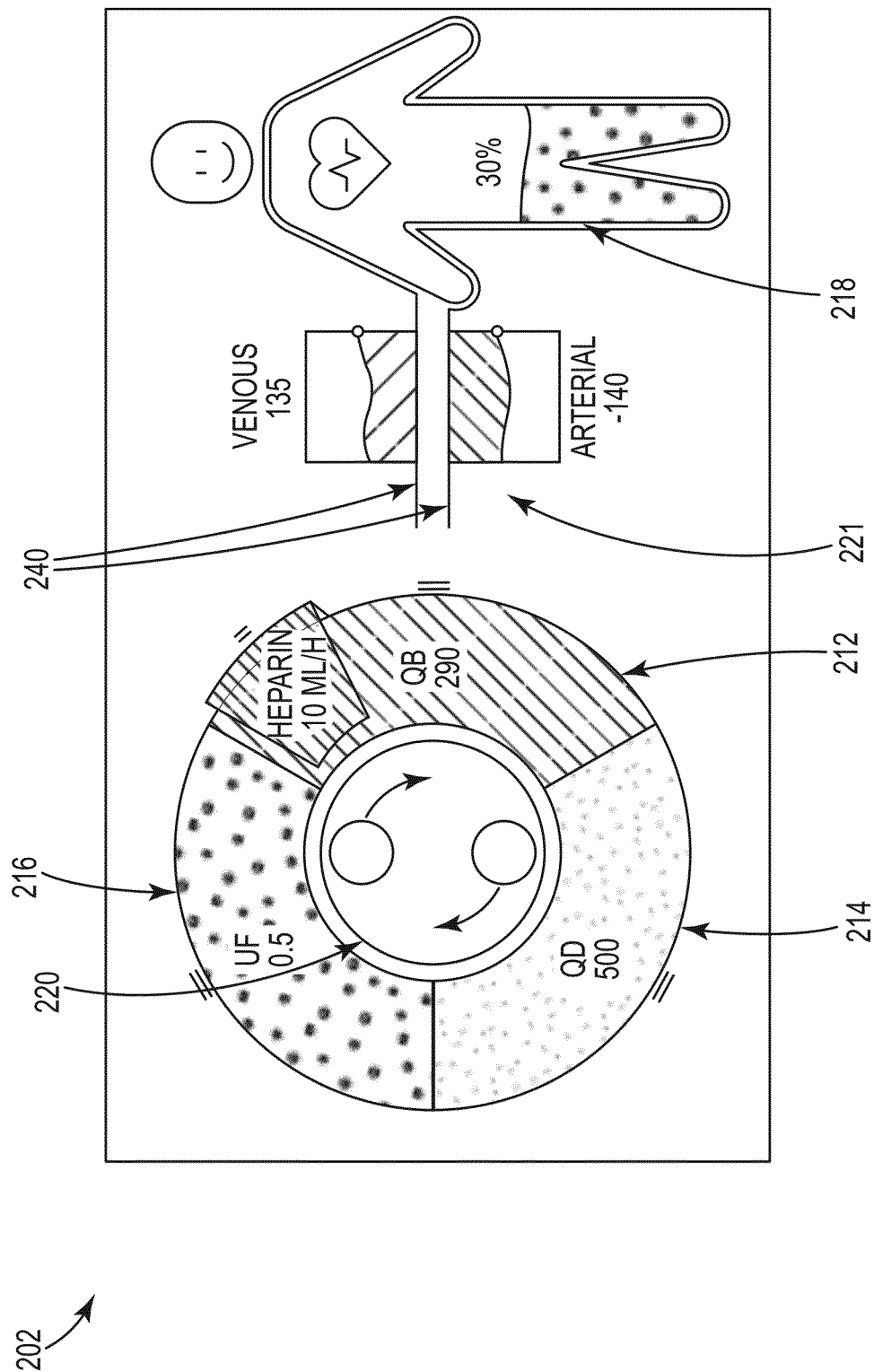
Figure 4L:
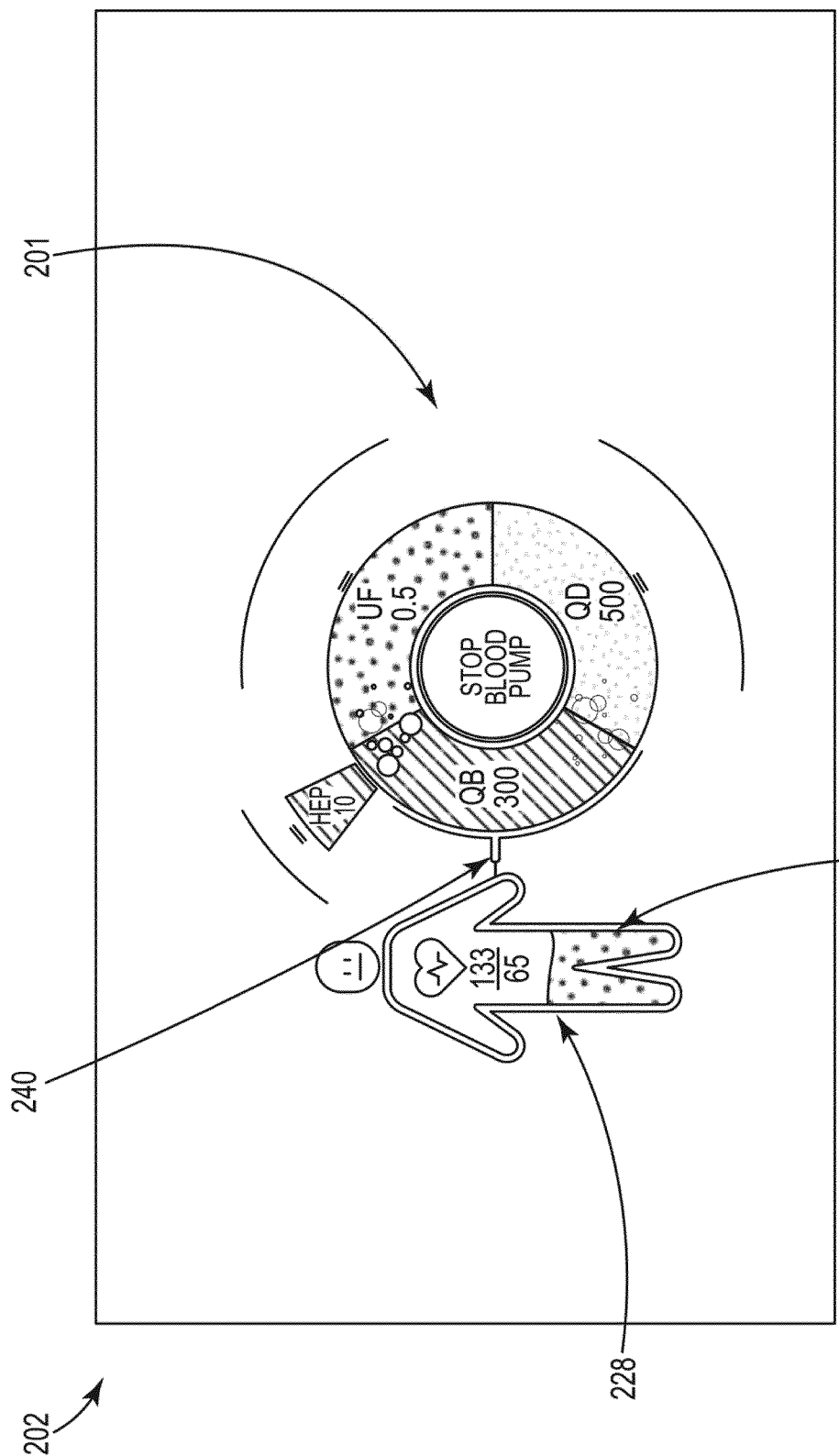
Figure 5A:
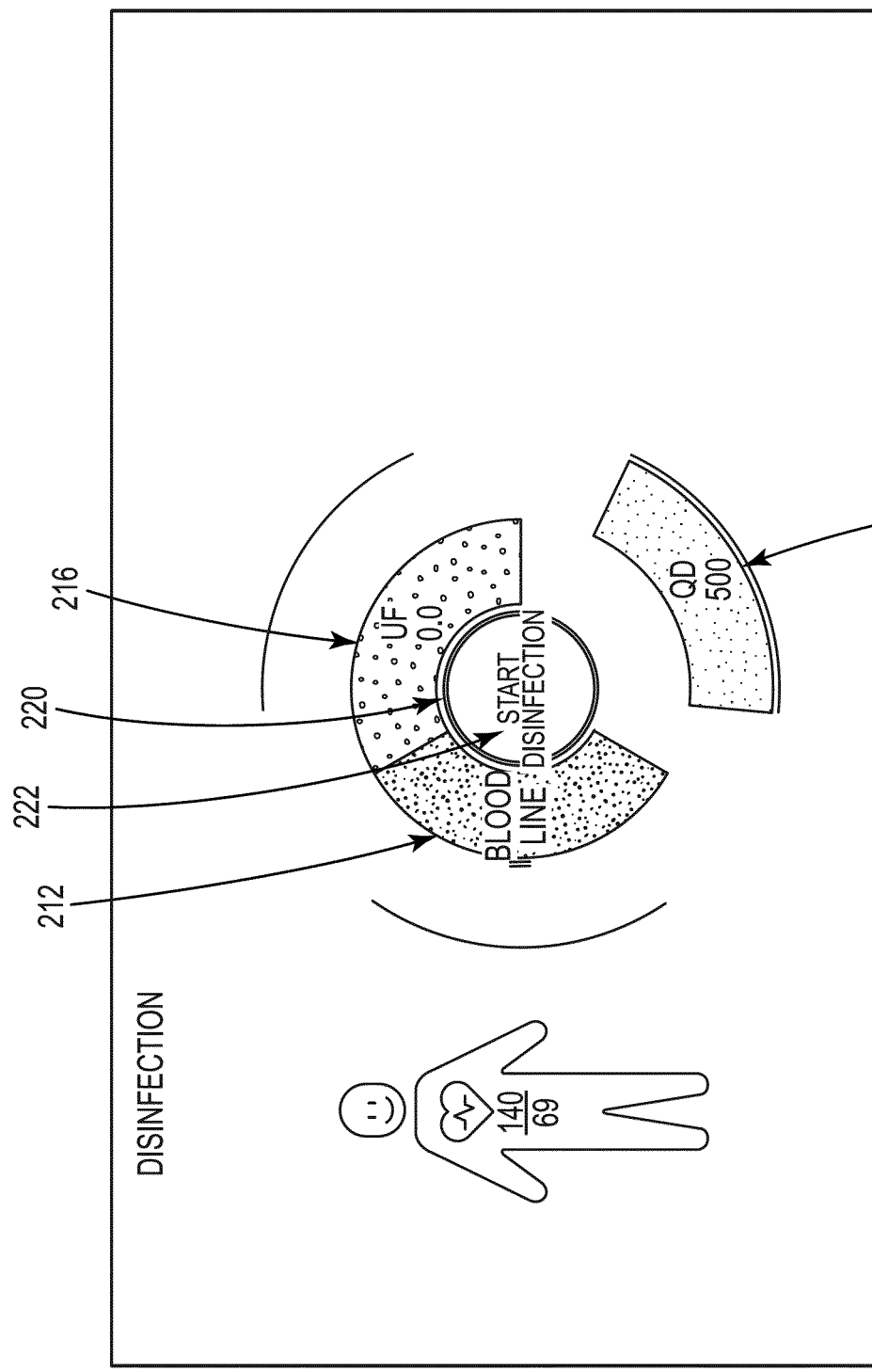
FIGS. 5A-5B depict an exemplary graphical user interface for use in performing a post-treatment process using an extracorporeal blood treatment system such as, for example, shown generally in FIGS. 1-2.

After the human-shaped process feature graphical element 218 is moved proximate the blood process feature graphical element 212 as shown in FIG. 4B, the treatment may be started. As shown, the alphanumeric indication 222 of the primary region 220 may include the text "START Blood Pump," which indicates to a user that the blood pump may be started to begin filling the blood circuit with the patient's blood prior to treatment, e.g., by selecting the primary region 220. Additionally, the primary region 220 may be graphically animated (e.g., flashing, highlighted, pulsing, etc.) to indicate to a user that the blood pump may be started to begin filling the blood circuit with the patient's blood prior to treatment, e.g., by selecting the primary region 220. During the operation of the blood pump, the primary region 220 may include a graphical animation of a blood pump running (e.g., a symbolic or graphical representation of a peristaltic pump rotating such as two dots orbiting a center point as shown in FIG. 4K). Further, a connection outline 240 may be depicted about the human-shaped process feature graphical element 218 and at least a portion of the blood process feature graphical element 212 after the human-shaped process feature graphical element 218 is moved proximate the blood process feature graphical element 212 to, e.g., indicate the physical coupling therebetween. In other words, the connection outline 240 may symbolically represent the connection of the patient to the blood circuit of the treatment system. Still further, the connection outline 240 as shown in FIG. 4B may include a pair, or two, connection lines extending between the human-shaped process feature graphical element 218 and the blood process feature graphical element 212 to graphically represent a venous blood line and an arterial blood line operatively coupling a patient to a blood circuit (e.g., a disposable element 140) of the extracorporeal blood treatment system. Additionally, in exemplary systems utilizing a single blood line operatively coupling a patient to a blood circuit, the connection outline 240 may include a single connection line extending from the human-shaped process feature graphical element 218 that splits, or forks, into two connection lines before contacting the blood process feature graphical element 212 to graphically represent such operatively coupling of a patient to a blood circuit (e.g., a disposable element 140) of the extracorporeal blood treatment system as shown in FIG. 4L.

As shown in FIG. 4A, the blood process feature graphical element 212 may depict, or include, the alphanumeric text describing the blood process feature graphical element 212 as being the "Blood Line." After movement of the human-shaped process feature graphical element 218 proximate the blood process feature graphical element 212 as shown in FIG. 4B, the alphanumeric text describing the blood process feature graphical element 212 may change (e.g., automatically) to "QB," which is indicative of blood flow rate.

Each of the process feature graphical elements may include one or more parameters related the process features associated therewith. For example, the process feature graphical elements may include flow rates, volumes, pressures, temperatures, dosages, prescription parameters, times, etc. As shown, for example, the blood process feature graphical element 212 may include blood flow rate 213, the dialysate process feature graphical element 214 may include dialysate flow rate 215, and the ultrafiltration process feature graphical element 216 may include the ultrafiltration rate 217.

Each of the process feature graphical elements may be selectable to display an adjustment region configured for a user to adjust one or more parameters associated therewith. For example, if the ultrafiltration process feature graphical element 216 is selected, an adjustment region 219 depicted in FIG. 9 may be displayed over the entire or a portion of the graphical user interface 200 such that, e.g., a user may use the various sliders, switches, bars, etc. to adjust one or more parameters associated with the ultrafiltration process.

As described herein, the blood pump may be started by selecting the primary region 220 to begin filling the blood circuit with the patient's blood. Once the blood pump has started as shown in FIG. 4C, the alphanumeric indication 222 of the primary region 220 may include the text "STOP Blood Pump," which indicates to a user that the blood pump may be stopped, e.g., by selecting the primary region 220. Additionally, the primary region 220 may be graphically animated (e.g., flashing, highlighted, pulsing, etc.) to indicate to a user that the blood pump may be stopped. Further, after the blood pump is started, a fluidic progress bar 234 may be displayed in the blood process feature graphical element 212 to indicate progression of blood filling the blood circuit.

Figure 4D:
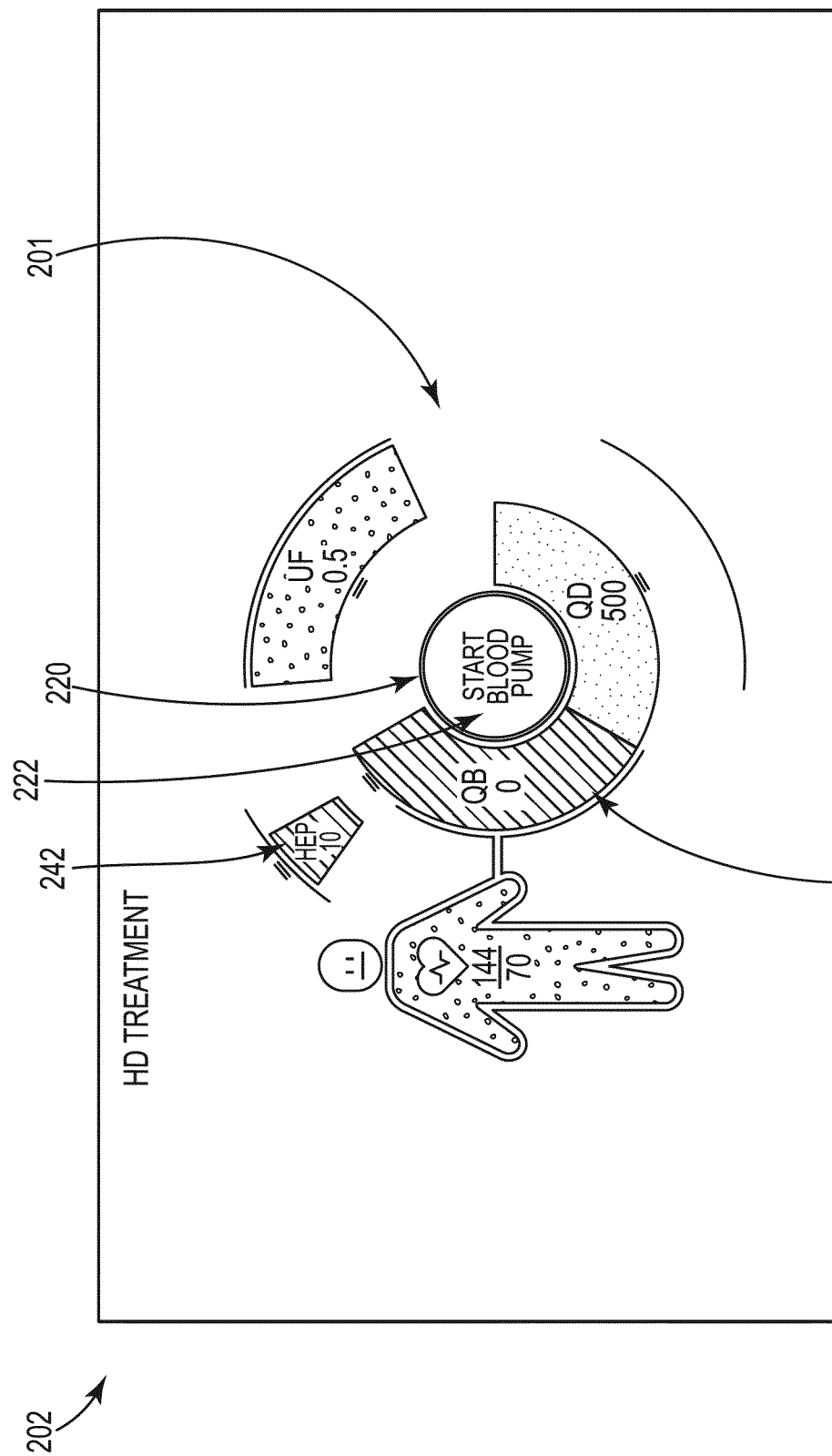

After blood has filled the circuit as shown in FIG. 4D, the alphanumeric indication 222 of the primary region 220 may include the text "START Blood Pump," which indicates to a user that the blood pump may be started to begin the treatment, e.g., by selecting the primary region 220. Additionally, the primary region 220 may be graphically animated (e.g., flashing, highlighted, pulsing, etc.) to indicate to a user that the blood pump may be started to begin treatment, e.g., by selecting the primary region 220.

Further, an anticoagulation process feature graphical element 242 may be further depicted in the operation region 201 that may be associated with and representative of the anticoagulation provided by the treatment system. Similar to other process feature graphical elements described herein, the anticoagulation process feature graphical element 242 may be moved proximate another process feature graphical element, such as the blood process feature graphical element 212 to indicate the delivery of anticoagulation to the blood circuit. In this example, the anticoagulation process feature graphical element 242 represents and is associated with heparin. In other embodiments, one or more process feature graphical elements similar to the anticoagulation process feature graphical element 242 may be associated with and representative of other process features such as, e.g., natrium/sodium profiling proximate to the dialysate process feature graphical element 214, ultrafiltration profiling proximate to the ultrafiltration process feature graphical element 216, etc.

In one or more embodiments, process feature graphical elements such as the anticoagulation process feature graphical element 242 may be referred to as secondary process feature graphical elements because, e.g., such process feature graphical elements may not contribute to the formation, or completion, of a user-recognizable form. Instead, it may be described that the secondary process feature graphical element may be "clipped" or "attached" to another process feature graphical element that contributes to, or may be part of, a user-recognizable form. Further, the secondary process feature graphical element may affect one or more parameters and/or processes associated with and represented by the process feature graphical element the secondary process feature graphical element is attached. For example, the anticoagulation process feature graphical element 242 may be coupled to the blood process feature graphical element 212, and thus, may provide one or more process features that have at least some effect on the processes associated with and represented by the blood process feature graphical element 212. Still further, the secondary process feature graphical element may be described as being tied to, or "running with," the process feature graphical element it is coupled to. In other words, the secondary process feature graphical element may behave and be interacted with in the same way as the process feature graphical element it is coupled to. For example, if a process feature graphical element is activated or deactivated (e.g., by selecting-and-moving it away or proximate to another graphical element), an attached secondary process feature graphical element may also be activated or deactivated, respectively. For example, if the blood process feature graphical element 212 is moved away from the primary region 220 and/or other process feature graphical elements, the anticoagulation process feature graphical element 242 may remain coupled to the blood process feature graphical element 212 and move with the blood process feature graphical element 212 away from the primary region 220 and/or other process feature graphical elements, which may affect the one or more processes associated with anticoagulation process feature graphical element 242 (e.g., deactivate anticoagulation processes, etc.). In this way, a user may only need to select-and-drag the blood process feature graphical element 212 to simultaneously affect the anticoagulation process feature graphical element 242.

Figure 4E:
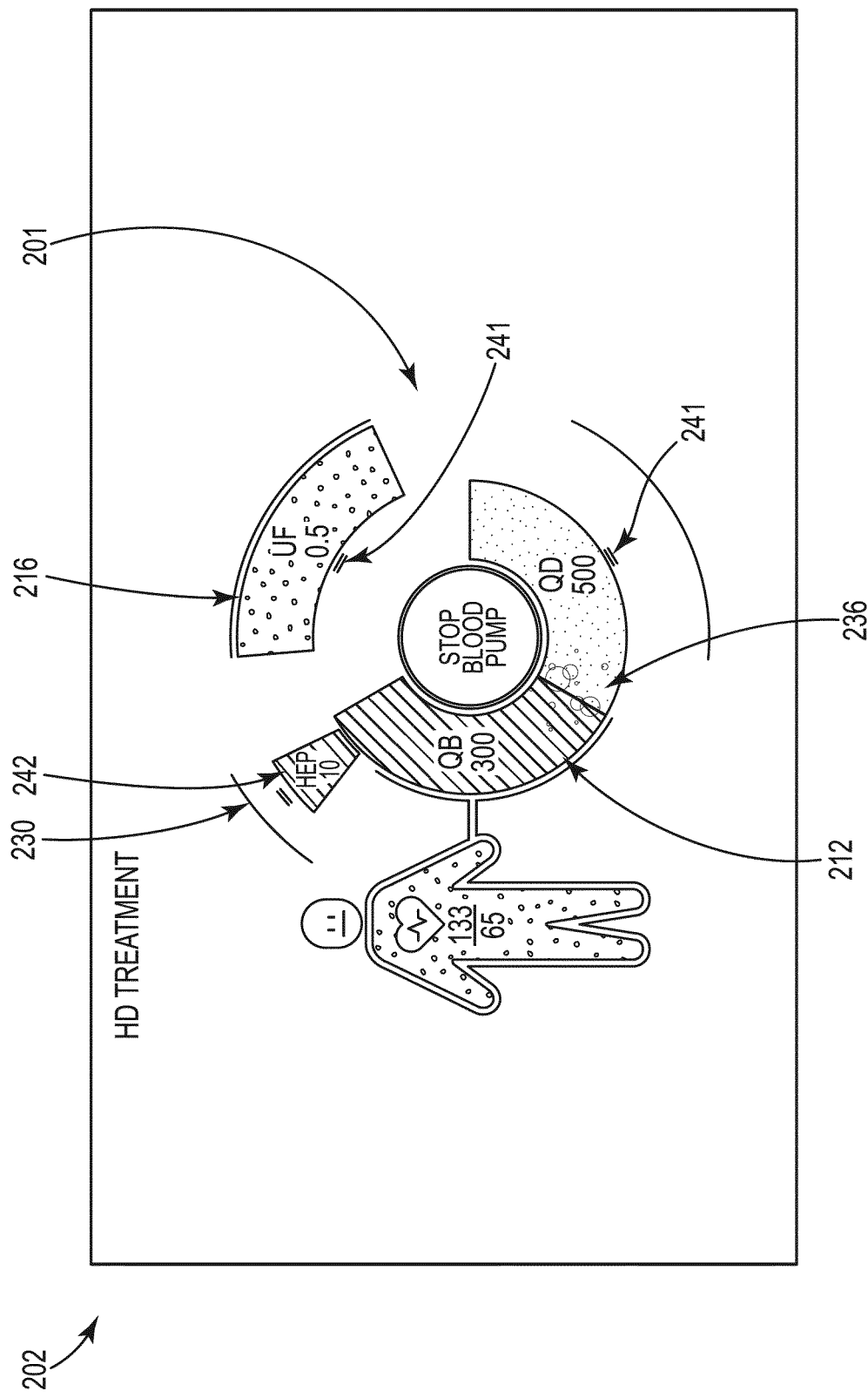

As shown in FIG. 4E, the anticoagulation process feature graphical element 242 has been moved proximate the blood process feature graphical element 212 to, e.g., indicate that the anticoagulation is being delivered into the blood circuit, indicate that the anticoagulation is coupled to the blood circuit and ready for delivery into blood circuit, etc. Similar to other process feature graphical elements, the anticoagulation process feature graphical element 242 may be moved by a user to indicate that the anticoagulation should begin or that the anticoagulation is coupled to the system, or may be moved automatically by the system in response to the anticoagulation being connected to the blood circuit. Further, similar to other process feature graphical elements, an affordance indication 230 may be depicted indicating where the anticoagulation process feature graphical element 242 has been moved from when in the inactive state to indicate to a user that the anticoagulation process feature graphical element 242 may be moved back to the previous location proximate the affordance indication 230 (to, e.g., move the anticoagulation process feature graphical element 242 back to an inactive state). In one or more embodiments, when process feature graphical elements and the process features associated therewith are deactivated, or configured in an inactive state, the process feature graphical elements may be graphically animated, e.g., by flashing, highlighting, etc., to signal to a user that such process features are currently in a deactivated state.

Further, the blood pump has been started in FIG. 4E and a fluidic animation 236 may be displayed in the blood process feature graphical element 212 and the dialysate process feature graphical element 214 to indicate that flow is occurring in each of the blood circuit and the dialysate circuit of the treatment system.

In at least the embodiment depicted herein, movement indicators, or affordances, 241 may be displayed proximate the process feature graphical elements to indicate that the process feature graphical elements may be moved and the direction where such process feature graphical elements may be moved. The movement indicators 241 as shown are a pair of short parallel lines located, or depicted, on the side of the process feature graphical element where it may be moved to. For example, a movement indicator 241 is shown proximate the dialysate process feature graphical element 214 to indicate that it may be moved away from the primary graphical region 220 and/or other process feature graphical elements such as blood process feature graphical element 212. Likewise the movement indicator 241 proximate the dialysate process feature graphical element 214 is not located between the dialysate process feature graphical element 214 and the primary graphical region 220 and the blood process feature graphical element 212. Conversely, for example, a movement indicator 241 is shown proximate the ultrafiltration process feature graphical element 216 to indicate that it may be moved towards and proximate the primary graphical region 220 and/or the other process feature graphical elements 212, 214. Likewise the movement indicator 241 proximate the ultrafiltration process feature graphical element 216 is generally located between the ultrafiltration process feature graphical element 216 and the primary graphical region 220 and the other process feature graphical elements 212, 214.

Figure 4F:
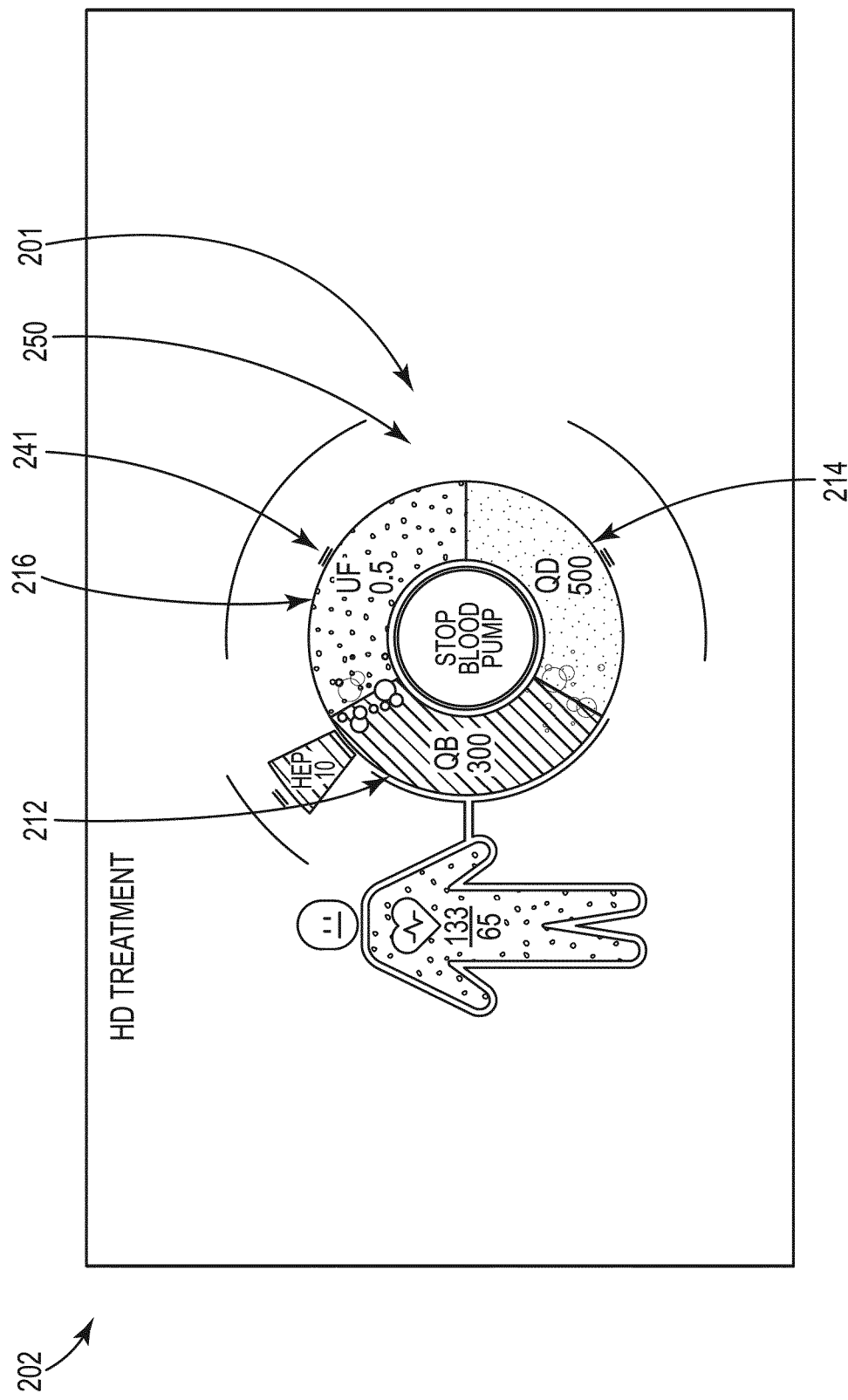

To begin ultrafiltration, the ultrafiltration process feature graphical element 216 may be moved proximate the primary region 220 as shown in FIG. 4F. It may be described that the ultrafiltration process feature graphical element 216 may be moved proximate the blood process feature graphical element 212 and the dialysate process feature graphical element 214 to complete the user-recognizable form, or shape, 250, which in this example is a circle. Completion of the user-recognizable form 250 may indicate to a user that a prescription for the blood treatment therapy is complete. Further, completion of the user-recognizable form 250 may indicate to a user that no more processes or steps need to be performed until to completion of treatment (e.g., the completion of the user-recognizable form 250 may indicate that all of the processes or steps for the prescribed treatment have been completed). Further, when the graphical user interface includes one or more secondary process feature graphical elements, the complete prescription may not be completed until the one or more secondary process feature graphical elements are also moved proximate the user-recognizable form 250 (e.g., even if the secondary process feature graphical elements do not form part of the user-recognizable form 250). Additionally, a movement indicator 241 is now shown proximate the ultrafiltration process feature graphical element 216 to indicate that it may be moved away from the primary graphical region 220 and/or other process feature graphical elements such as blood process feature graphical element 212 and dialysate process feature graphical element 214.

Figure 4G:
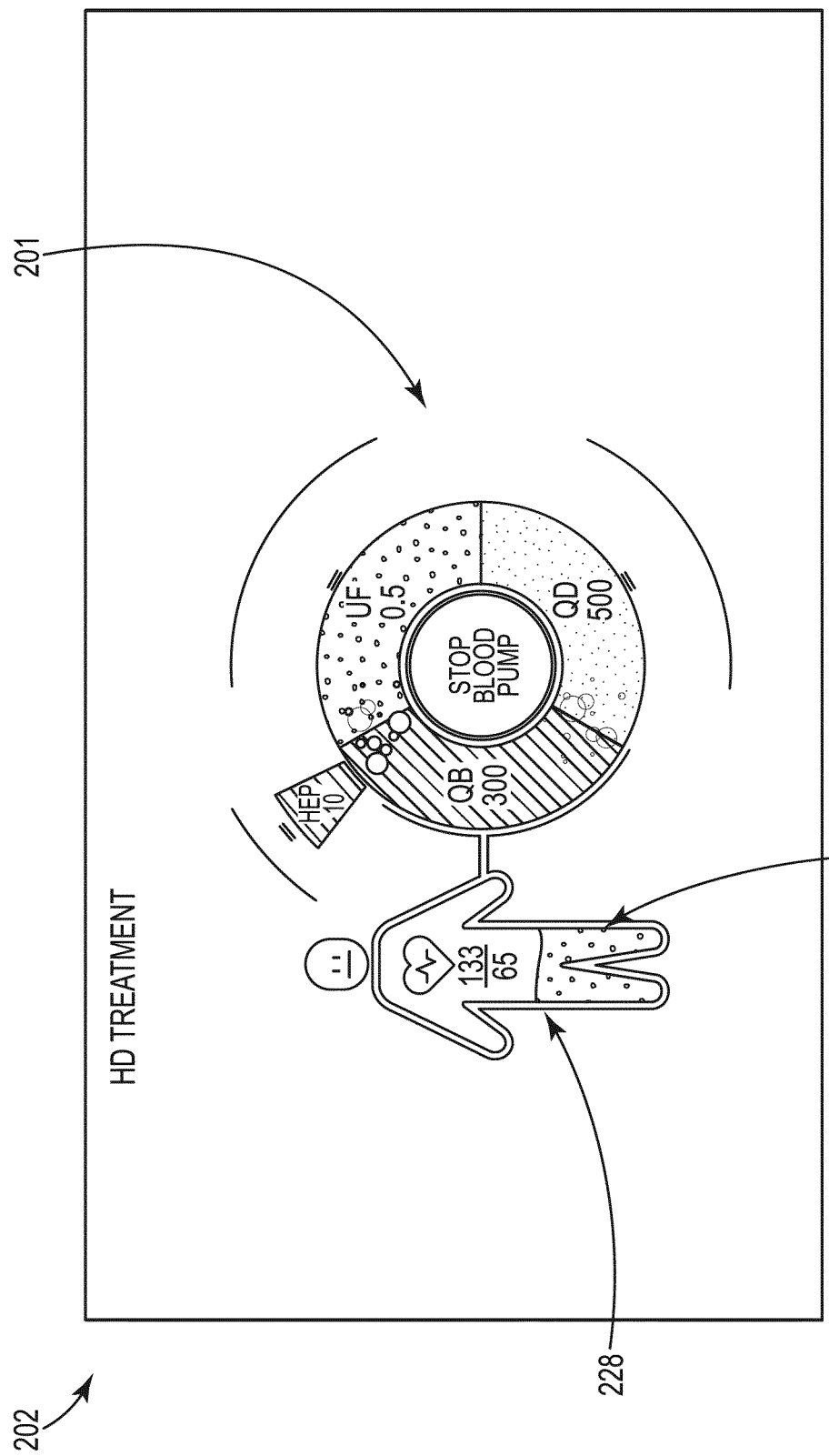

As treatment continues, waste may be removed from the patient as indicated by the waste graphical indicia 228 of the human-shaped process feature graphical element 218 as shown in FIG. 4G. More specifically, at least some of the fill color representing the waste within the human outline may have disappeared. Further, it may be described that the waste graphical indicia 228, e.g., the fill color, defines a waste fluid level line, e.g., symbolically representing a fluid level of the waste left in a waste-filled container. In other words, the waste may be shown to be partially removed by the graphical indicia 228 in the human-shaped process feature graphical element 218 of FIG. 4G. Also, a fluidic animation 236 may be displayed in the blood process feature graphical element 212 and the ultrafiltration process feature graphical element 216 to indicate that flow is occurring in the blood circuit and the ultrafiltration apparatus.

Figure 4H:
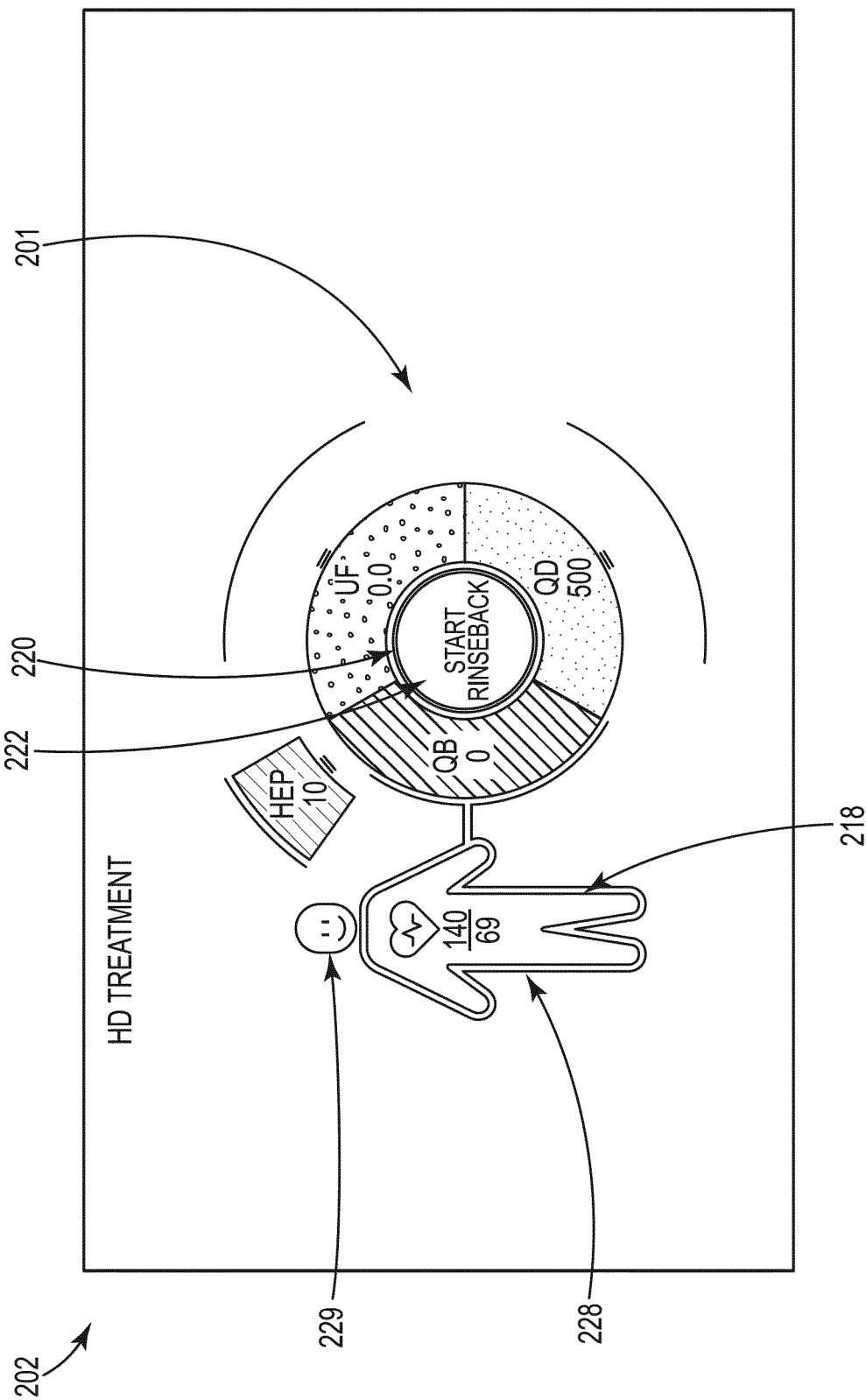

After the treatment is completed, the waste graphical indicia 228 of the human-shaped process feature graphical element 218 may indicate that all, or at least a selected value of, waste has been removed from the patient and the graphical facial expression 229 of the human-shaped process feature graphical element 218 may be configured to show happiness to indicate that extracorporeal blood treatment is complete and that the patient disconnection procedures including rinseback may begin as shown in FIG. 4H. To begin rinseback, as user may select the primary region 220, which may include the alphanumeric indication 222, "START Rinseback" and/or be graphically animated.

Figure 4I:
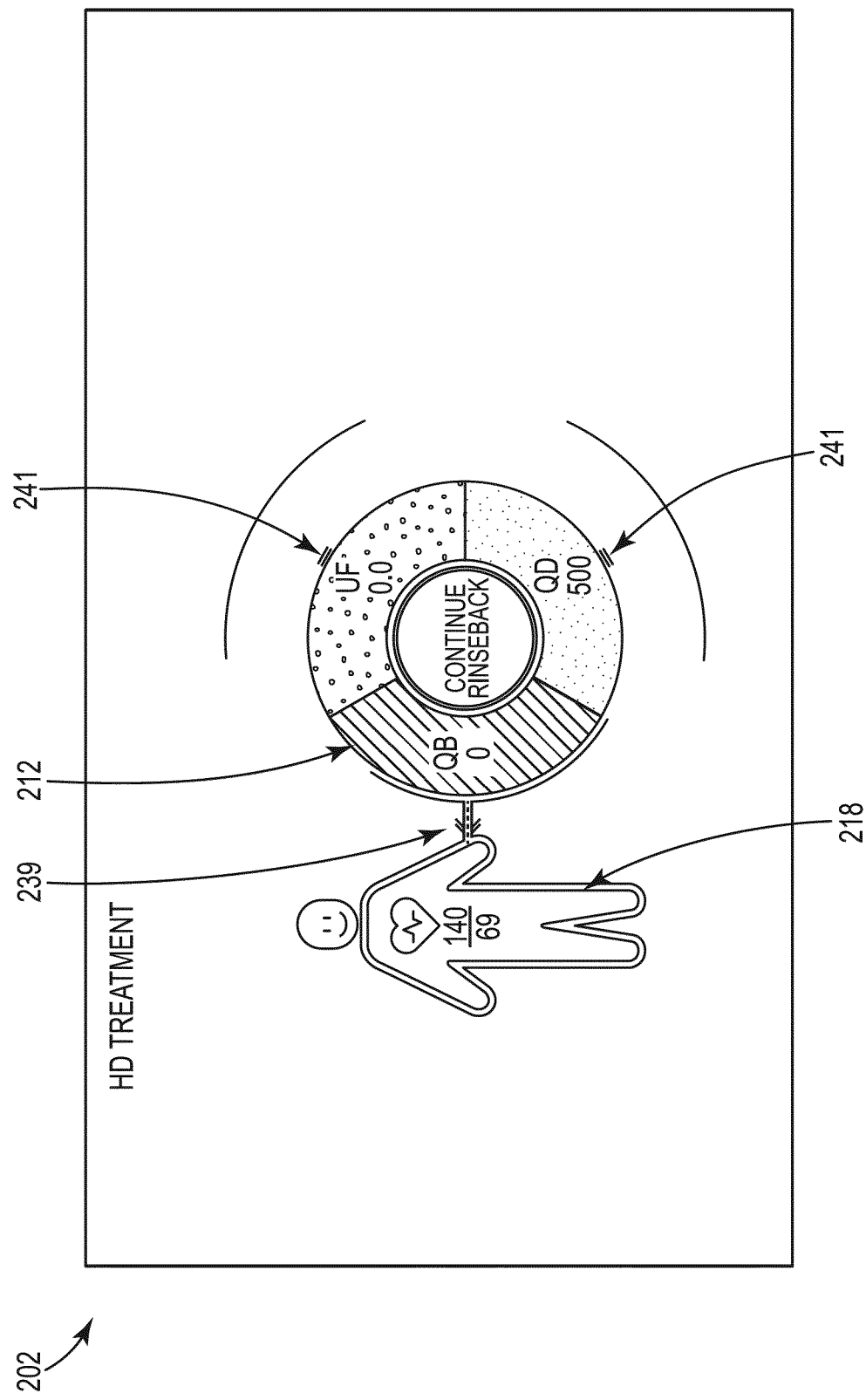
Figure 4J:
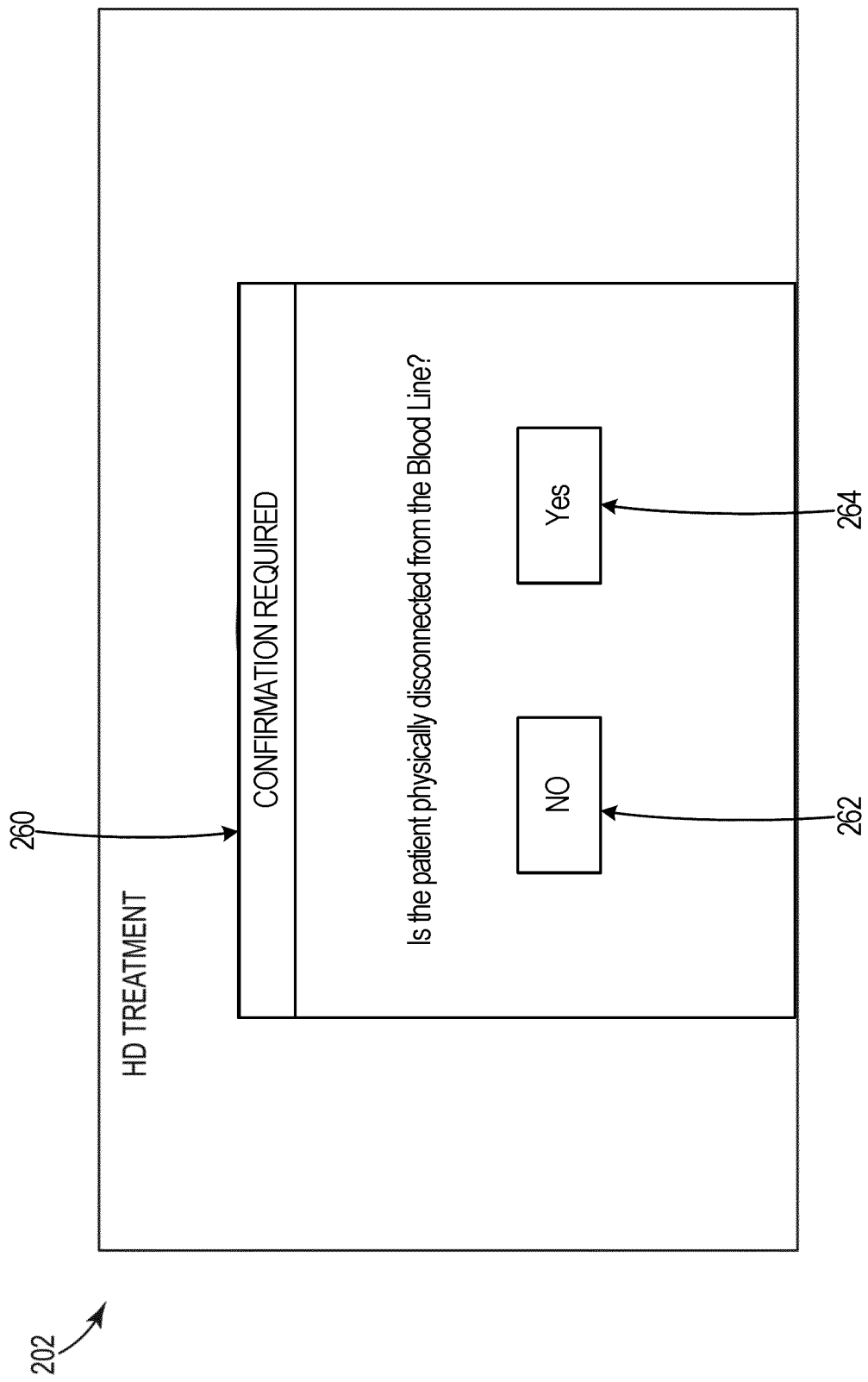

After rinseback is complete, a patient disconnection affordance 239 as shown in FIG. 4I may be provided extending between the blood process feature graphical element 212 and the human-shaped process feature graphical element 218 to, e.g., indicate that the next step, or task, may be to physically disconnect the patient from the treatment system. The human-shaped process feature graphical element 218 may automatically be moved away from the blood process feature graphical element 212 upon physical disconnection of the patient from the blood circuit (e.g., one or more sensors or other apparatus of the treatment system may determine that the patient has been physically disconnected to the blood circuit) and/or a user may move the human-shaped process feature graphical element 218 away from the blood process feature graphical element 212 after physical disconnection of the patient from the blood circuit to indicate that the patient is properly physically disconnected from the blood circuit after treatment. Additionally, although not depicted, a fluidic progress bar may be displayed in the blood process feature graphical element 212 to indicate progression of the rinseback of the blood circuit. Further, as shown in FIG. 4J, one or more confirmation graphical regions or areas may be presented during the disconnection process. For example, if a user had selected the human-shaped process feature graphical element 218 and moved, or dragged, the human-shaped process feature graphical element 218 away from the blood process feature graphical element 212, a confirmation graphical region 260 may be displayed, or depicted, to confirm that the patient is actually, physically, disconnected. The confirmation graphical region 260 may include a query asking the user whether the patient is physically disconnected from the blood circuit. The confirmation graphical region 260 may further allow a user to answer affirmatively or negatively to the query. In the embodiment shown, to confirm that the patient is actually, physically, disconnected, a user may select an area or element of the confirmation region. For example, a user may select a "NO" graphical area 262 to indicate to the treatment system that the patient is not physically disconnected from the blood line, which in turn, will remove the confirmation graphical region 260 from the graphical user interface 202 returning to the graphical user interface 202 shown in FIG. 4I with the human-shaped process feature graphical 218 proximate the blood process feature graphical element 212. In other words, in response to the user answering the query negatively, the human-shaped graphical element may be moved (back to being) proximate the blood process feature graphical element 212). Conversely, for example, a user may select a "YES" graphical area 264 to indicate to the treatment system that the patient is physically disconnected from the blood line, which in turn, will also remove the confirmation graphical region 260 from the graphical user interface 202 but with the human-shaped process feature graphical 218 moved away from the blood process feature graphical element 212 as shown in FIG. 5A. After a patient has been disconnected, the sensors of the treatment system should not detect blood in the blood circuit.

In one or more embodiments, the human-shaped process feature graphical element 218 may be integrated with or in proximity to a blood pressure graphical representation 221 associated with the a connection outline 240 including blood lines as shown in FIG. 4K between the process feature graphical elements 212, 214, 216 and the primary region 220 and the human-shaped process feature graphical element 218. The blood pressure graphical representation 221 may include a graphical and numerical representation of each of venous and arterial blood pressure, each proximate (e.g., adjacent, extending therefrom, next to, etc.) to the respectively-related venous and arterial blood line. The graphical representations of the venous and arterial blood pressure may include historical graphs of pressures measured, or monitored, in the venous and arterial blood lines, respectively, from a selected point in the past (e.g., 1 minute previously, 1 minutes previously, 10 minutes previously, etc.) to the present time. The numerical representations of the venous and arterial blood pressure may be the present pressures measured, or monitored, in the venous and arterial blood lines, respectively.

Additionally, as shown in the embodiment in FIG. 4K, the primary region 220 may include a graphical representation of a pump, which may indicate when the pump is active (e.g., pumping, running, etc.) or inactive (e.g., not pumping, not running, etc.). As shown, the graphical representation of a pump in the primary region 220 includes two dots, or spots, configured to represent a peristaltic pump such as a the blood pump. When the pump is active, the two dots, or spots, may rotate, or orbit, about the center of the circle of the primary region 220 as indicated by the arrows. When the pump is inactive, the two dots, or spots, may be stationary or may not be shown. Additionally, although not shown, it is be understood that the graphical representation of the pump may be shown, or depicted with, or in conjunction, with the alphanumeric indication 222 of the primary region 220.

Figure 5B:
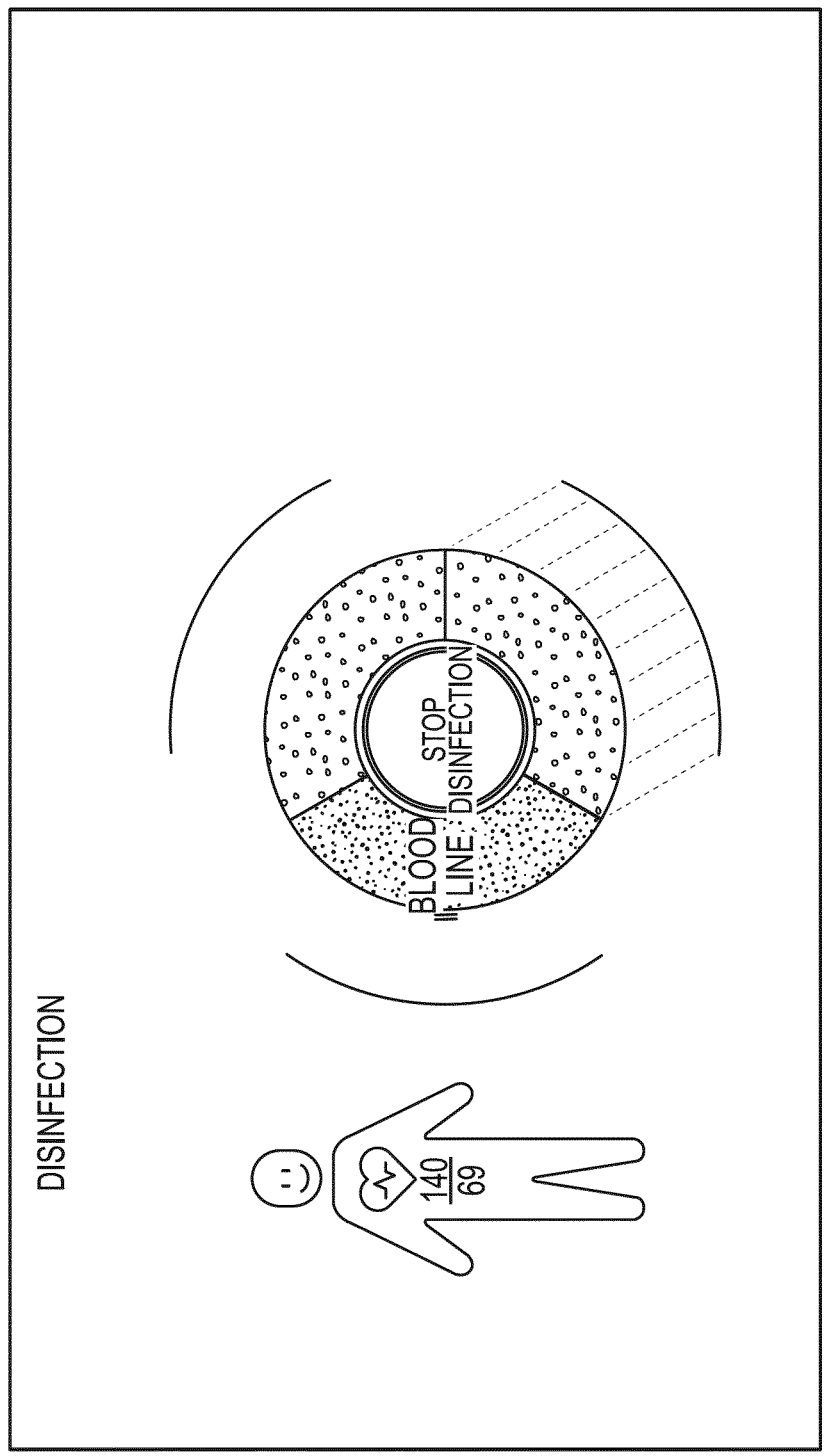
Figure 6:
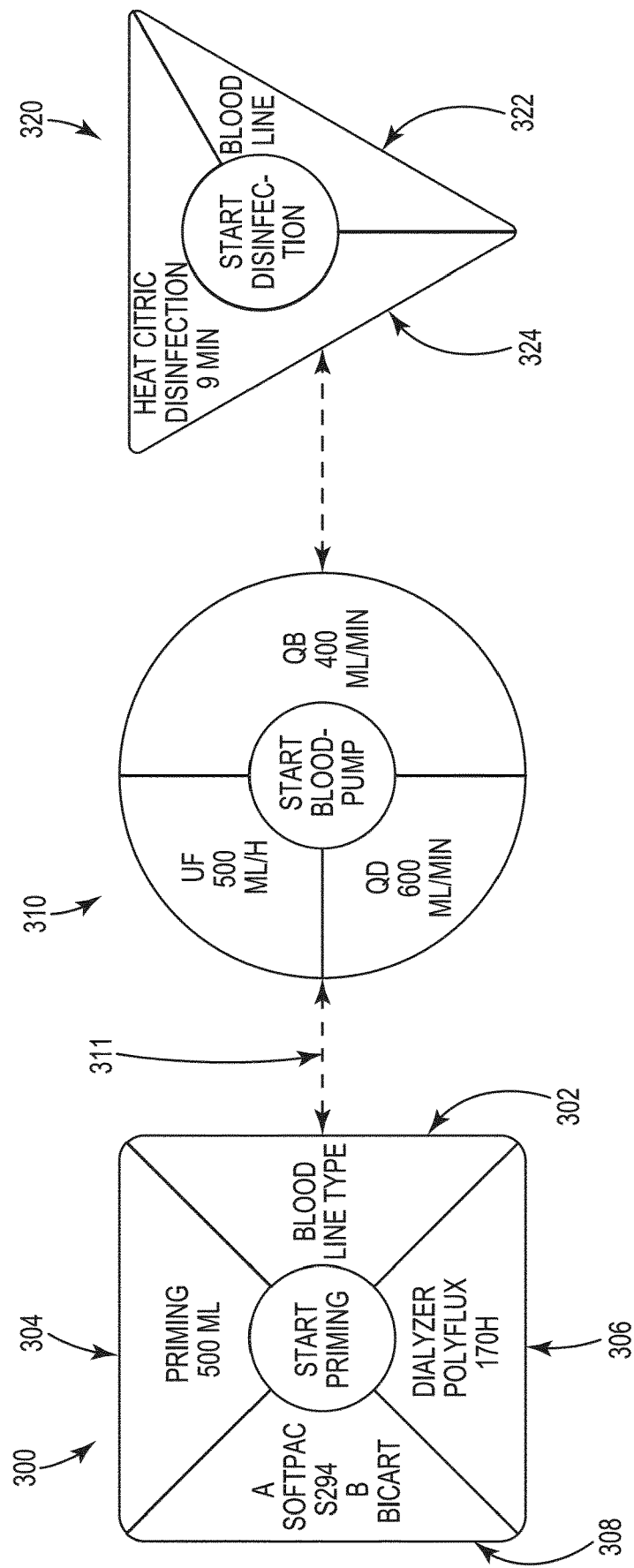
FIG. 6 depicts exemplary process feature graphical elements and user-recognizable forms, or shapes, for use an exemplary graphical user interfaces such as, for example, shown in FIGS. 3-5.

After the rinseback is complete and the patient is disconnected from the treatment system, post-treatment processes using the exemplary graphical user interface 204 of the extracorporeal blood treatment system may be performed such as "disinfection" as shown in FIGS. 5A-5B. Similar to the exemplary graphical user interfaces 200, 202 described herein, the exemplary graphical user interface 204 may include a plurality of process feature graphical elements 212, 214, 216 and a primary region 220.

As shown in FIG. 5A, the dialysate process feature graphical element 214 is shown located away from the primary region 220 and away from the blood circuit and ultrafiltration process feature graphical elements 212, 216 to, e.g., indicate that the dialysate circuit is not connected to blood treatment system and/or blood circuit and ultrafiltration apparatus. Further, the alphanumeric indication 222 of the primary region 220 recites "START Disinfection," which indicates that the disinfection process will start upon user selection of the primary region 220.

In FIG. 5B, the dialysate process feature graphical element 214 is shown proximate the primary region 220 and the blood circuit and ultrafiltration process feature graphical elements 212, 216 to, e.g., indicate that the dialysate circuit is connected to blood treatment system and/or blood circuit and ultrafiltration apparatus. Further, the disinfection process is being performed as may be indicated by changes to the process feature graphical elements 214, 216 (e.g., color changes, highlighting, etc.).

As described herein, the exemplary process feature graphical elements may form a user-recognizable form, or shape, when the process feature graphical elements are located proximate each other such as, e.g., a circle, square, triangle, rectangle, line, hexagon, and/or any other clearly recognizable shape. The user-recognizable form may be the same for each different overall, or primary, process represented by the user-recognizable form. For example, in FIGS. 3-5, the user-recognizable form is a circle for the setup and priming process depicted in FIGS. 3A-3F, the blood treatment process depicted in FIGS. 4A-4L, and the disinfection process depicted in FIGS. 5A-5B. In other embodiments, the user-recognizable form may be different for each different overall, or primary, process represented by the user-recognizable form. For example, three different user-recognizable forms 300, 310, 320 representative of three different overall, or primary, processes are depicted in FIG. 6. More specifically, the user-recognizable form 300 corresponding to a setup and priming process is a square, the user-recognizable form 310 corresponding to a blood treatment process is a circle, and the user-recognizable form 320 corresponding to a post-treatment process is a triangle.

In at least one embodiment, each of the user-recognizable forms 300, 310, 320 may be displayed in an operation region of an exemplary graphical user interface one-at-a-time. Further, the displayed user-recognizable forms 300, 310, 320 may be selected by a user. For example, if the user-recognizable form 300 for setup and priming is displayed and a user would like the user-recognizable form 310 for blood treatment to be displayed, a user may perform a swipe, or swiping, gesture 311 across a portion of the graphical user interface (e.g., touchscreen) to display the user-recognizable form 310 for blood treatment.

The user-recognizable form 300 associated with and representative of setup and priming includes four setup/priming process feature graphical elements. More specifically, the user-recognizable form 300 may include a blood process feature graphical element 302 (e.g., representative of and associated with the blood line), a priming process feature graphical element 304, a setup process feature graphical element 306 (e.g., representative of and associated with the dialyzer/filter), and a concentrate/cartridge process feature graphical element 308 (e.g., representative of and associated with a concentrate and/or cartridge to be used in priming and/or therapy). The blood process feature graphical element 302 may be at least partially similar to the blood process feature graphical element 212 and the concentrate/cartridge process feature graphical element 308 may be at least partially similar to the dialysate process feature graphical element 214 described herein with respect to FIGS. 3-5

The user-recognizable form or shape 310 may be similar to the user-recognizable form 250 described herein with respect to FIGS. 3-5. The user-recognizable form 320 associated with and representative of disinfection includes two process feature graphical elements. The blood process feature graphical element 322 may be at least partially similar to the blood process feature graphical element 212 described herein with respect to FIGS. 3-5. The heat citric disinfection process feature graphical element 324 may be associated with and representative of disinfection fluid used in the disinfection process.

Figure 7A:
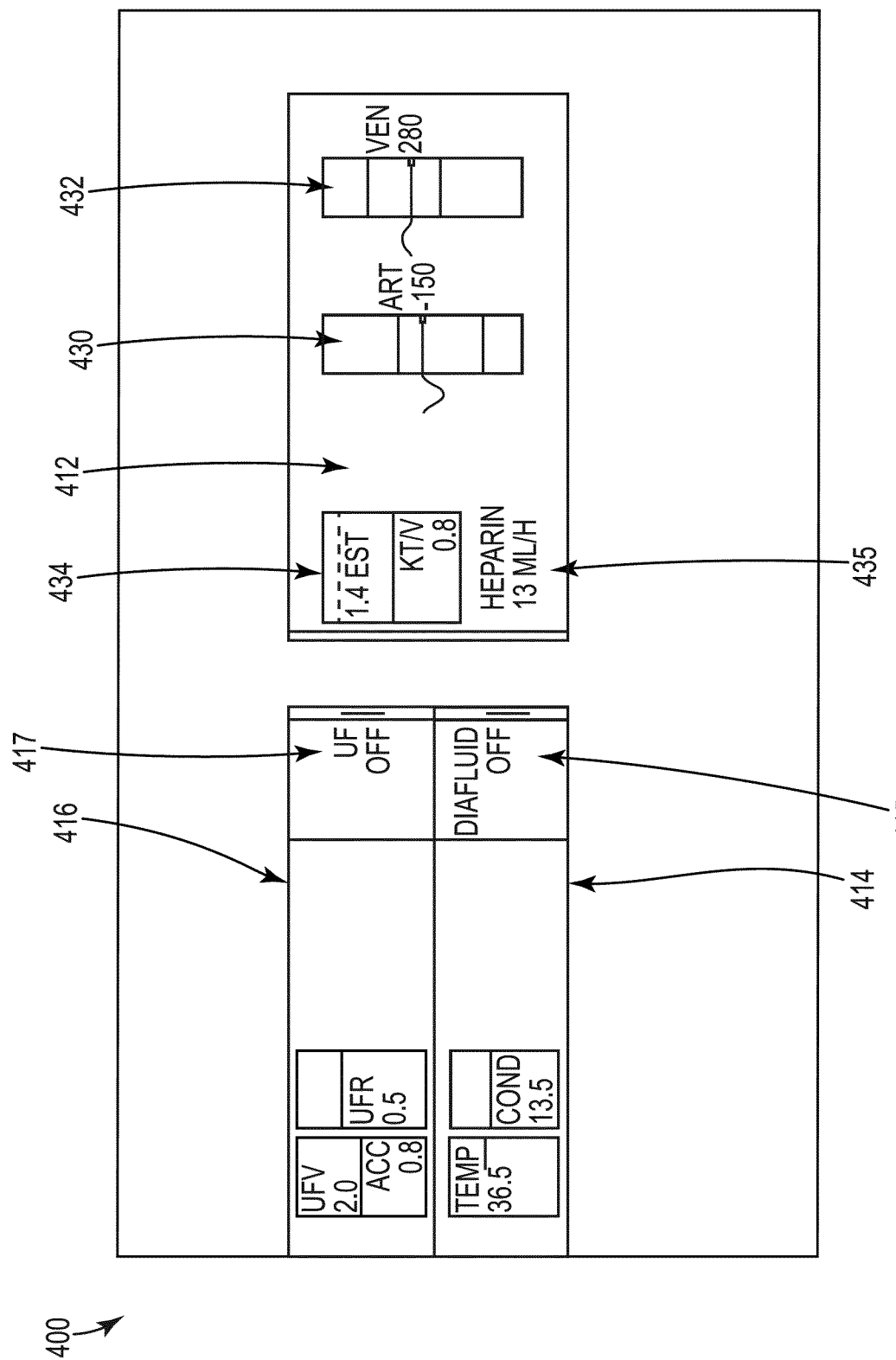
FIGS. 7A-7C depict an exemplary graphical user interface for use in performing a treatment using an extracorporeal blood treatment system such as, for example, shown generally in FIGS. 1-2.
Figure 7B:
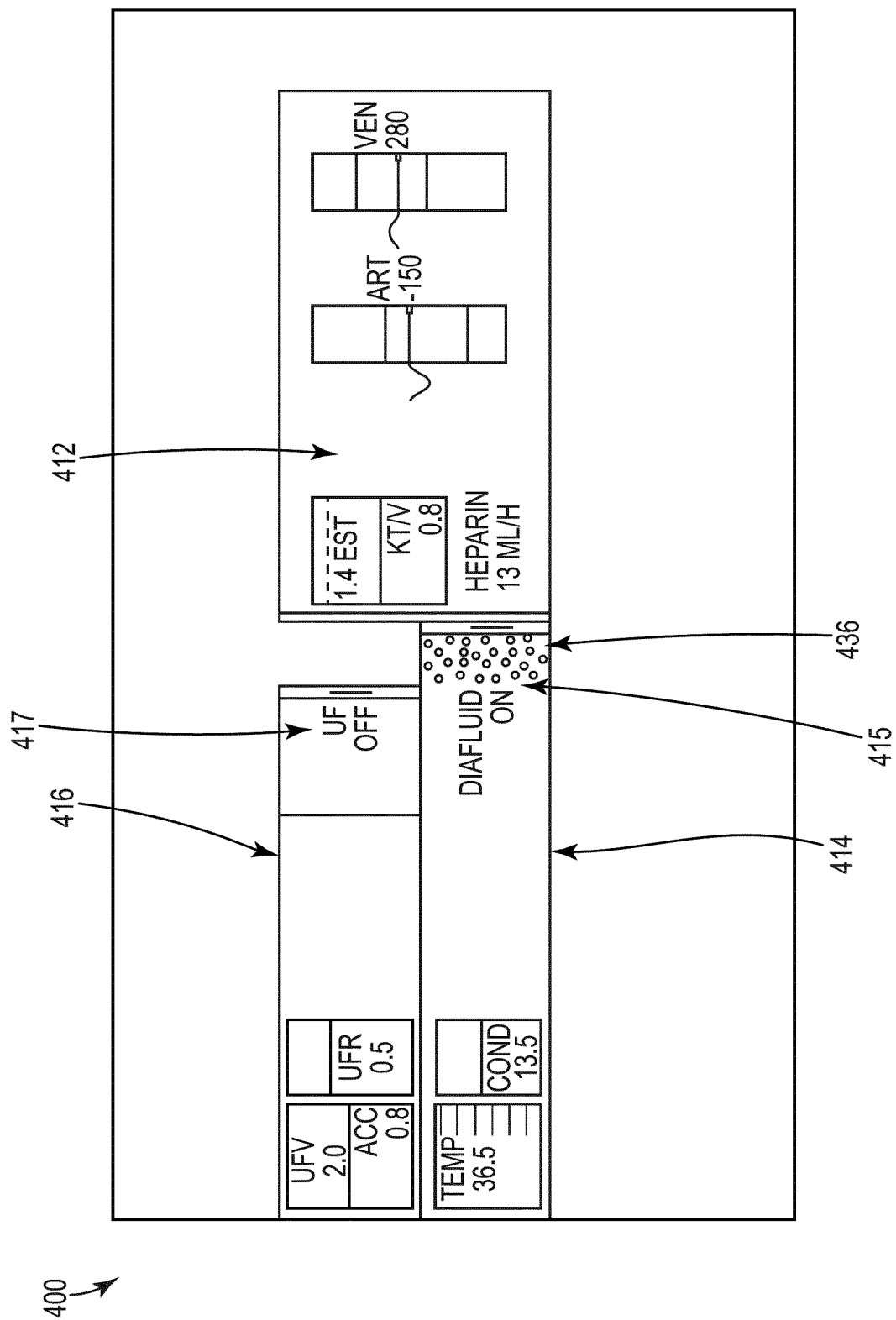
Figure 7C:
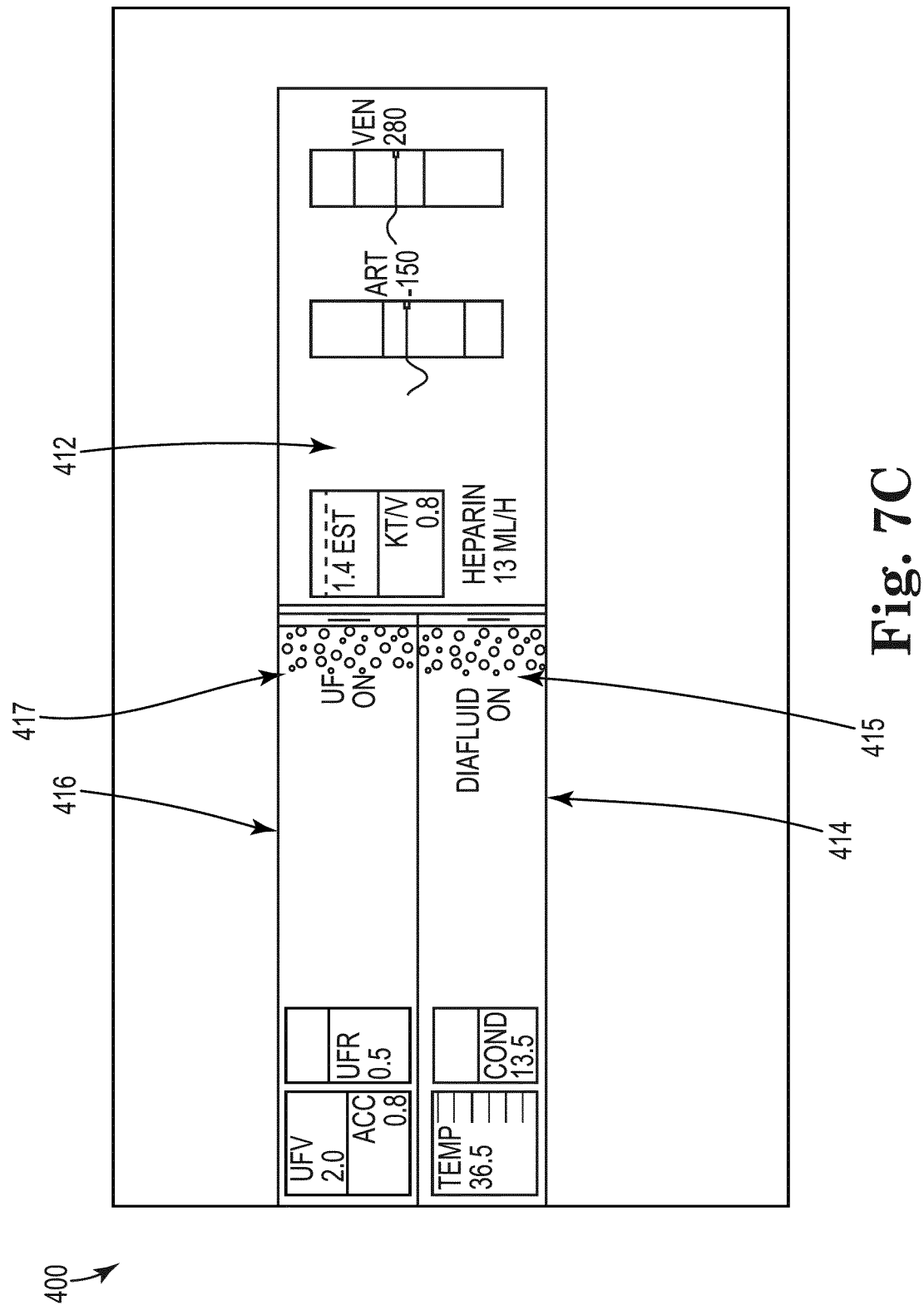

Another exemplary graphical user interface 400 for use in performing a treatment using an extracorporeal blood treatment system is depicted in FIGS. 7A-7C. The graphical user interface 400 may include a plurality of process feature graphical elements such as a blood process feature graphical element 412, a dialysate process feature graphical element 414, and an ultrafiltration process feature graphical element 416. To change a state associated with a process feature of the dialysate process feature graphical element 414, the dialysate process feature graphical element 414 may be moved (e.g., by dragging towards, etc.) proximate to the blood process feature graphical element 412 as shown in FIG. 7B.

In this example, rather than the entire dialysate process feature graphical element 414 being moved proximate the blood process feature graphical element 412, an end portion 415 of the dialysate process feature graphical element 414 may be moved proximate the blood process feature graphical element 412. In other words, the end portion 415 may be moved towards and proximate the blood process feature graphical element 412 to extend the dialysate process feature graphical element 414 into contact with, overlapping with, or in close proximity to the blood process feature graphical element 412. The end portion 415 may be similar to the connection areas 270, 272 described herein with reference to FIGS. 3A-3B, and the blood process feature graphical element 412 may further define a connection area similar to the connection areas 270, 272 described herein with reference to FIGS. 3A-3B. The end portion 415, or connection area, of the dialysate process feature graphical element 414 may be moved proximate (e.g., overlapping, touching, contacting, closer to, etc.) the connection area of the blood process feature graphical element 412 to, e.g., indicate a change in a state of the dialysate process feature graphical element 414 and/or the blood process feature graphical element 412.

The dialysate process feature graphical element 414 being moved proximate to the blood process feature graphical element 412 may indicate completion of the fluid coupling of the dialysate circuit and the blood circuit. Further, as described herein, a fluidic animation 436 may be displayed in the dialysate process feature graphical element 414 as shown in FIG. 7B after such fluid coupling. The fluidic animation 236 may include graphical representations of a flow of particles such as bubbles and/or fluid particles exchanging, or moving, in the end portion 415 of the dialysate process feature graphical element 414 proximate the blood process feature graphical element 412.

The ultrafiltration process feature graphical element 416 may include similar functionality to the dialysate process feature graphical element 414. For example, as shown in FIG. 7C, the ultrafiltration process feature graphical element 416 may include an end portion 417 configured to be moved proximate the blood process feature graphical element 412 to indicate the performance of ultrafiltration in a treatment.

In this example, the blood process feature graphical element 412 may be defined or described as a graphical region of the graphical user interface 400. Further, the blood process feature graphical element 412 may be described as a stationary graphical region (e.g., a region that does not, or is not allowed to, move). The blood process feature graphical element 412 may include, or display, multiple blood-related parameters and/or settings. For example, as shown, the blood process feature graphical element 412 includes an arterial pressure feature 430 for displaying the current and past arterial pressure of the patient, a venous pressure feature 432 for displaying the current and past venous pressure of the patient, a treatment adequacy parameter feature 434 for displaying the adequacy of the treatment (e.g., Kt/v), and an anticoagulation delivery feature 435 for displaying the anticoagulation type (e.g., heparin) and delivery rate (e.g., 13 ml/h).

In one or more embodiments, the process feature graphical elements may be configured to overlap each other when moved proximate one another as shown in another exemplary graphical user interface 500 for use in an extracorporeal blood treatment system as depicted in FIGS. 8A-8F.

Figure 8A:
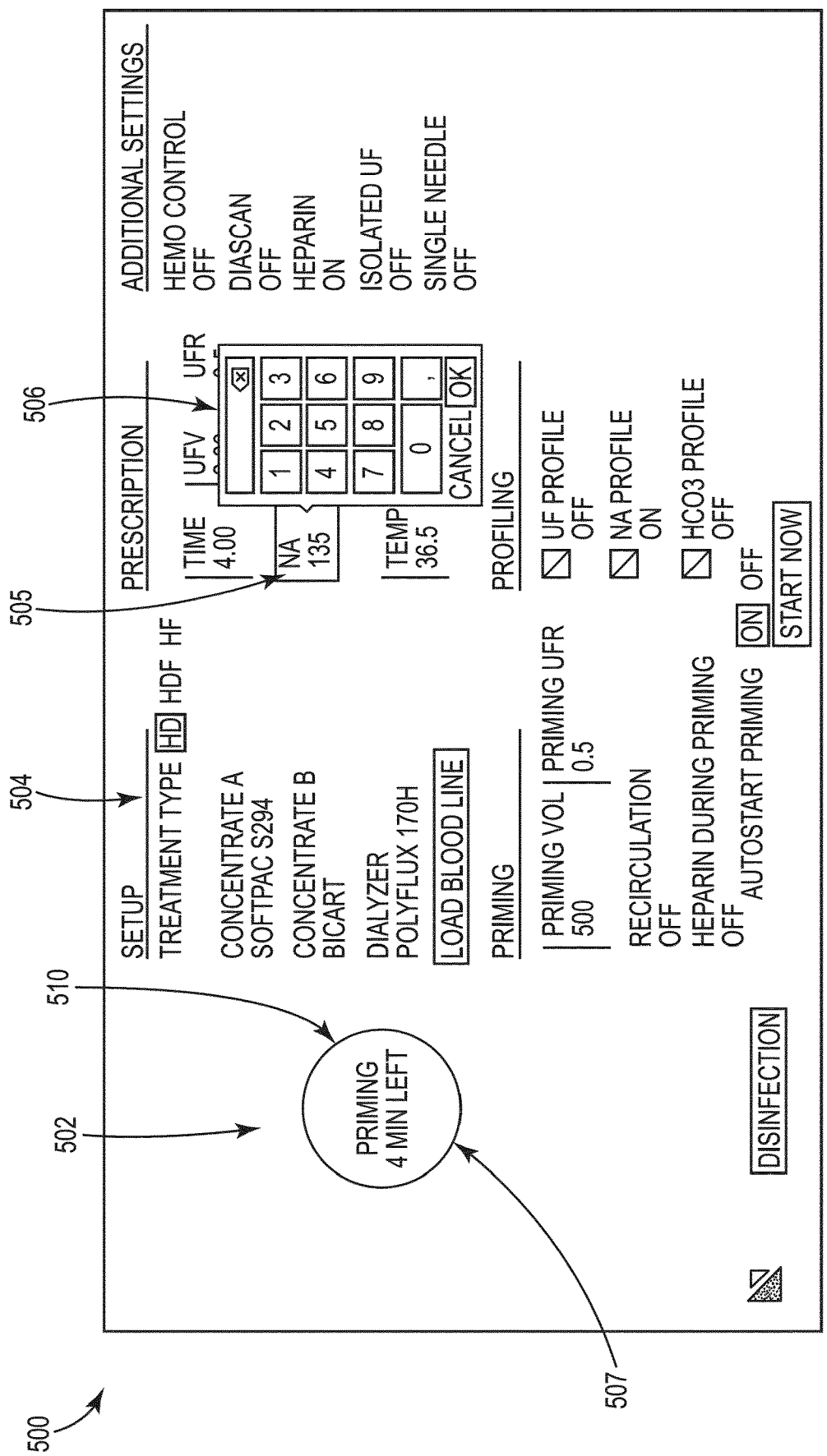
FIGS. 8A-8F depict an exemplary graphical user interface for use in preparing and performing a treatment using an extracorporeal blood treatment system such as, for example, shown generally in FIGS. 1-2.

As shown, the exemplary graphical user interface 500 may include an operation region 502 and a settings region 504. The operation region 502 may include one or more process feature graphical elements. As shown in FIG. 8A, the graphical user interface 500 is configured in a priming mode, and as such, the operation region 502 includes a priming process feature graphical element 510 corresponding to priming a fluid circuit of a treatment system. The priming process feature graphical element 510 further includes the alphanumeric text, "Priming" and "4 min left" to indicate to a user that the system is priming and that an estimated time to completion of the priming process is 4 minutes. Further, a circumferential indicator 507 may located about the circumference of the priming process feature graphical element 510 to, e.g., graphically indicate the progression of the priming process (e.g., the circumference of the priming process feature graphical element 510 may represent 100% of the priming process and the circumferential indicator 507 may indicate where along the circumference the priming process is presently at).

Further, the settings region 504 may include, or display, a plurality of settings and/or parameters related to priming. Some of the settings and parameters may be selectable by a user to change the settings or parameters. For example, a user has selected the sodium treatment parameter 505 in FIG. 8A, and thus, a parameter selection element 506 has been displayed that is configured to allow the user to change the value for the sodium treatment parameter 505.

Figure 8B:
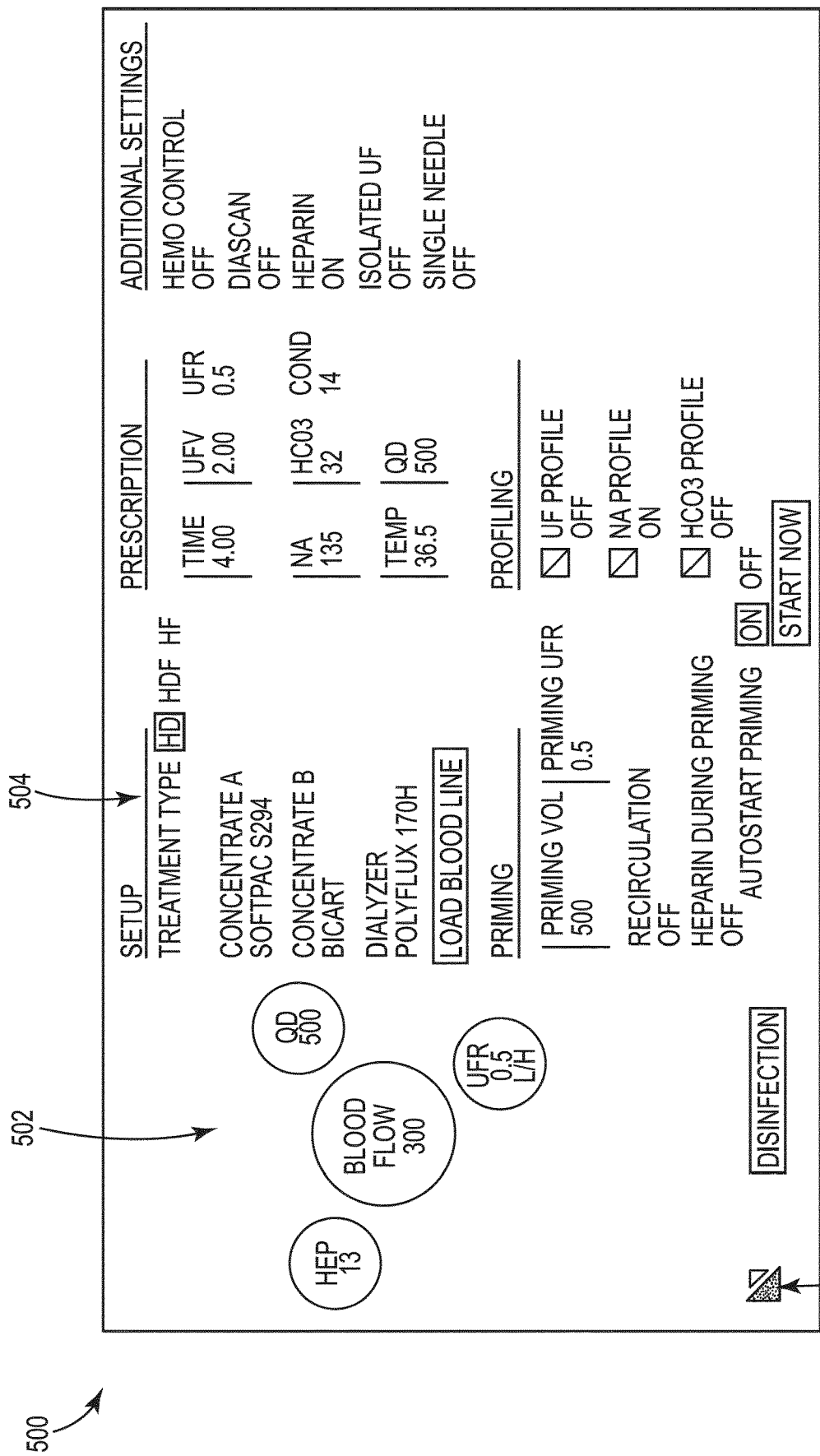
Figure 8C:
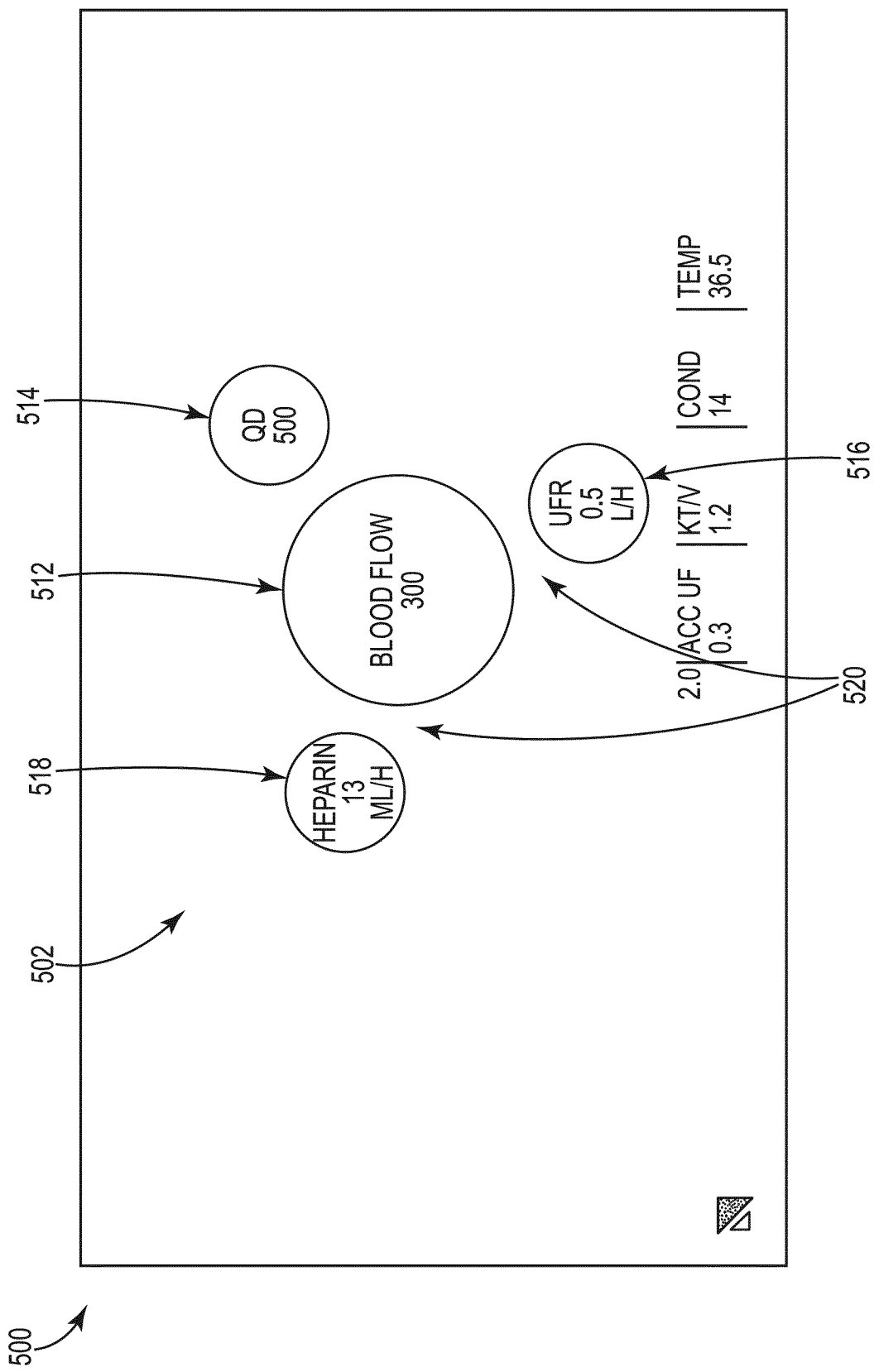

After the priming is complete, the exemplary graphical user interface 500 may be configured into a treatment mode as shown in FIG. 8B. For example, when in treatment mode, the operation region 502 may include one or more process feature graphical elements for use in a treatment and the settings region 504 may include one or more settings and/or parameters for use in a treatment. Additionally, the graphical user interface 500 may be configured such that the operations region 502 may be enlarged and the setting region 504 hidden as shown in FIG. 8C by, e.g., selection of minimize/maximize element 509.

The operation region 502 may include a blood process feature graphical element 512 (which, e.g., may be a stationary primary region or element), a dialysate-related process feature graphical element 514, an ultrafiltration process feature graphical element 516, and an anticoagulation process feature graphical element 518. Such process feature graphical elements 512, 514, 516, 518 may be similar to the process feature graphical elements previously described herein. For example, when the process feature graphical elements 512, 514, 516, 518 are separated by space 520 from each other, the process feature graphical elements 512, 514, 516, 518 may be described to be in an inactive state, and in turn, the process features associated therewith and represented thereby are also in an inactive state.

Figure 8D:
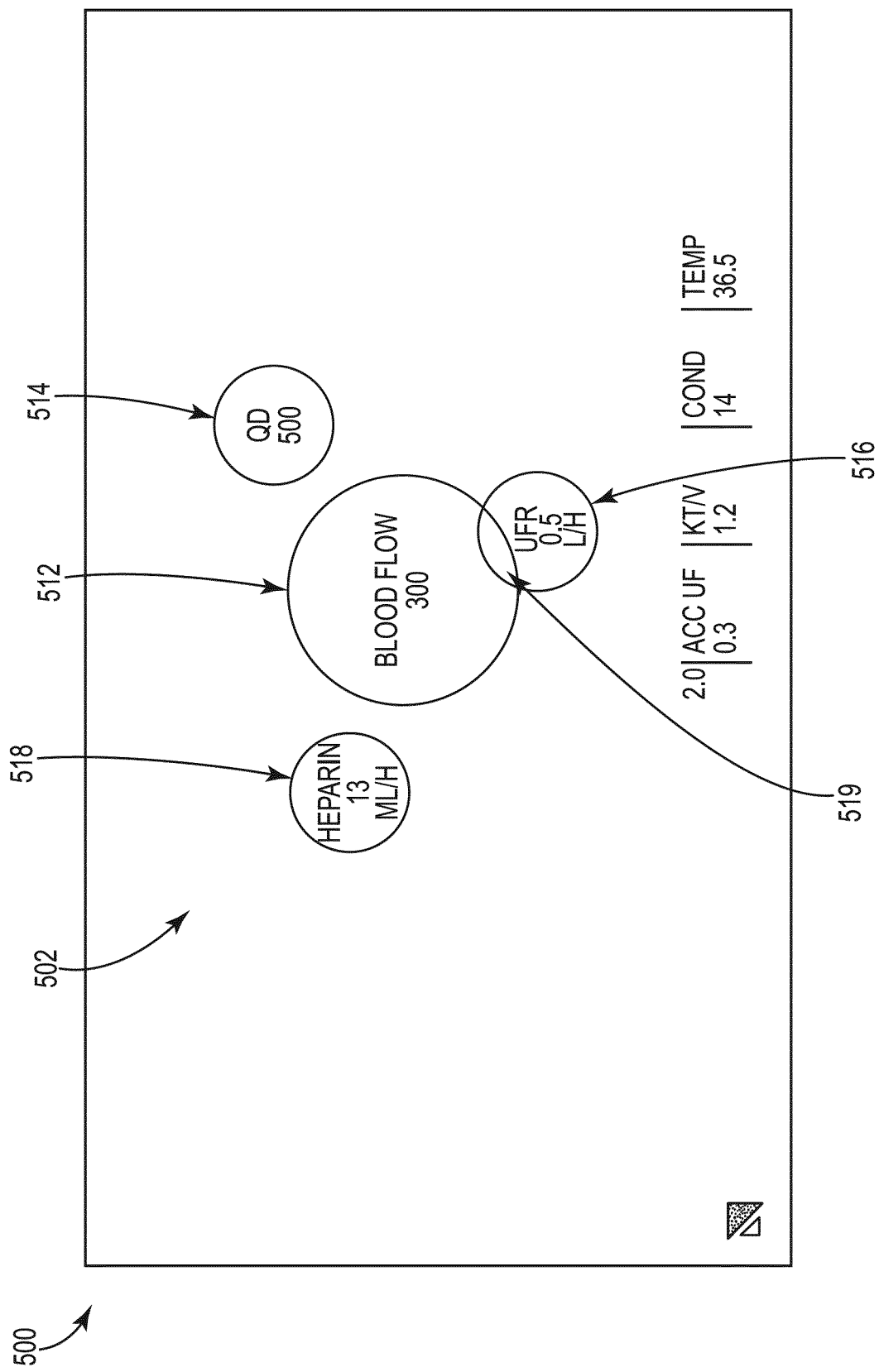

Each process feature graphical elements 514, 516, 518 may be moved, e.g., either automatically by the system or by a user, to overlap the blood process feature graphical element 512 to indicate that the moved and overlapped process feature graphical element 514, 516, 518 are in the active state. For example, as shown in FIG. 8D, the ultrafiltration process feature graphical element 516 has been moved to overlap a portion or area of the blood process feature graphical element 512 to, e.g., indicate that the ultrafiltration process feature graphical element 518, and in turn, the ultrafiltration processes associated therewith and represented thereby, are active (e.g., ready for use, etc.). As shown, the ultrafiltration process feature graphical element 516 and the blood process feature graphical element 512 may overlap to define an overlap area 519 (e.g., similar to the overlapping areas of circles in Venn diagrams).

Figure 8E:
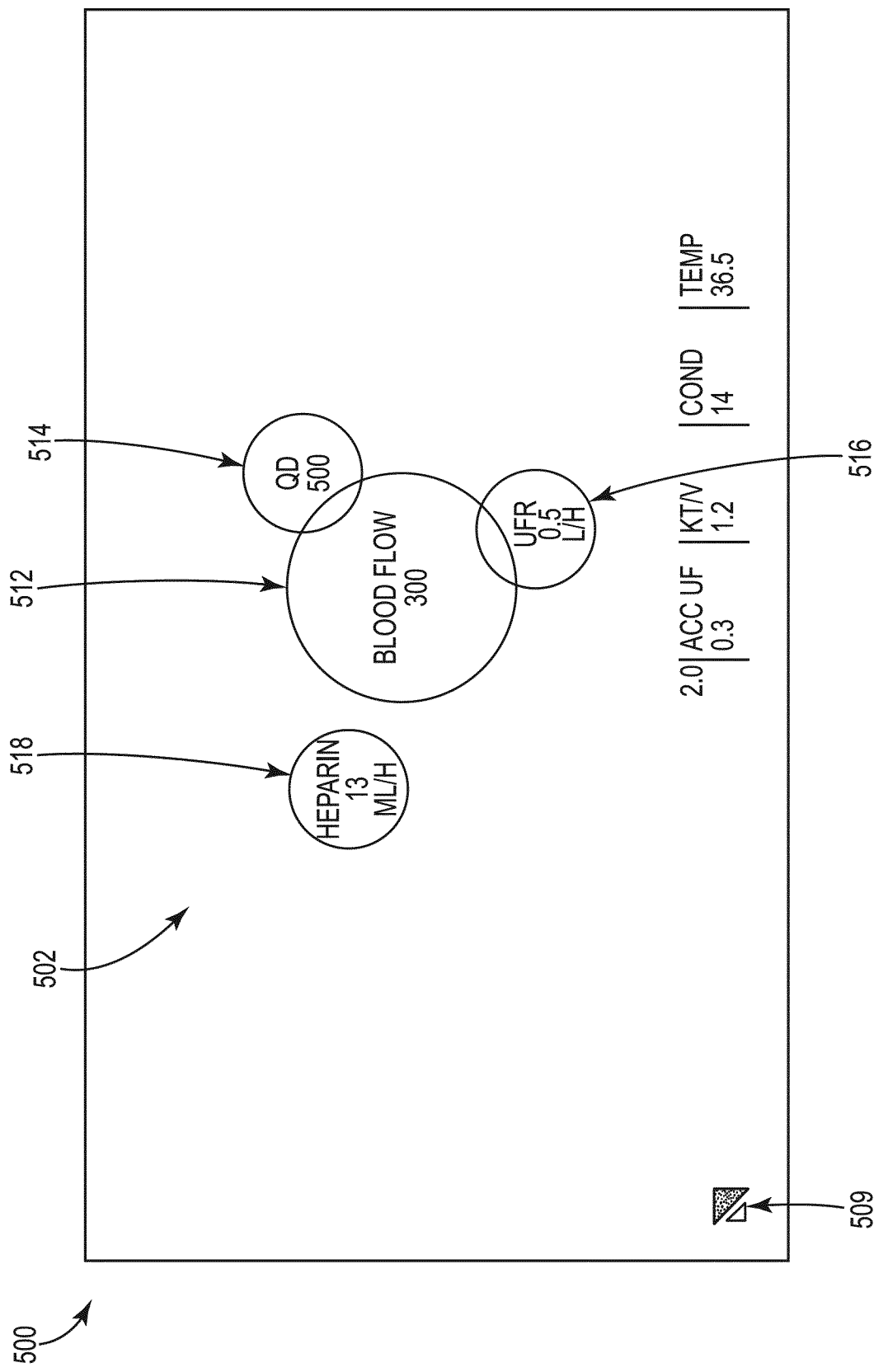
Figure 8F:
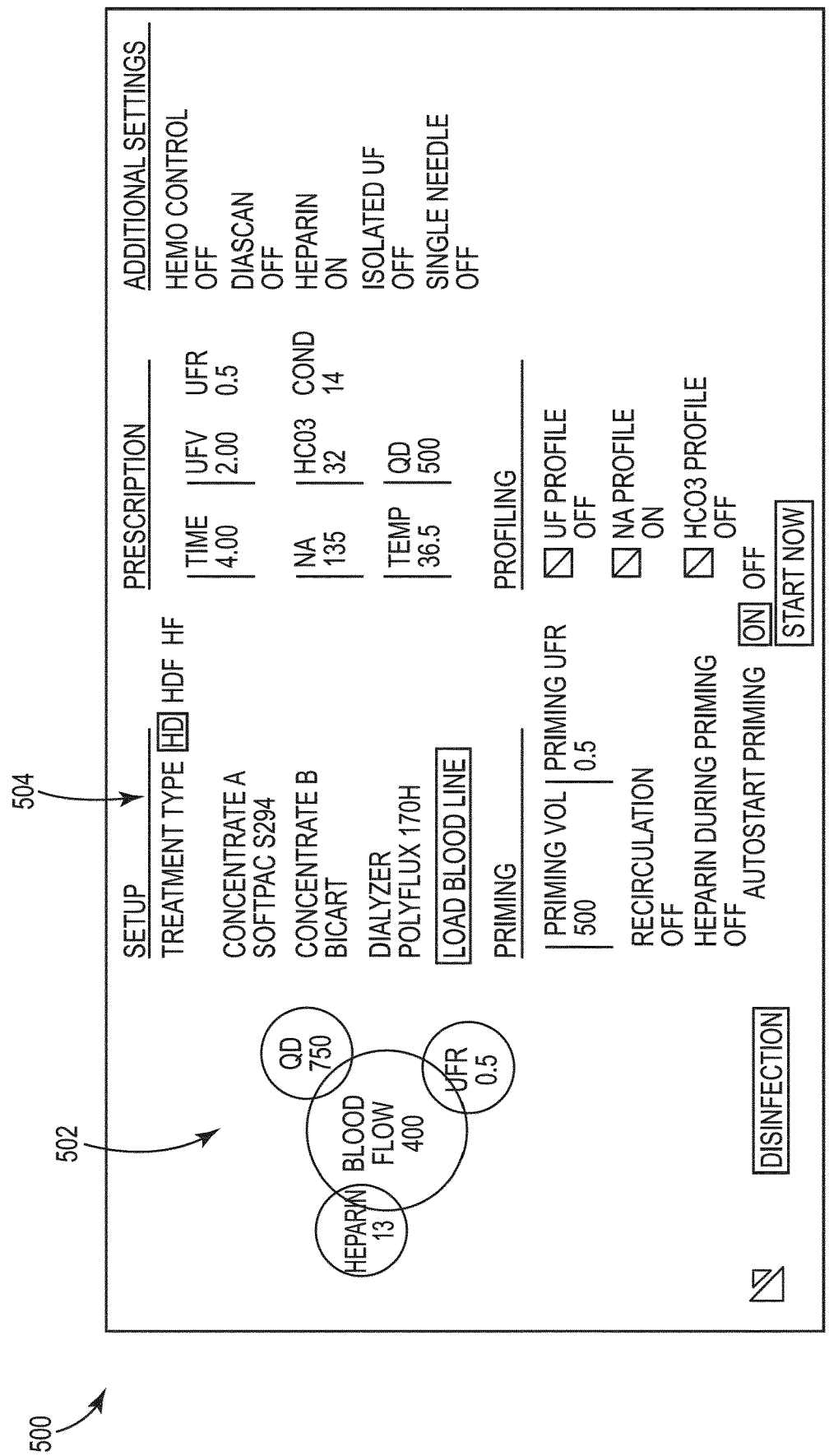
Figure 9:
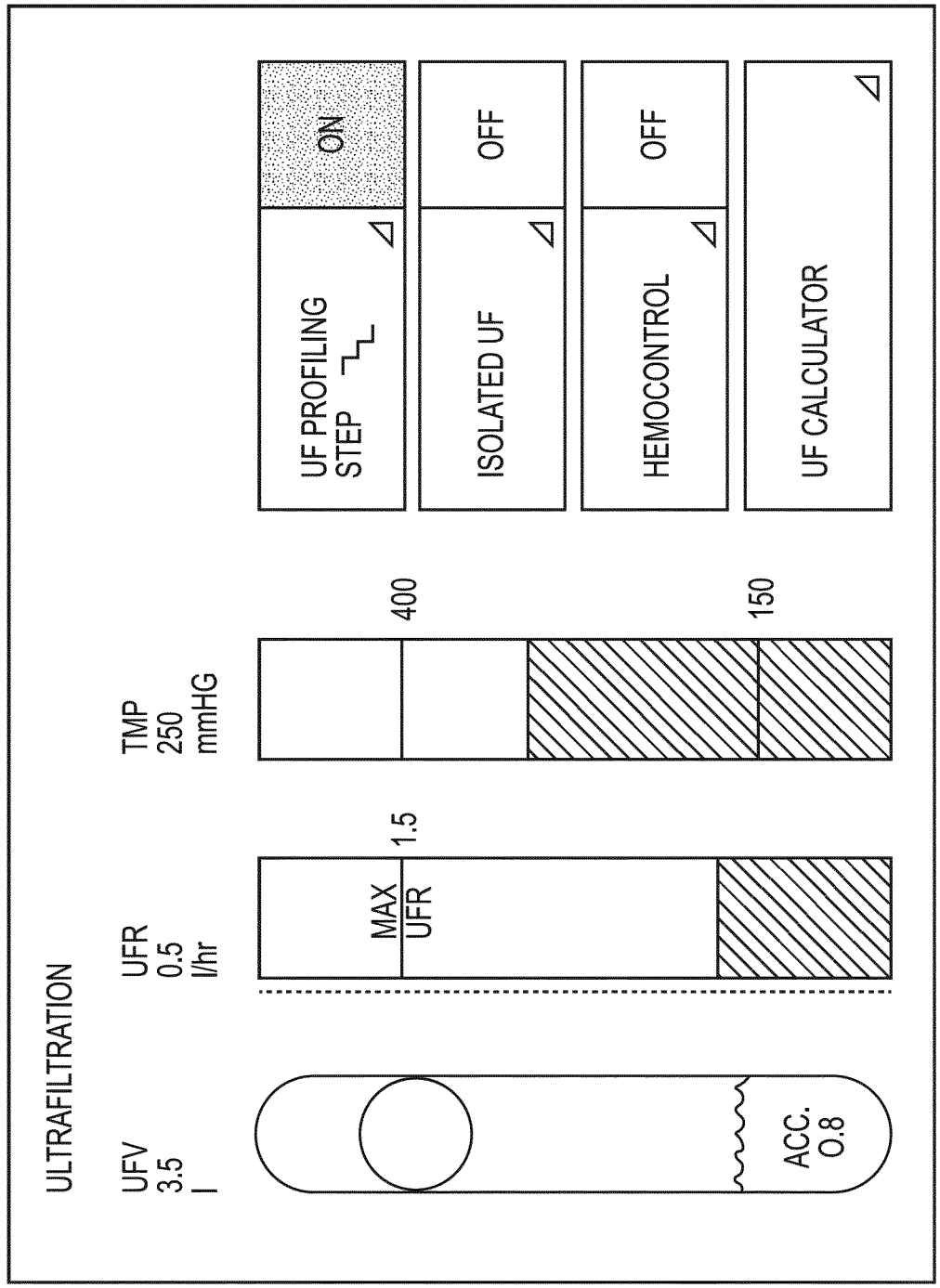
FIG. 9 depicts an exemplary adjustment region for use in the graphical user interfaces of FIGS. 3-8.

Likewise, the dialysate-related process feature graphical element 514 and the anticoagulation process feature graphical element 518 may be moved proximate to and overlapped with the blood process feature graphical element 512 to, e.g., indicate that the dialysate-related process feature graphical element 514 and the anticoagulation process feature graphical element 518, and in turn, the processes associated therewith and represented thereby, are active (e.g., ready for use, etc.) as shown in FIG. 8E. Additionally, the minimize/maximize element 509 may be again selected when the operation region 502 is enlarged as shown in FIG. 8E to again return to the graphical user interface 500 including a smaller operation region 502 with settings region 504 as shown in FIG. 8F.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
   extracorporeal blood treatment apparatus for use during an extracorporeal blood treatment comprising a blood pressure sensor to sense a patient's blood pressure;
   a display apparatus comprising a graphical user interface configured to depict a human-shaped graphical element and a heart-shaped graphical element at least partially within the human-shaped graphical element; and
   a computing apparatus comprising one or more processors, wherein the computing apparatus is operatively coupled to the extracorporeal blood treatment apparatus and the display apparatus, wherein the computing apparatus is configured to:
      display on the graphical user interface the human-shaped graphical element and the heart-shaped graphical element at least partially within the human-shaped graphical element using the one or more processors,
      allow a user to select the heart-shaped graphical element to initiate the blood pressure sensor to perform a blood pressure measurement on the patient,
      determine the patient's blood pressure using the blood pressure sensor in response to selection of the heart-shaped graphical element,
      display the measured blood pressure of the patient on the graphical user interface, and
      display on the graphical user interface a blood process feature graphical element using the one or more processors, wherein the human-shaped graphical element and the blood process feature graphical element are separated by space, wherein the human-shaped graphical element is movable proximate the blood process feature graphical element to indicate that venous and arterial blood lines are connecting the patient to a blood circuit of the extracorporeal blood treatment apparatus,
   wherein the human-shaped graphical element further comprises a connection area corresponding to the blood process feature graphical element and the blood process feature graphical element comprises a connection area corresponding to the human-shaped graphical element, wherein the connection area of the human-shaped graphical element is at least proximate to the connection area of the blood process feature graphical element when the human-shaped graphical element is proximate the blood process feature graphical element to indicate that venous and arterial blood lines are connecting the patient to the blood circuit of the extracorporeal blood treatment apparatus.

2. The system of claim 1, wherein the measured blood pressure of the patient is displayed at least partially within the human-shaped graphical element on the graphical user interface.

3. The system of claim 1, wherein the computing apparatus is further configured to, upon initialization of the blood pressure sensor to perform a blood pressure measurement on the patient, graphically animate the heart-shaped graphical element to indicate that the user has initiated a blood pressure measurement and that the blood pressure measurement is occurring using the blood pressure sensor.

4. The system of claim 3, wherein the graphical animation of the heart-shaped graphical element comprises the heart-shaped graphical element pulsating.

5. The system of claim 1, wherein the extracorporeal blood treatment apparatus further comprises a heart rate sensor to measure the patient's heart rate, wherein the computing apparatus is further configured to:
    allow a user to select a heart rate area of the human-shaped graphical element to initiate the heart rate sensor to perform a heart rate measurement;
    determine the patient's heart rate using the heart rate sensor in response to selection of the heart rate area of the human-shaped graphical element; and
    display the measured heart rate of the patient on the graphical user interface.

6. The system of claim 1, wherein the extracorporeal blood treatment apparatus comprises one or more waste sensors to determine an amount of waste being removed from the patient, wherein the human-shaped graphical element comprises graphical indicia indicative of the amount of waste removed from the patient.

7. The system of claim 1, wherein the human-shaped graphical element comprises a graphical facial expression configured to indicate happiness when an extracorporeal blood treatment is complete.

8. The system of claim 1, wherein the graphical user interface is configured to depict a graphical representation of at least one of the venous and arterial blood lines extending from the human-shaped graphical element and another graphical element on the graphical user interface to indicate that venous and arterial blood lines are connecting the patient to a blood circuit of the extracorporeal blood treatment apparatus.

9. The system of claim 8, wherein the extracorporeal blood treatment apparatus comprises one or more blood circuit pressure sensors to measure venous blood circuit pressure and arterial blood circuit pressure in the blood circuit, wherein the graphical user interface is further configured to depict a blood circuit pressure graphical representation representative of at least one of venous blood pressure of the patient and arterial blood pressure of the patient measured by the one or more blood circuit pressure sensors proximate the graphical depiction of at least one of the venous and arterial blood lines.

10. The system of claim 1, wherein the computing apparatus is further configured to allow a user to select a graphical area proximate or within the human-shaped graphical element to display a patient information region on the graphical user interface comprising patient-related information, wherein the patient-related information comprises at least one of a prescription, medication condition history, treatment history, a treatment summary, patient notes, and vital signs.

11. The system of claim 1, wherein the connection area of the human-shaped graphical element is configured to be in at least contact with the connection area of the blood process feature graphical element when the human-shaped graphical element is proximate the blood process feature graphical element.

12. The system of claim 1, wherein the display apparatus comprises a touchscreen.

* * * * *